US012678160B2

(12) United States Patent
Shelton, IV et al.

(10) Patent No.: US 12,678,160 B2
(45) Date of Patent: Jul. 14, 2026

(54) SURGICAL INSTRUMENT COMPRISING AN ADAPTIVE CONTROL SYSTEM

(71) Applicant: CILAG GMBH INTERNATIONAL, Zug (CH)

(72) Inventors: Frederick E. Shelton, IV, Hillsboro, OH (US); Gregory J. Bakos, Mason, OH (US); Jason L. Harris, Lebanon, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 19/029,607

(22) Filed: Jan. 17, 2025

(65) Prior Publication Data

US 2025/0160829 A1     May 22, 2025

Related U.S. Application Data

(63) Continuation of application No. 18/430,065, filed on Feb. 1, 2024, now Pat. No. 12,295,574, which is a continuation of application No. 17/403,077, filed on Aug. 16, 2021, now Pat. No. 11,931,027, which is a
(Continued)

(51) Int. Cl.
| | |
|---|---|
| *A61B 17/072* | (2006.01) |
| *A61B 17/115* | (2006.01) |
| *A61B 18/14* | (2006.01) |
| *A61B 17/00* | (2006.01) |
(Continued)

(52) U.S. Cl.
CPC ...... *A61B 17/072* (2013.01); *A61B 17/07207* (2013.01); *A61B 17/115* (2013.01); *A61B 18/1445* (2013.01); *A61B 2017/00022* (2013.01); *A61B 2017/00026* (2013.01); *A61B*

*2017/00039* (2013.01); *A61B 2017/00061* (2013.01); *A61B 2017/00137* (2013.01); *A61B 2017/00398* (2013.01); *A61B 2017/00734* (2013.01); *A61B 17/068* (2013.01); *A61B 2017/07214* (2013.01); *A61B 2017/07264* (2013.01); *A61B 2017/07271* (2013.01); *A61B 2017/07285* (2013.01); *A61B 2018/00404* (2013.01); *A61B 2018/0063* (2013.01)

(58) Field of Classification Search
CPC .................................................. A61B 17/072
See application file for complete search history.

(56) References Cited

U.S. PATENT DOCUMENTS

| | | |
|---|---|---|
| 5,322,055 A | 6/1994 | Davison |
| 5,403,312 A | 4/1995 | Yates |
| 5,735,848 A | 4/1998 | Yates |
(Continued)

FOREIGN PATENT DOCUMENTS

| | | |
|---|---|---|
| BR | 112020019638 A2 | 1/2021 |

*Primary Examiner* — Nathaniel C Chukwurah
(74) *Attorney, Agent, or Firm* — Troutman Pepper Locke LLP

(57) ABSTRACT

A surgical instrument comprising a motor control system in communication with a closure motor and a drive motor is disclosed. The motor control system is configured to control the operation of the closure motor and the drive motor. The motor control system is configured to increase the clamping pressure applied by a first jaw during a second tissue cutting stroke as compared to the clamping pressure applied by the first jaw during a first tissue cutting stroke.

20 Claims, 18 Drawing Sheets

Related U.S. Application Data continuation of application No. 16/361,793, filed on Mar. 22, 2019, now Pat. No. 11,090,047.

(60) Provisional application No. 62/821,677, filed on Mar. 21, 2019, provisional application No. 62/807,310, filed on Feb. 19, 2019, provisional application No. 62/807,319, filed on Feb. 19, 2019, provisional application No. 62/807,309, filed on Feb. 19, 2019, provisional application No. 62/650,887, filed on Mar. 30, 2018, provisional application No. 62/649,302, filed on Mar. 28, 2018, provisional application No. 62/649,294, filed on Mar. 28, 2018, provisional application No. 62/649,300, filed on Mar. 28, 2018, provisional application No. 62/649,309, filed on Mar. 28, 2018, provisional application No. 62/649,310, filed on Mar. 28, 2018, provisional application No. 62/649,291, filed on Mar. 28, 2018, provisional application No. 62/649,296, filed on Mar. 28, 2018, provisional application No. 62/649,333, filed on Mar. 28, 2018, provisional application No. 62/649,327, filed on Mar. 28, 2018, provisional application No. 62/649,315, filed on Mar. 28, 2018, provisional application No. 62/649,313, filed on Mar. 28, 2018, provisional application No. 62/649,320, filed on Mar. 28, 2018, provisional application No. 62/649,307, filed on Mar. 28, 2018, provisional application No. 62/649,323, filed on Mar. 28, 2018.

(51) Int. Cl.
*A61B 17/068* (2006.01)
*A61B 18/00* (2006.01)

(56) References Cited

U.S. PATENT DOCUMENTS

| | | | | |
|---|---|---|---|---|
| 5,833,690 | A | 11/1998 | Yates | |
| 5,873,873 | A | 2/1999 | Smith | |
| 5,980,510 | A | 11/1999 | Tsonton | |
| 6,325,811 | B1 | 12/2001 | Messerly | |
| 6,773,444 | B2 | 8/2004 | Messerly | |
| 6,783,524 | B2 | 8/2004 | Anderson | |
| 6,978,921 | B2 | 12/2005 | Shelton, IV | |
| 6,988,649 | B2 | 1/2006 | Shelton, IV | |
| 7,000,818 | B2 | 2/2006 | Shelton, IV | |
| 7,044,352 | B2 | 5/2006 | Shelton, IV | |
| 7,143,923 | B2 | 12/2006 | Shelton, IV | |
| 7,422,139 | B2 | 9/2008 | Shelton, IV | |
| 7,464,849 | B2 | 12/2008 | Shelton, IV | |
| 7,670,334 | B2 | 3/2010 | Hueil | |
| 7,753,245 | B2 | 7/2010 | Boudreaux | |
| 7,845,537 | B2 | 12/2010 | Shelton, IV | |
| 7,980,443 | B2 | 7/2011 | Scheib | |
| 8,210,411 | B2 | 7/2012 | Yates | |
| 8,220,688 | B2 | 7/2012 | Laurent | |
| 8,308,040 | B2 | 11/2012 | Huang | |
| 8,393,514 | B2 | 3/2013 | Shelton, IV | |
| 8,461,744 | B2 | 6/2013 | Wiener | |
| 8,499,992 | B2 | 8/2013 | Whitman | |
| 8,561,870 | B2 | 10/2013 | Baxter, III | |
| 8,608,045 | B2 | 12/2013 | Smith | |
| 8,623,027 | B2 | 1/2014 | Price | |
| 8,733,613 | B2 | 5/2014 | Huitema | |
| 9,023,071 | B2 | 5/2015 | Miller | |
| 9,050,083 | B2 | 6/2015 | Yates | |
| 9,072,535 | B2 | 7/2015 | Shelton, IV | |
| 9,095,367 | B2 | 8/2015 | Olson | |
| 9,101,358 | B2 | 8/2015 | Kerr | |
| 9,220,502 | B2 | 12/2015 | Zemlok | |
| 9,345,481 | B2 | 5/2016 | Hall | |
| 9,381,058 | B2 | 7/2016 | Houser | |
| 9,393,037 | B2 | 7/2016 | Olson | |
| 9,724,094 | B2 * | 8/2017 | Baber | H02H 3/207 |
| 9,913,642 | B2 | 3/2018 | Leimbach | |
| 11,343,803 | B2 | 5/2022 | Futaki | |
| 2006/0079874 | A1 | 4/2006 | Faller | |
| 2007/0175955 | A1 | 8/2007 | Shelton | |
| 2007/0191713 | A1 | 8/2007 | Eichmann | |
| 2007/0282333 | A1 | 12/2007 | Fortson | |
| 2008/0200940 | A1 | 8/2008 | Eichmann | |
| 2009/0001122 | A1 | 1/2009 | Prommersberger | |
| 2009/0105750 | A1 | 4/2009 | Price | |
| 2010/0069940 | A1 | 3/2010 | Miller | |
| 2010/0264194 | A1 | 10/2010 | Huang | |
| 2011/0015660 | A1 | 1/2011 | Wiener | |
| 2012/0029546 | A1 | 2/2012 | Robertson | |
| 2012/0112687 | A1 | 5/2012 | Houser | |
| 2012/0116265 | A1 | 5/2012 | Houser | |
| 2012/0248167 | A1 | 10/2012 | Flanagan | |
| 2013/0168431 | A1 | 7/2013 | Zemlok | |
| 2014/0263541 | A1 | 9/2014 | Leimbach | |
| 2014/0263552 | A1 | 9/2014 | Hall | |
| 2015/0153642 | A1 | 6/2015 | Yang | |
| 2015/0297232 | A1 | 10/2015 | Huitema | |
| 2015/0374374 | A1 | 12/2015 | Shelton, IV | |
| 2016/0066914 | A1 * | 3/2016 | Baber | H02H 1/06 227/176.1 |
| 2016/0089142 | A1 | 3/2016 | Harris | |
| 2016/0128691 | A1 | 5/2016 | Okoniewski | |
| 2016/0249945 | A1 * | 9/2016 | Shelton, IV | A61B 17/115 606/171 |
| 2016/0287251 | A1 | 10/2016 | Shelton, IV | |
| 2017/0083125 | A1 | 3/2017 | Dow | |
| 2017/0083126 | A1 | 3/2017 | Lim | |
| 2017/0132611 | A1 | 5/2017 | Wolfe | |
| 2017/0245854 | A1 | 8/2017 | Zemlok | |
| 2017/0265865 | A1 | 9/2017 | Burbank | |
| 2017/0265954 | A1 | 9/2017 | Burbank | |
| 2017/0290586 | A1 | 10/2017 | Wellman | |
| 2017/0296213 | A1 * | 10/2017 | Swensgard | A61B 17/32 |
| 2017/0333033 | A1 | 11/2017 | Valentine | |
| 2018/0008260 | A1 | 1/2018 | Baxter, III | |
| 2019/0000464 | A1 | 1/2019 | Shelton, IV | |

* cited by examiner

SURGICAL INSTRUMENT COMPRISING AN ADAPTIVE CONTROL SYSTEM

CROSS-REFERENCE TO RELATED APPLICATIONS

This application is a continuation application claiming priority under 35 U.S.C. § 120 to U.S. patent application Ser. No. 18/430,065, entitled SURGICAL INSTRUMENT COMPRISING AN ADAPTIVE CONTROL SYSTEM, filed Feb. 1, 2024, which is a continuation of U.S. patent application Ser. No. 17/403,077, entitled SURGICAL INSTRUMENT COMPRISING AN ADAPTIVE CONTROL SYSTEM, filed Aug. 16, 2021, now U.S. Pat. No. 11,931,027, which is a continuation of U.S. patent application Ser. No. 16/361,793, entitled SURGICAL INSTRUMENT COMPRISING AN ADAPTIVE CONTROL SYSTEM, filed Mar. 22, 2019, now U.S. Pat. No. 11,090,047, which claims the benefit of U.S. Provisional Patent Application Ser. No. 62/821,677, entitled SURGICAL INSTRUMENT COMPRISING AN ADAPTIVE CONTROL SYSTEM, filed Mar. 21, 2019, the disclosure of which is incorporated by reference herein in its entirety; U.S. patent application Ser. No. 16/361,793 further claims the benefit of U.S. Provisional Patent Application Ser. No. 62/807,310, entitled METHODS FOR CONTROLLING A POWERED SURGICAL STAPLER THAT HAS SEPARATE ROTARY CLOSURE AND FIRING SYSTEMS, filed Feb. 19, 2019, of U.S. Provisional Patent Application Ser. No. 62/807,319, entitled SURGICAL STAPLING DEVICES WITH IMPROVED LOCKOUT SYSTEMS, filed Feb. 19, 2019, and of U.S. Provisional Patent Application Ser. No. 62/807,309, entitled SURGICAL STAPLING DEVICES WITH IMPROVED ROTARY DRIVEN CLOSURE SYSTEMS, filed Feb. 19, 2019, the disclosures of which are incorporated by reference herein in their entireties; U.S. patent application Ser. No. 16/361,793 further claims the benefit of U.S. Provisional Patent Application Ser. No. 62/650,887, entitled SURGICAL SYSTEMS WITH OPTIMIZED SENSING CAPABILITIES, filed Mar. 30, 2018, the disclosure of which is incorporated by reference herein in its entirety; U.S. patent application Ser. No. 16/361,793 further claims the benefit of U.S. Provisional Patent Application Ser. No. 62/649,302, entitled INTERACTIVE SURGICAL SYSTEMS WITH ENCRYPTED COMMUNICATION CAPABILITIES, filed Mar. 28, 2018, of U.S. Provisional Patent Application Ser. No. 62/649,294, entitled DATA STRIPPING METHOD TO INTERROGATE PATIENT RECORDS AND CREATE ANONYMIZED RECORD, filed Mar. 28, 2018, of U.S. Provisional Patent Application Ser. No. 62/649,300, entitled SURGICAL HUB SITUATIONAL AWARENESS, filed Mar. 28, 2018, of U.S. Provisional Patent Application Ser. No. 62/649,309, entitled SURGICAL HUB SPATIAL AWARENESS TO DETERMINE DEVICES IN OPERATING THEATER, filed Mar. 28, 2018, of U.S. Provisional Patent Application Ser. No. 62/649,310, entitled COMPUTER IMPLEMENTED INTERACTIVE SURGICAL SYSTEMS, filed Mar. 28, 2018, of U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT, filed Mar. 28, 2018, of U.S. Provisional Patent Application Ser. No. 62/649,296, entitled ADAPTIVE CONTROL PROGRAM UPDATES FOR SURGICAL DEVICES, filed Mar. 28, 2018, of U.S. Provisional Patent Application Ser. No. 62/649,333, entitled CLOUD-BASED MEDICAL ANA- LYTICS FOR CUSTOMIZATION AND RECOMMENDATIONS TO A USER, filed Mar. 28, 2018, of U.S. Provisional Patent Application Ser. No. 62/649,327, entitled CLOUD-BASED MEDICAL ANALYTICS FOR SECURITY AND AUTHENTICATION TRENDS AND REACTIVE MEASURES, filed Mar. 28, 2018, of U.S. Provisional Patent Application Ser. No. 62/649,315, entitled DATA HANDLING AND PRIORITIZATION IN A CLOUD ANALYTICS NETWORK, filed Mar. 28, 2018, of U.S. Provisional Patent Application Ser. No. 62/649,313, entitled CLOUD INTERFACE FOR COUPLED SURGICAL DEVICES, filed Mar. 28, 2018, of U.S. Provisional Patent Application Ser. No. 62/649,320, entitled DRIVE ARRANGEMENTS FOR ROBOT-ASSISTED SURGICAL PLATFORMS, filed Mar. 28, 2018, of U.S. Provisional Patent Application Ser. No. 62/649,307, entitled AUTOMATIC TOOL ADJUSTMENTS FOR ROBOT-ASSISTED SURGICAL PLATFORMS, filed Mar. 28, 2018, and of U.S. Provisional Patent Application Ser. No. 62/649,323, entitled SENSING ARRANGEMENTS FOR ROBOT-ASSISTED SURGICAL PLATFORMS, filed Mar. 28, 2018, the disclosures of which are incorporated by reference herein in their entireties.

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
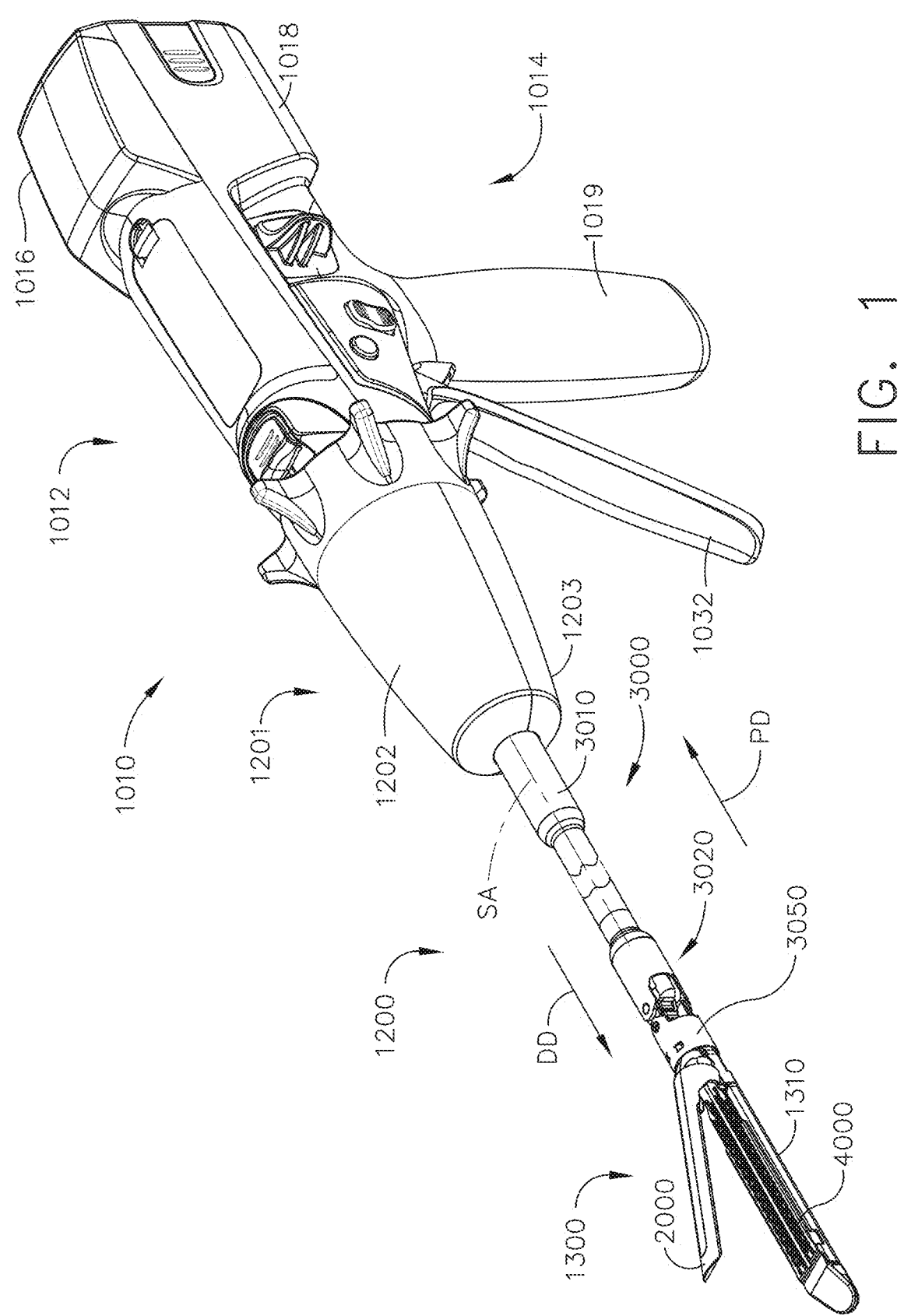
FIG. 1 is a perspective view of a powered surgical stapling system.

Applicant of the present application owns the following U.S. Patent Applications that were filed on Feb. 21, 2019 and which are each herein incorporated by reference in their respective entireties:

U.S. patent application Ser. No. 16/281,658, entitled METHODS FOR CONTROLLING A POWERED SURGICAL STAPLER THAT HAS SEPARATE ROTARY CLOSURE AND FIRING SYSTEMS;

U.S. patent application Ser. No. 16/281,675, entitled SURGICAL STAPLERS WITH ARRANGEMENTS FOR MAINTAINING A FIRING MEMBER THEREOF IN A LOCKED CONFIGURATION UNLESS A COMPATIBLE CARTRIDGE HAS BEEN INSTALLED THEREIN;

U.S. patent application Ser. No. 16/281,685, entitled SURGICAL INSTRUMENT COMPRISING CO-OPERATING LOCKOUT FEATURES;

U.S. patent application Ser. No. 16/281,693, entitled SURGICAL STAPLING ASSEMBLY COMPRISING A LOCKOUT AND AN EXTERIOR ACCESS ORIFICE TO PERMIT ARTIFICIAL UNLOCKING OF THE LOCKOUT;

U.S. patent application Ser. No. 16/281,704, entitled SURGICAL STAPLING DEVICES WITH FEATURES FOR BLOCKING ADVANCEMENT OF A CAMMING ASSEMBLY OF AN INCOMPATIBLE CARTRIDGE INSTALLED THEREIN;

U.S. patent application Ser. No. 16/281,707, entitled STAPLING INSTRUMENT COMPRISING A DEACTIVATABLE LOCKOUT;

U.S. patent application Ser. No. 16/281,741, entitled SURGICAL INSTRUMENT COMPRISING A JAW CLOSURE LOCKOUT;

U.S. patent application Ser. No. 16/281,762, entitled SURGICAL STAPLING DEVICES WITH CARTRIDGE COMPATIBLE CLOSURE AND FIRING LOCKOUT ARRANGEMENTS;

U.S. patent application Ser. No. 16/281,660, entitled SURGICAL STAPLE CARTRIDGE WITH FIRING MEMBER DRIVEN CAMMING ASSEMBLY THAT HAS AN ONBOARD TISSUE CUTTING FEATURE;

U.S. patent application Ser. No. 16/281,666, entitled SURGICAL STAPLING DEVICES WITH IMPROVED ROTARY DRIVEN CLOSURE SYSTEMS;

U.S. patent application Ser. No. 16/281,672, entitled SURGICAL STAPLING DEVICES WITH ASYMMETRIC CLOSURE FEATURES;

U.S. patent application Ser. No. 16/281,678, entitled ROTARY DRIVEN FIRING MEMBERS WITH DIFFERENT ANVIL AND CHANNEL ENGAGEMENT FEATURES; and U.S. patent application Ser. No. 16/281,682, entitled SURGICAL STAPLING DEVICE WITH SEPARATE ROTARY DRIVEN CLOSURE AND FIRING SYSTEMS AND FIRING MEMBER THAT ENGAGES BOTH JAWS WHILE FIRING.

Applicant of the present application owns the following U.S. Provisional Patent Applications that were filed on Feb. 19, 2019 and which are each herein incorporated by reference in their respective entireties:

U.S. Provisional Patent Application Ser. No. 62/807,310, entitled METHODS FOR CONTROLLING A POWERED SURGICAL STAPLER THAT HAS SEPARATE ROTARY CLOSURE AND FIRING SYSTEMS;

U.S. Provisional Patent Application Ser. No. 62/807,319, entitled SURGICAL STAPLING DEVICES WITH IMPROVED LOCKOUT SYSTEMS; and U.S. Provisional Patent Application Ser. No. 62/807,309, entitled SURGICAL STAPLING DEVICES WITH IMPROVED ROTARY DRIVEN CLOSURE SYSTEMS.

Applicant of the present application owns the following U.S. Patent Applications that were filed on Dec. 14, 2018 which are each herein incorporated by reference in their respective entireties:

U.S. patent application Ser. No. 16/220,281, entitled SURGICAL INSTRUMENT WITH A HARDWARE-ONLY CONTROL CIRCUIT;

U.S. patent application Ser. No. 16/220,301, entitled SURGICAL INSTRUMENT WITH ACOUSTIC-BASED MOTOR CONTROL;

U.S. patent application Ser. No. 16/220,313, entitled SURGICAL INSTRUMENT COMPRISING A PLURALITY OF DRIVE SYSTEMS;

U.S. patent application Ser. No. 16/220,296, entitled SURGICAL INSTRUMENT COMPRISING A CONTROL CIRCUIT;

U.S. patent application Ser. No. 16/220,309, entitled SURGICAL INSTRUMENTS COMPRISING BUTTON CIRCUITS;

U.S. patent application Ser. No. 16/220,318, entitled SURGICAL INSTRUMENT COMPRISING A CONTROL SYSTEM THAT USES INPUT FROM A STRAIN GAGE CIRCUIT;

5

U.S. patent application Ser. No. 16/220,273, entitled SURGICAL INSTRUMENT WITH A SENSING ARRAY; and U.S. patent application Ser. No. 16/220,280, entitled SURGICAL INSTRUMENT WITH ENVIRONMENT SENSING.

Applicant of the present application owns the following U.S. Provisional Patent Applications, filed on Dec. 12, 2018, each of which is herein incorporated by reference in its entirety:

U.S. Provisional Patent Application Ser. No. 62/778,571, entitled SURGICAL INSTRUMENT SYSTEMS;

U.S. Provisional Patent Application Ser. No. 62/778,572, entitled SURGICAL INSTRUMENT SYSTEMS; and U.S. Provisional Patent Application Ser. No. 62/778,573, entitled SURGICAL INSTRUMENT SYSTEMS.

Applicant of the present application owns the following U.S. Patent Applications that were filed on Oct. 26, 2018 which are each herein incorporated by reference in their respective entireties:

U.S. patent application Ser. No. 16/172,130, entitled CLIP APPLIER COMPRISING INTERCHANGE-ABLE CLIP RELOADS;

U.S. patent application Ser. No. 16/172,066, entitled CLIP APPLIER COMPRISING A MOVABLE CLIP MAGAZINE;

U.S. patent application Ser. No. 16/172,078, entitled CLIP APPLIER COMPRISING A ROTATABLE CLIP MAGAZINE;

U.S. patent application Ser. No. 16/172,087, entitled CLIP APPLIER COMPRISING CLIP ADVANCING SYSTEMS;

U.S. patent application Ser. No. 16/172,094, entitled CLIP APPLIER COMPRISING A CLIP CRIMPING SYSTEM;

U.S. patent application Ser. No. 16/172,128, entitled CLIP APPLIER COMPRISING A RECIPROCATING CLIP ADVANCING MEMBER;

U.S. patent application Ser. No. 16/172,168, entitled CLIP APPLIER COMPRISING A MOTOR CON-TROLLER;

U.S. patent application Ser. No. 16/172,164, entitled SURGICAL SYSTEM COMPRISING A SURGICAL TOOL AND A SURGICAL HUB; and U.S. patent application Ser. No. 16/172,303, entitled METHOD FOR OPERATING A POWERED ARTICULATING MULTI-CLIP APPLIER.

Applicant of the present application owns the following U.S. Patent Applications that were filed on Oct. 26, 2018, which are each herein incorporated by reference in their respective entireties:

U.S. patent application Ser. No. 16/172,328, entitled METHOD OF HUB COMMUNICATION WITH SURGICAL INSTRUMENT SYSTEMS;

U.S. patent application Ser. No. 16/172,280, entitled METHOD FOR PRODUCING A SURGICAL INSTRUMENT COMPRISING A SMART ELECTRI-CAL SYSTEM;

U.S. patent application Ser. No. 16/172,219, entitled METHOD OF HUB COMMUNICATION WITH SURGICAL INSTRUMENT SYSTEMS;

U.S. patent application Ser. No. 16/172,248, entitled METHOD FOR COMMUNICATING WITH SURGI-CAL INSTRUMENT SYSTEMS;

U.S. patent application Ser. No. 16/172,198, entitled METHOD OF HUB COMMUNICATION WITH SURGICAL INSTRUMENT SYSTEMS; and

6

U.S. patent application Ser. No. 16/172,155, entitled METHOD OF HUB COMMUNICATION WITH SURGICAL INSTRUMENT SYSTEMS.

Applicant of the present application owns the following U.S. Patent Applications that were filed on Aug. 24, 2018, which are each herein incorporated by reference in their respective entireties:

U.S. patent application Ser. No. 16/112,129, entitled SURGICAL SUTURING INSTRUMENT CONFIG-URED TO MANIPULATE TISSUE USING MECHANICAL AND ELECTRICAL POWER;

U.S. Patent Application Ser. No. 16/112,155, entitled SURGICAL SUTURING INSTRUMENT COMPRIS-ING A CAPTURE WIDTH WHICH IS LARGER THAN TROCAR DIAMETER;

U.S. patent application Ser. No. 16/112,168, entitled SURGICAL SUTURING INSTRUMENT COMPRIS-ING A NON-CIRCULAR NEEDLE;

U.S. patent application Ser. No. 16/112,180, entitled ELECTRICAL POWER OUTPUT CONTROL BASED ON MECHANICAL FORCES;

U.S. Patent Application Ser. No. 16/112,193, entitled REACTIVE ALGORITHM FOR SURGICAL SYS-TEM;

U.S. patent application Ser. No. 16/112,099, entitled SURGICAL INSTRUMENT COMPRISING AN ADAPTIVE ELECTRICAL SYSTEM;

U.S. Patent Application Ser. No. 16/112,112, entitled CONTROL SYSTEM ARRANGEMENTS FOR A MODULAR SURGICAL INSTRUMENT;

U.S. Patent Application Ser. No. 16/112,119, entitled ADAPTIVE CONTROL PROGRAMS FOR A SUR-GICAL SYSTEM COMPRISING MORE THAN ONE TYPE OF CARTRIDGE;

U.S. patent application Ser. No. 16/112,097, entitled SURGICAL INSTRUMENT SYSTEMS COMPRIS-ING BATTERY ARRANGEMENTS;

U.S. patent application Ser. No. 16/112,109, entitled SURGICAL INSTRUMENT SYSTEMS COMPRIS-ING HANDLE ARRANGEMENTS;

U.S. patent application Ser. No. 16/112,114, entitled SURGICAL INSTRUMENT SYSTEMS COMPRIS-ING FEEDBACK MECHANISMS;

U.S. patent application Ser. No. 16/112,117, entitled SURGICAL INSTRUMENT SYSTEMS COMPRIS-ING LOCKOUT MECHANISMS;

U.S. patent application Ser. No. 16/112,095, entitled SURGICAL INSTRUMENTS COMPRISING A LOCKABLE END EFFECTOR SOCKET;

U.S. patent application Ser. No. 16/112,121, entitled SURGICAL INSTRUMENTS COMPRISING A SHIFTING MECHANISM;

U.S. Patent Application Ser. No. 16/112,151, entitled SURGICAL INSTRUMENTS COMPRISING A SYS-TEM FOR ARTICULATION AND ROTATION COM-PENSATION;

U.S. patent application Ser. No. 16/112,154, entitled SURGICAL INSTRUMENTS COMPRISING A BIASED SHIFTING MECHANISM;

U.S. patent application Ser. No. 16/112,226, entitled SURGICAL INSTRUMENTS COMPRISING AN ARTICULATION DRIVE THAT PROVIDES FOR HIGH ARTICULATION ANGLES;

U.S. patent application Ser. No. 16/112,062, entitled SURGICAL DISSECTORS AND MANUFACTUR-ING TECHNIQUES;

7

U.S. patent application Ser. No. 16/112,098, entitled SURGICAL DISSECTORS CONFIGURED TO APPLY MECHANICAL AND ELECTRICAL ENERGY;

U.S. patent application Ser. No. 16/112,237, entitled SURGICAL CLIP APPLIER CONFIGURED TO STORE CLIPS IN A STORED STATE;

U.S. patent application Ser. No. 16/112,245, entitled SURGICAL CLIP APPLIER COMPRISING AN EMPTY CLIP CARTRIDGE LOCKOUT;

U.S. patent application Ser. No. 16/112,249, entitled SURGICAL CLIP APPLIER COMPRISING AN AUTOMATIC CLIP FEEDING SYSTEM;

U.S. patent application Ser. No. 16/112,253, entitled SURGICAL CLIP APPLIER COMPRISING ADAPTIVE FIRING CONTROL; and U.S. patent application Ser. No. 16/112,257, entitled SURGICAL CLIP APPLIER COMPRISING ADAPTIVE CONTROL IN RESPONSE TO A STRAIN GAUGE CIRCUIT.

Applicant of the present application owns the following U.S. Patent Applications that were filed on May 1, 2018, and which are each herein incorporated by reference in their respective entireties:

U.S. Provisional Patent Application Ser. No. 62/665,129, entitled SURGICAL SUTURING SYSTEMS;

U.S. Provisional Patent Application Ser. No. 62/665,139, entitled SURGICAL INSTRUMENTS COMPRISING CONTROL SYSTEMS;

U.S. Provisional Patent Application Ser. No. 62/665,177, entitled SURGICAL INSTRUMENTS COMPRISING HANDLE ARRANGEMENTS;

U.S. Provisional Patent Application Ser. No. 62/665,128, entitled MODULAR SURGICAL INSTRUMENTS;

U.S. Provisional Patent Application Ser. No. 62/665,192, entitled SURGICAL DISSECTORS; and U.S. Provisional Patent Application Ser. No. 62/665,134, entitled SURGICAL CLIP APPLIER.

Applicant of the present application owns the following U.S. Patent Applications that were filed on Feb. 28, 2018, and which are each herein incorporated by reference in their respective entireties:

U.S. patent application Ser. No. 15/908,021, entitled SURGICAL INSTRUMENT WITH REMOTE RELEASE;

U.S. patent application Ser. No. 15/908,012, entitled SURGICAL INSTRUMENT HAVING DUAL ROTATABLE MEMBERS TO EFFECT DIFFERENT TYPES OF END EFFECTOR MOVEMENT;

U.S. patent application Ser. No. 15/908,040, entitled SURGICAL INSTRUMENT WITH ROTARY DRIVE SELECTIVELY ACTUATING MULTIPLE END EFFECTOR FUNCTIONS;

U.S. patent application Ser. No. 15/908,057, entitled SURGICAL INSTRUMENT WITH ROTARY DRIVE SELECTIVELY ACTUATING MULTIPLE END EFFECTOR FUNCTIONS;

U.S. patent application Ser. No. 15/908,058, entitled SURGICAL INSTRUMENT WITH MODULAR POWER SOURCES; and U.S. patent application Ser. No. 15/908,143, entitled SURGICAL INSTRUMENT WITH SENSOR AND/OR CONTROL SYSTEMS.

Applicant of the present application owns the following U.S. Patent Applications that were filed on Oct. 30, 2017, and which are each herein incorporated by reference in their respective entireties:

8

U.S. Provisional Patent Application Ser. No. 62/578,793, entitled SURGICAL INSTRUMENT WITH REMOTE RELEASE;

U.S. Provisional Patent Application Ser. No. 62/578,804, entitled SURGICAL INSTRUMENT HAVING DUAL ROTATABLE MEMBERS TO EFFECT DIFFERENT TYPES OF END EFFECTOR MOVEMENT;

U.S. Provisional Patent Application Ser. No. 62/578,817, entitled SURGICAL INSTRUMENT WITH ROTARY DRIVE SELECTIVELY ACTUATING MULTIPLE END EFFECTOR FUNCTIONS;

U.S. Provisional Patent Application Ser. No. 62/578,835, entitled SURGICAL INSTRUMENT WITH ROTARY DRIVE SELECTIVELY ACTUATING MULTIPLE END EFFECTOR FUNCTIONS;

U.S. Provisional Patent Application Ser. No. 62/578,844, entitled SURGICAL INSTRUMENT WITH MODULAR POWER SOURCES; and U.S. Provisional Patent Application Ser. No. 62/578,855, entitled SURGICAL INSTRUMENT WITH SENSOR AND/OR CONTROL SYSTEMS.

Applicant of the present application owns the following U.S. Provisional Patent Applications, filed on Dec. 28, 2017, the disclosure of each of which is herein incorporated by reference in its entirety:

U.S. Provisional Patent Application Ser. No. 62/611,341, entitled INTERACTIVE SURGICAL PLATFORM;

U.S. Provisional Patent Application Ser. No. 62/611,340, entitled CLOUD-BASED MEDICAL ANALYTICS; and U.S. Provisional Patent Application Ser. No. 62/611,339, entitled ROBOT ASSISTED SURGICAL PLATFORM.

Applicant of the present application owns the following U.S. Provisional Patent Applications, filed on Mar. 28, 2018, each of which is herein incorporated by reference in its entirety:

U.S. Provisional Patent Application Ser. No. 62/649,302, entitled INTERACTIVE SURGICAL SYSTEMS WITH ENCRYPTED COMMUNICATION CAPABILITIES;

U.S. Provisional Patent Application Ser. No. 62/649,294, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. Patent Applications, filed on Mar. 29, 2018, each of which is herein incorporated by reference in its entirety:

U.S. patent application Ser. No. 15/940,641, entitled INTERACTIVE SURGICAL SYSTEMS WITH ENCRYPTED COMMUNICATION CAPABILITIES;

U.S. patent application Ser. No. 15/940,648, entitled INTERACTIVE SURGICAL SYSTEMS WITH CONDITION HANDLING OF DEVICES AND DATA CAPABILITIES;

U.S. patent application Ser. No. 15/940,656, entitled SURGICAL HUB COORDINATION OF CONTROL AND COMMUNICATION OF OPERATING ROOM DEVICES;

U.S. patent application Ser. No. 15/940,666, entitled SPATIAL AWARENESS OF SURGICAL HUBS IN OPERATING ROOMS;

U.S. patent application Ser. No. 15/940,670, entitled COOPERATIVE UTILIZATION OF DATA DERIVED FROM SECONDARY SOURCES BY INTELLIGENT SURGICAL HUBS;

U.S. patent application Ser. No. 15/940,677, entitled SURGICAL HUB CONTROL ARRANGEMENTS;

U.S. patent application Ser. No. 15/940,632, entitled DATA STRIPPING METHOD TO INTERROGATE PATIENT RECORDS AND CREATE ANONYMIZED RECORD;

U.S. patent application Ser. No. 15/940,640, entitled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS;

U.S. patent application Ser. No. 15/940,645, entitled SELF DESCRIBING DATA PACKETS GENERATED AT AN ISSUING INSTRUMENT;

U.S. patent application Ser. No. 15/940,649, entitled DATA PAIRING TO INTERCONNECT A DEVICE MEASURED PARAMETER WITH AN OUTCOME;

U.S. patent application Ser. No. 15/940,654, entitled SURGICAL HUB SITUATIONAL AWARENESS;

U.S. patent application Ser. No. 15/940,663, entitled SURGICAL SYSTEM DISTRIBUTED PROCESSING;

U.S. patent application Ser. No. 15/940,668, entitled AGGREGATION AND REPORTING OF SURGICAL HUB DATA;

U.S. patent application Ser. No. 15/940,671, entitled SURGICAL HUB SPATIAL AWARENESS TO DETERMINE DEVICES IN OPERATING THEATER;

U.S. patent application Ser. No. 15/940,686, entitled DISPLAY OF ALIGNMENT OF STAPLE CARTRIDGE TO PRIOR LINEAR STAPLE LINE;

U.S. patent application Ser. No. 15/940,700, entitled STERILE FIELD INTERACTIVE CONTROL DISPLAYS;

U.S. patent application Ser. No. 15/940,629, entitled COMPUTER IMPLEMENTED INTERACTIVE SURGICAL SYSTEMS;

U.S. patent application Ser. No. 15/940,704, entitled USE OF LASER LIGHT AND RED-GREEN-BLUE COLORATION TO DETERMINE PROPERTIES OF BACK SCATTERED LIGHT;

U.S. patent application Ser. No. 15/940,722, entitled CHARACTERIZATION OF TISSUE IRREGULARITIES THROUGH THE USE OF MONO-CHROMATIC LIGHT REFRACTIVITY; and U.S. patent application Ser. No. 15/940,742, entitled DUAL CMOS ARRAY IMAGING.

Applicant of the present application owns the following U.S. Patent Applications, filed on Mar. 29, 2018, each of which is herein incorporated by reference in its entirety:

U.S. patent application Ser. No. 15/940,636, entitled ADAPTIVE CONTROL PROGRAM UPDATES FOR SURGICAL DEVICES;

U.S. patent application Ser. No. 15/940,653, entitled ADAPTIVE CONTROL PROGRAM UPDATES FOR SURGICAL HUBS;

U.S. patent application Ser. No. 15/940,660, entitled CLOUD-BASED MEDICAL ANALYTICS FOR CUSTOMIZATION AND RECOMMENDATIONS TO A USER;

U.S. patent application Ser. No. 15/940,679, entitled CLOUD-BASED MEDICAL ANALYTICS FOR LINKING OF LOCAL USAGE TRENDS WITH THE RESOURCE ACQUISITION BEHAVIORS OF LARGER DATA SET;

U.S. patent application Ser. No. 15/940,694, entitled CLOUD-BASED MEDICAL ANALYTICS FOR MEDICAL FACILITY SEGMENTED INDIVIDUALIZATION OF INSTRUMENT FUNCTION;

U.S. patent application Ser. No. 15/940,634, entitled CLOUD-BASED MEDICAL ANALYTICS FOR SECURITY AND AUTHENTICATION TRENDS AND REACTIVE MEASURES;

U.S. patent application Ser. No. 15/940,706, entitled DATA HANDLING AND PRIORITIZATION IN A CLOUD ANALYTICS NETWORK; and U.S. patent application Ser. No. 15/940,675, entitled CLOUD INTERFACE FOR COUPLED SURGICAL DEVICES.

Applicant of the present application owns the following U.S. Patent Applications, filed on Mar. 29, 2018, each of which is herein incorporated by reference in its entirety:

U.S. patent application Ser. No. 15/940,627, entitled DRIVE ARRANGEMENTS FOR ROBOT-ASSISTED SURGICAL PLATFORMS;

U.S. patent application Ser. No. 15/940,637, entitled COMMUNICATION ARRANGEMENTS FOR ROBOT-ASSISTED SURGICAL PLATFORMS;

U.S. patent application Ser. No. 15/940,642, entitled CONTROLS FOR ROBOT-ASSISTED SURGICAL PLATFORMS;

U.S. patent application Ser. No. 15/940,676, entitled AUTOMATIC TOOL ADJUSTMENTS FOR ROBOT-ASSISTED SURGICAL PLATFORMS;

U.S. patent application Ser. No. 15/940,680, entitled CONTROLLERS FOR ROBOT-ASSISTED SURGICAL PLATFORMS;

U.S. patent application Ser. No. 15/940,683, entitled COOPERATIVE SURGICAL ACTIONS FOR ROBOT-ASSISTED SURGICAL PLATFORMS;

U.S. patent application Ser. No. 15/940,690, entitled DISPLAY ARRANGEMENTS FOR ROBOT-ASSISTED SURGICAL PLATFORMS; and U.S. patent application Ser. No. 15/940,711, entitled SENSING ARRANGEMENTS FOR ROBOT-ASSISTED SURGICAL PLATFORMS.

Applicant of the present application owns the following U.S. Provisional Patent Applications, filed on Mar. 30, 2018, each of which is herein incorporated by reference in its entirety:

U.S. Provisional Patent Application Ser. No. 62/650,887, entitled SURGICAL SYSTEMS WITH OPTIMIZED SENSING CAPABILITIES;

U.S. Provisional Patent Application Ser. No. 62/650,877, entitled SURGICAL SMOKE EVACUATION SENSING AND CONTROLS;

U.S. Provisional Patent Application Ser. No. 62/650,882, entitled SMOKE EVACUATION MODULE FOR INTERACTIVE SURGICAL PLATFORM; and U.S. Provisional Patent Application Ser. No. 62/650,898, entitled CAPACITIVE COUPLED RETURN PATH PAD WITH SEPARABLE ARRAY ELEMENTS.

Applicant of the present application owns the following U.S. Provisional Patent Application, filed on Apr. 19, 2018, which is herein incorporated by reference in its entirety:

U.S. Provisional Patent Application Ser. No. 62/659,900, entitled METHOD OF HUB COMMUNICATION.

Applicant of the present application owns the following U.S. Provisional Patent Applications, filed on Oct. 25, 2018, each of which is herein incorporated by reference in its entirety:

U.S. Provisional Patent Application Ser. No. 62/750,529, entitled METHOD FOR OPERATING A POWERED ARTICULATING MULTI-CLIP APPLIER;

U.S. Provisional Patent Application Ser. No. 62/750,539, entitled SURGICAL CLIP APPLIER; and U.S. Provisional Patent Application Ser. No. 62/750,555, entitled SURGICAL CLIP APPLIER.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises,"

"has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

Figure 2:
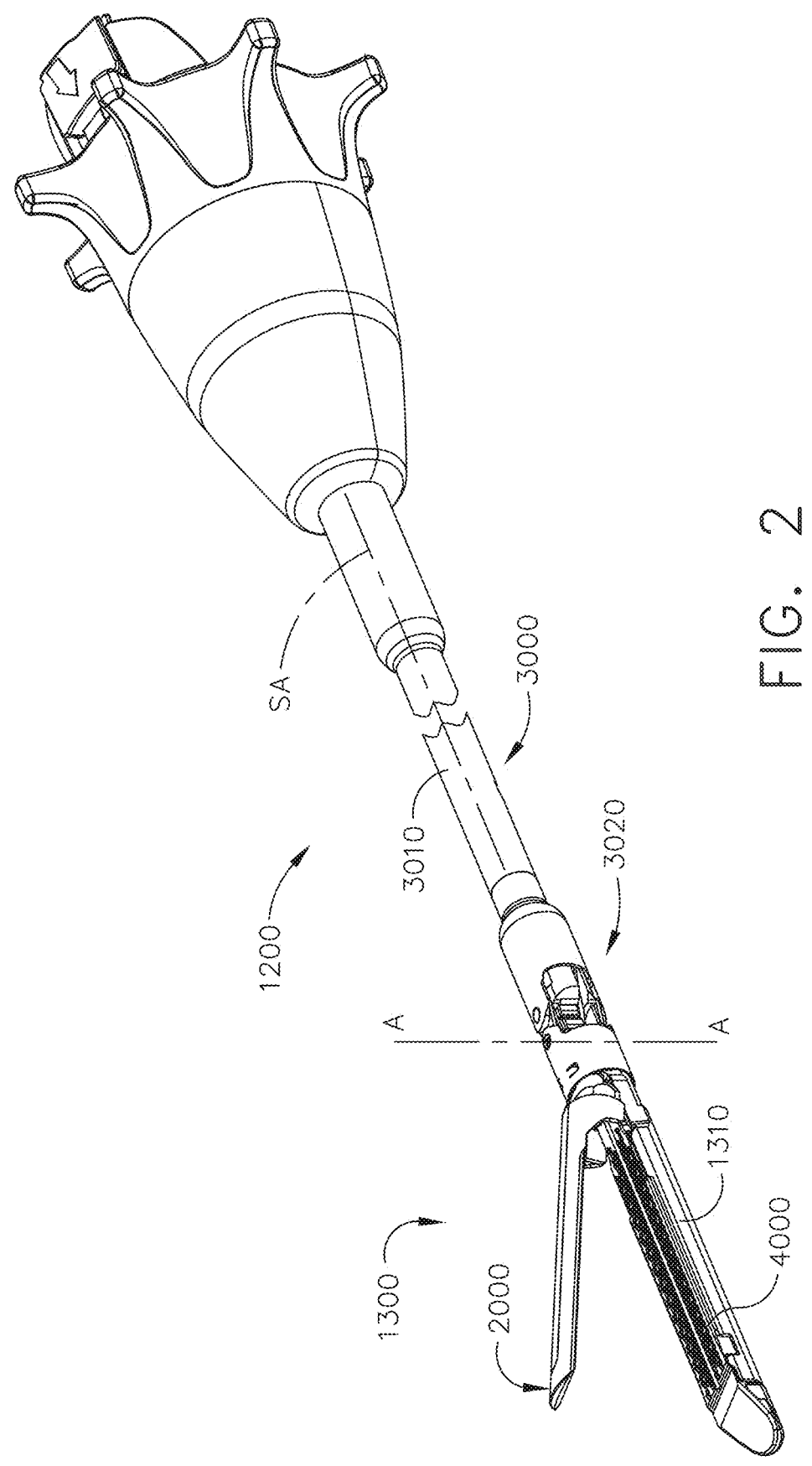
FIG. 2 is a perspective view of an interchangeable surgical shaft assembly of the powered surgical stapling system of FIG. 1.
Figure 3:
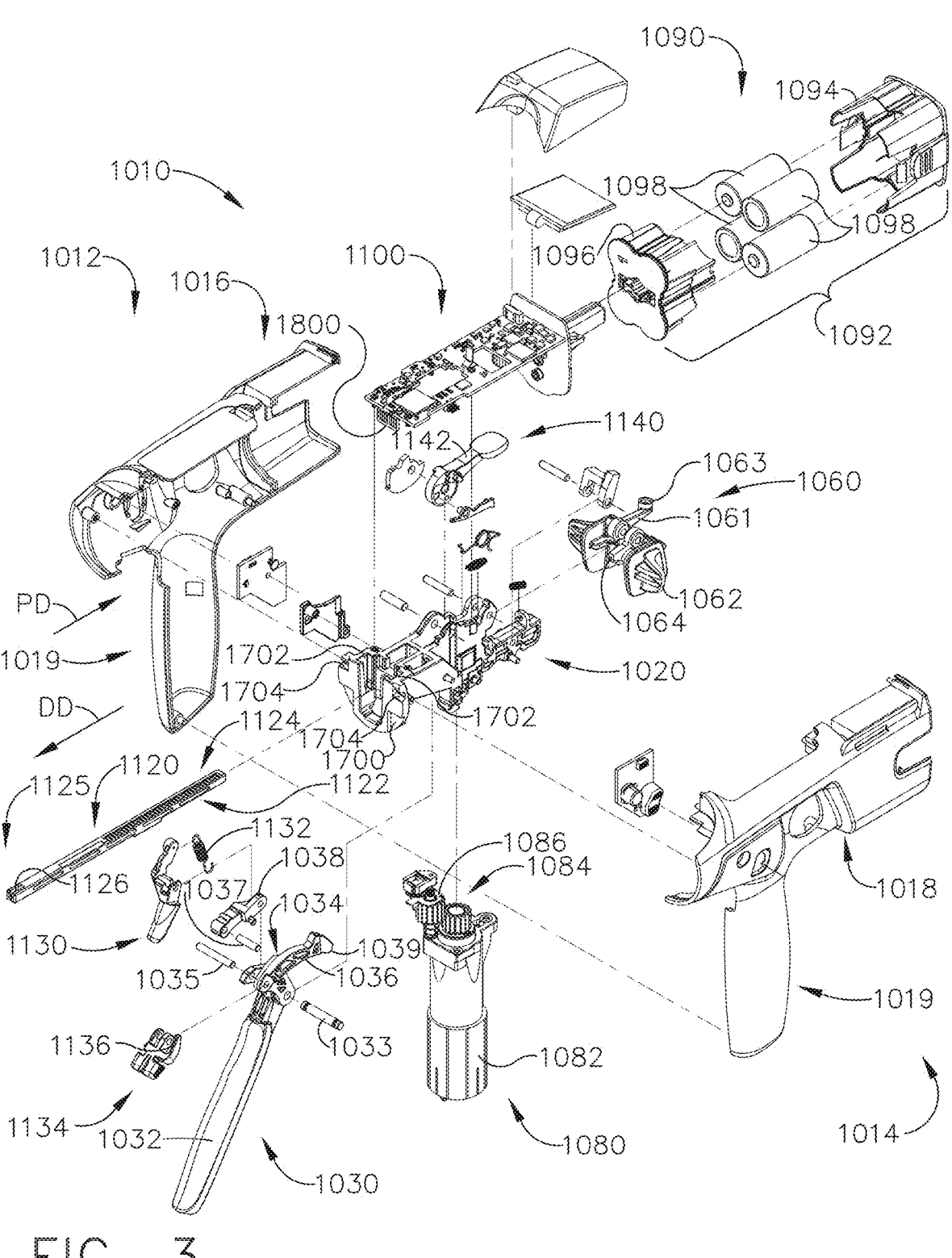
FIG. 3 is an exploded assembly view of portions of a handle assembly of the powered surgical stapling system of FIG. 1.

FIG. 1 illustrates the surgical instrument 1010 that includes an interchangeable shaft assembly 1200 operably coupled to a housing 1012. FIG. 2 illustrates the interchangeable shaft assembly 1200 detached from the housing 1012 or handle 1014. As can be seen in FIG. 3, the handle 1014 may comprise a pair of interconnectable handle housing segments 1016 and 1018 that may be interconnected by screws, snap features, adhesive, etc. In the illustrated arrangement, the handle housing segments 1016, 1018 cooperate to form a pistol grip portion 1019. FIGS. 1 and 3 depict a motor-driven surgical cutting and fastening instrument 1010 that may or may not be reused. In the illustrated embodiment, the housing 1012 comprises a handle 1014 that is configured to be grasped, manipulated, and actuated by the clinician. The housing 1012 is configured for operable attachment to an interchangeable shaft assembly 1200 that has a surgical end effector 1300 operably coupled thereto that is configured to perform one or more surgical tasks or procedures. As the present Detailed Description proceeds, it will be understood that the various forms of interchangeable shaft assemblies disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the interchangeable shaft assemblies disclosed herein and their respective equivalents. In addition, various components may be "housed" or contained in the housing or various components may be "associated with" a housing. In such instances, the components may not be contained within the housing or supported directly by the housing. The term "frame" may refer to a portion of a handheld surgical instrument. The term "frame"

may also represent a portion of a robotically controlled surgical instrument and/or a portion of the robotic system that may be used to operably control a surgical instrument. The interchangeable shaft assemblies disclosed herein may be employed with various robotic systems, instruments, components and methods disclosed in U.S. Pat. No. 9,072, 535, entitled SURGICAL STAPLING INSTRUMENTS WITH ROTATABLE STAPLE DEPLOYMENT ARRANGEMENTS, which is incorporated by reference herein in its entirety.

The housing 1012 depicted in FIG. 1 is shown in connection with an interchangeable shaft assembly 1200 (FIGS. 2, 4 and 5) that includes an end effector 1300 that comprises a surgical cutting and fastening device that is configured to operably support a surgical staple cartridge 4000 therein. The housing 1012 may be configured for use in connection with interchangeable shaft assemblies that include end effectors that are adapted to support different sizes and types of staple cartridges, have different shaft lengths, sizes, and types, etc. In addition, the housing 1012 may also be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. As will be discussed in further detail below, the handle 1014 operably supports a plurality of drive systems therein that are configured to generate and apply various control motions to corresponding portions of the interchangeable shaft assembly that is operably attached thereto.

Referring now to FIG. 3, the handle 1014 may further include a frame 1020 that operably supports a plurality of drive systems. For example, the frame 1020 can operably support a "first" or closure drive system, generally designated as 1030, which may be employed to apply closing and opening motions to the interchangeable shaft assembly 1200 that is operably attached or coupled thereto. In at least one form, the closure drive system 1030 may include an actuator in the form of a closure trigger 1032 that is pivotally supported by the frame 1020. As illustrated in FIG. 3, the closure trigger 1032 is pivotally coupled to the handle 1014 by a pin 1033. Such an arrangement enables the closure trigger 1032 to be manipulated by a clinician such that, when the clinician grips the pistol grip portion 1019 of the handle 1014, the closure trigger 1032 may be easily pivoted from a starting or "unactuated" position to an "actuated" position and, more particularly, to a fully compressed or fully actuated position. The closure trigger 1032 may be biased into the unactuated position by a spring or other biasing arrangement. In various forms, the closure drive system 1030 further includes a closure linkage assembly 1034 that is pivotally coupled to the closure trigger 1032. As can be seen in FIG. 3, the closure linkage assembly 1034 may include a first closure link 1036 and a second closure link 1038 that are pivotally coupled to the closure trigger 1032 by a pin 1035. The second closure link 1038 may also be referred to herein as an "attachment member" and include a transverse attachment pin 1037.

Still referring to FIG. 3, it can be observed that the first closure link 1036 may have a locking wall or end 1039 thereon that is configured to cooperate with a closure release assembly 1060 that is pivotally coupled to the frame 1020. In at least one form, the closure release assembly 1060 may comprise a release button assembly 1062 that has a distally protruding locking pawl 1064 formed thereon. The release button assembly 1062 may be pivoted in a counterclockwise direction by a release spring (not shown). As the clinician depresses the closure trigger 1032 from its unactuated position toward the pistol grip portion 1019 of the handle 1014, the first closure link 1036 pivots upward to a point wherein the locking pawl 1064 drops into retaining engagement with the locking wall 1039 on the first closure link 1036 thereby preventing the closure trigger 1032 from returning to the unactuated position. Thus, the closure release assembly 1060 serves to lock the closure trigger 1032 in the fully actuated position. When the clinician desires to unlock the closure trigger 1032 to permit it to be biased to the unactuated position, the clinician simply pivots the release button assembly 1062 such that the locking pawl 1064 is moved out of engagement with the locking wall 1039 on the first closure link 1036. When the locking pawl 1064 has been moved out of engagement with the first closure link 1036, the closure trigger 1032 may pivot back to the unactuated position. Other closure trigger locking and release arrangements may also be employed.

An arm 1061 may extend from the release button assembly 1062. A magnetic element 1063, such as a permanent magnet, for example, may be mounted to the arm 1061. When the release button assembly 1062 is rotated from its first position to its second position, the magnetic element 1063 can move toward a circuit board 1100. The circuit board 1100 can include at least one sensor that is configured to detect the movement of the magnetic element 1063. In at least one embodiment, for example, a Hall Effect sensor can be mounted to the bottom surface of the circuit board 1100. The Hall Effect sensor can be configured to detect changes in a magnetic field surrounding the Hall Effect sensor caused by the movement of the magnetic element 1063. The Hall Effect sensor can be in signal communication with a microcontroller, for example, which can determine whether the release button assembly 1062 is in its first position, which is associated with the unactuated position of the closure trigger 1032 and the open configuration of the end effector, its second position, which is associated with the actuated position of the closure trigger 1032 and the closed configuration of the end effector, and/or any position between the first position and the second position.

In at least one form, the handle 1014 and the frame 1020 may operably support another drive system referred to herein as a firing drive system 1080 that is configured to apply firing motions to corresponding portions of the interchangeable shaft assembly attached thereto. The firing drive system 1080 may also be referred to herein as a "second drive system". The firing drive system 1080 may employ an electric motor 1082 that is located in the pistol grip portion 1019 of the handle 1014. In various forms, the motor 1082 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 1082 may be powered by a power source 1090 that in one form may comprise a removable power pack 1092. As can be seen in FIG. 3, for example, the power pack 1092 may comprise a proximal housing portion 1094 that is configured for attachment to a distal housing portion 1096. The proximal housing portion 1094 and the distal housing portion 1096 are configured to operably support a plurality of batteries 1098 therein. Batteries 1098 may each comprise, for example, a Lithium Ion ("LI") or other suitable battery. The distal housing portion 1096 is configured for removable operable attachment to the circuit board 1100 which is also operably coupled to the motor 1082. A number of batteries 1098 may be connected in series may be used as the power source for the surgical instrument 1010. In addition, the power source 1090 may be replaceable and/or rechargeable.

As outlined above with respect to other various forms, the electric motor 1082 can include a rotatable shaft (not shown) that operably interfaces with a gear reducer assembly 1084 that is mounted in meshing engagement with a with a set, or rack, of drive teeth 1122 on a longitudinally-movable drive member 1120. In use, a voltage polarity provided by the power source 1090 can operate the electric motor 1082 in a clockwise direction wherein the voltage polarity applied to the electric motor by the battery can be reversed in order to operate the electric motor 1082 in a counter-clockwise direction. When the electric motor 1082 is rotated in one direction, the drive member 1120 will be axially driven in the distal direction "DD". When the motor 1082 is driven in the opposite rotary direction, the drive member 1120 will be axially driven in a proximal direction "PD". The handle 1014 can include a switch which can be configured to reverse the polarity applied to the electric motor 1082 by the power source 1090. As with the other forms described herein, the handle 1014 can also include a sensor that is configured to detect the position of the drive member 1120 and/or the direction in which the drive member 1120 is being moved.

Actuation of the motor 1082 can be controlled by a firing trigger 1130 that is pivotally supported on the handle 1014. The firing trigger 1130 may be pivoted between an unactuated position and an actuated position. The firing trigger 1130 may be biased into the unactuated position by a spring 1132 or other biasing arrangement such that, when the clinician releases the firing trigger 1130, the firing trigger 1130 may be pivoted or otherwise returned to the unactuated position by the spring 1132 or biasing arrangement. In at least one form, the firing trigger 1130 can be positioned "outboard" of the closure trigger 1032 as was discussed above. In at least one form, a firing trigger safety button 1134 may be pivotally mounted to the closure trigger 1032 by the pin 1035. The safety button 1134 may be positioned between the firing trigger 1130 and the closure trigger 1032 and have a pivot arm 1136 protruding therefrom. See FIG. 3. When the closure trigger 1032 is in the unactuated position, the safety button 1134 is contained in the handle 1014 where the clinician cannot readily access it and move it between a safety position preventing actuation of the firing trigger 1130 and a firing position wherein the firing trigger 1130 may be fired. As the clinician depresses the closure trigger 1032, the safety button 1134 and the firing trigger 1130 pivot down wherein they can then be manipulated by the clinician.

As indicated above, in at least one form, the longitudinally movable drive member 1120 has a rack of teeth 1122 formed thereon for meshing engagement with a corresponding drive gear 1086 of the gear reducer assembly 1084. At least one form also includes a manually-actuatable "bailout" assembly 1140 that is configured to enable the clinician to manually retract the longitudinally movable drive member 1120 should the motor 1082 become disabled. The bailout assembly 1140 may include a lever or bailout handle assembly 1142 that is configured to be manually pivoted into ratcheting engagement with teeth 1124 also provided in the drive member 1120. Thus, the clinician can manually retract the drive member 1120 by using the bailout handle assembly 1142 to ratchet the drive member 1120 in the proximal direction "PD". U.S. Pat. No. 8,608,045, entitled POWERED SURGICAL CUTTING AND STAPLING APPARATUS WITH MANUALLY RETRACTABLE FIRING SYSTEM, discloses bailout arrangements and other components, arrangements and systems that may also be employed with the various instruments disclosed herein. U.S. Pat. No. 8,608,045, entitled POWERED SURGICAL CUTTING AND STAPLING APPARATUS WITH MANUALLY RETRACTABLE FIRING SYSTEM is hereby incorporated by reference herein in its entirety.

Figure 4:
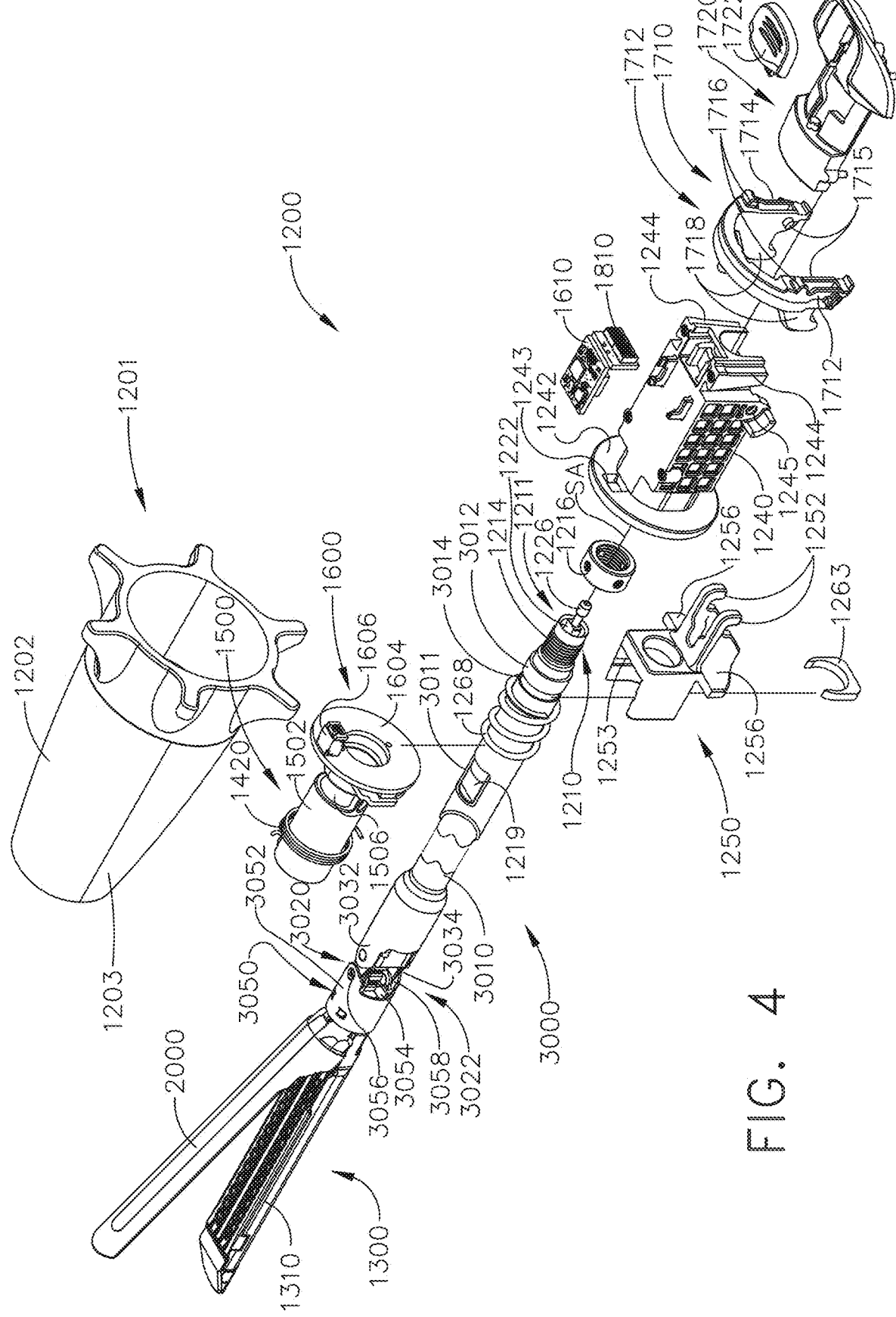
FIG. 4 is an exploded assembly view of the interchangeable surgical shaft assembly of FIG. 2.
Figure 5:
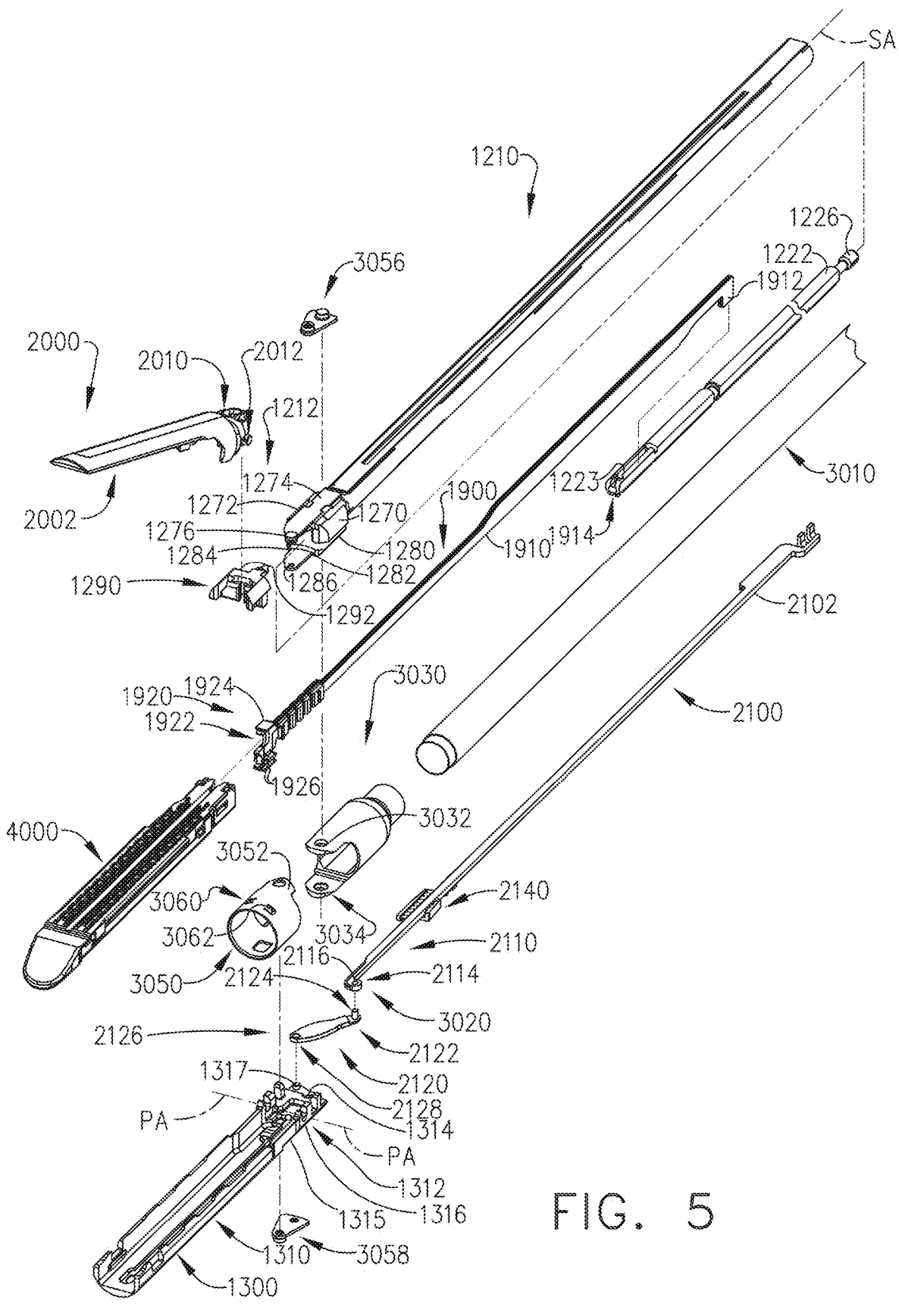
FIG. 5 is another partial exploded assembly view of a portion of the interchangeable surgical shaft assembly of FIG. 4.

Referring to FIGS. 2 and 5, the surgical end effector 1300 comprises an elongate channel 1310 that is configured to operably support the staple cartridge 4000 therein. The end effector 1300 may further include an anvil 2000 that is pivotally supported relative to the elongate channel 1310. The interchangeable shaft assembly 1200 may further include an articulation joint 3020 and an articulation lock 2140 which can be configured to releasably hold the end effector 1300 in a desired position relative to a shaft axis SA. Examples of various features of at least one form of the end effector 1300, the articulation joint 3020 and articulation locks may be found in U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541. The entire disclosure of U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541, is hereby incorporated by reference herein. As can be seen in FIG. 4, the interchangeable shaft assembly 1200 can further include a proximal housing or nozzle 1201 comprised of nozzle portions 1202 and 1203.

The interchangeable shaft assembly 1200 can further include a closure system or closure member assembly 3000 which can be utilized to close and/or open the anvil 2000 of the end effector 1300. The shaft assembly 1200 can include a spine 1210 that is configured to, one, slideably support a firing member therein and, two, slideably support the closure member assembly 3000 which extends around the spine 1210. As can be seen in FIG. 5, a distal end 1212 of spine 1210 terminates in an upper lug mount feature 1270 and in a lower lug mount feature 1280. The upper lug mount feature 1270 is formed with a lug slot 1272 therein that is adapted to mountingly support an upper mounting link 1274 therein. Similarly, the lower lug mount feature 1280 is formed with a lug slot 1282 therein that is adapted to mountingly support a lower mounting link 1284 therein. The upper mounting link 1274 includes a pivot socket 1276 therein that is adapted to rotatably receive therein a pivot pin 1292 that is formed on a channel cap or anvil retainer 1290 that is attached to a proximal end portion 1312 of the elongate channel 1310. The lower mounting link 1284 includes lower pivot pin 1286 that adapted to be received within a pivot hole 1314 formed in the proximal end portion 1312 of the elongate channel 1310. See FIG. 5. The lower pivot pin 1286 is vertically aligned with the pivot socket 1276 to define an articulation axis AA about which the surgical end effector 1300 may articulate relative to the shaft axis SA. See FIG. 2.

In the illustrated example, the surgical end effector 1300 is selectively articulatable about the articulation axis AA by an articulation system 2100. In one form, the articulation system 2100 includes proximal articulation driver 2102 that is pivotally coupled to an articulation link 2120. As can be seen in FIG. 5, an offset attachment lug 2114 is formed on a distal end 2110 of the proximal articulation driver 2102. A pivot hole 2116 is formed in the offset attachment lug 2114 and is configured to pivotally receive therein a proximal link pin 2124 formed on the proximal end 2122 of the articulation link 2120. A distal end 2126 of the articulation link 2120 includes a pivot hole 2128 that is configured to pivotally receive therein a channel pin 1317 formed on the proximal end portion 1312 of the elongate channel 1310. Thus, axial movement of proximal articulation driver 2102 will thereby apply articulation motions to the elongate channel 1310 to thereby cause the surgical end effector 1300 to articulate about the articulation axis AA relative to the spine 1210. Further details concerning the construction and operation of the articulation system 2100 may be found in U.S. patent application Ser. No. 15/635,631, filed Jun. 28, 2017, entitled SURGICAL INSTRUMENT WITH AXIALLY MOVABLE CLOSURE MEMBER, now U.S. Patent Application Publication No. 2019/0000464. The entire disclosure of U.S. patent application Ser. No. 15/635,631, filed Jun. 28, 2017, entitled SURGICAL INSTRUMENT WITH AXIALLY MOVABLE CLOSURE MEMBER, now U.S. Patent Application Publication No. 2019/0000464 is hereby incorporated by reference herein. In various circumstances, the proximal articulation driver 2102 can be held in position by an articulation lock 2140 when the proximal articulation driver 2102 is not being moved in the proximal or distal directions. Additional details regarding an example of an articulation lock 2140 may be found in U.S. patent application Ser. No. 15/635,631, now U.S. Patent Application Publication No. 2019/0000464, as well as in other references incorporated by reference herein.

In various circumstances, the spine 1210 can comprise a proximal end 1211 which is rotatably supported in a chassis 1240. In one arrangement, for example, the proximal end 1211 of the spine 1210 has a thread 1214 formed thereon for threaded attachment to a spine bearing 1216 configured to be supported within the chassis 1240. See FIG. 4. Such an arrangement facilitates the rotatable attachment of the spine 1210 to the chassis 1240 such that the spine 1210 may be selectively rotated about a shaft axis SA relative to the chassis 1240.

Referring primarily to FIG. 4, the interchangeable shaft assembly 1200 includes a closure shuttle 1250 that is slideably supported within the chassis 1240 such that it may be axially moved relative thereto. The closure shuttle 1250 includes a pair of proximally-protruding hooks 1252 that are configured for attachment to the attachment pin 1037 (FIG. 3) that is attached to the second closure link 1038, as will be discussed in further detail below. In at least one example, the closure member assembly 3000 comprises a proximal closure member segment 3010 that has a proximal end 3012 that is coupled to the closure shuttle 1250 for relative rotation thereto. A U-shaped connector 1263 is inserted into an annular slot 3014 in the proximal end 3012 of the proximal closure member segment 3010 and is retained within vertical slots 1253 in the closure shuttle 1250. Such an arrangement serves to attach the proximal closure member segment 3010 to the closure shuttle 1250 for axial travel therewith while enabling the proximal closure member segment 3010 to rotate relative to the closure shuttle 1250 about the shaft axis SA. A closure spring 1268 is journaled on the proximal closure member segment 3010 and serves to bias the proximal closure member segment 3010 in the proximal direction "PD" which can serve to pivot the closure trigger 1032 into the unactuated position when the shaft assembly is operably coupled to the handle 1014.

In at least one form, the interchangeable shaft assembly 1200 may further include an articulation joint 3020. Other interchangeable shaft assemblies, however, may not be capable of articulation. As can be seen in FIG. 5, for example, a distal closure member or distal closure tube segment 3030 is coupled to the distal end of the proximal closure member segment 3010. The articulation joint 3020 includes a double pivot closure sleeve assembly 3022. According to various forms, the double pivot closure sleeve assembly 3022 includes an end effector closure tube 3050 having upper and lower distally projecting tangs 3052, 3054. An upper double pivot link 3056 includes upwardly projecting distal and proximal pivot pins that engage respectively an upper distal pin hole in the upper proximally projecting tang 3052 and an upper proximal pin hole in an upper distally projecting tang 3032 on the distal closure tube segment 3030. A lower double pivot link 3058 includes upwardly projecting distal and proximal pivot pins that engage respectively a lower distal pin hole in the lower proximally projecting tang 3054 and a lower proximal pin hole in the lower distally projecting tang 3034. See FIGS. 4 and 5. As will be discussed in further detail below, the closure member assembly 3000 is translated distally (direction "DD") to close the anvil 2000, for example, in response to the actuation of the closure trigger 1032. The anvil 2000 is opened by proximally translating the closure member assembly 3000 which causes the end effector closure tube 3050 to interact with the anvil 2000 and pivot it to an open position.

The interchangeable shaft assembly 1200 further includes a firing member 1900 that is supported for axial travel within the spine 1210. The firing member 1900 includes an intermediate firing shaft portion 1222 that is configured for attachment to a distal cutting portion or knife bar 1910. The intermediate firing shaft portion 1222 may include a longitudinal slot 1223 in the distal end thereof which can be configured to receive a tab 1912 on the proximal end of the distal knife bar 1910. The longitudinal slot 1223 and the proximal end tab 1912 can be sized and configured to permit relative movement therebetween and can comprise a slip joint 1914. The slip joint 1914 can permit the intermediate firing shaft portion 1222 of the firing member 1900 to be moved to articulate the end effector 1300 without moving, or at least substantially moving, the knife bar 1910. Once the end effector 1300 has been suitably oriented, the intermediate firing shaft portion 1222 can be advanced distally until a proximal sidewall of the longitudinal slot 1223 comes into contact with the tab 1912 in order to advance the knife bar 1910 and fire the staple cartridge 4000 positioned within the channel 1310. The knife bar 1910 includes a knife portion 1920 that includes a blade or tissue cutting edge 1922 and includes an upper anvil engagement tab 1924 and lower channel engagement tabs 1926. Various firing member configurations and operations are disclosed in various other references incorporated herein by reference.

As can be seen in FIG. 4, the shaft assembly 1200 further includes a switch drum 1500 that is rotatably received on proximal closure member segment 3010. The switch drum 1500 comprises a hollow shaft segment 1502 that has a shaft boss formed thereon for receive an outwardly protruding actuation pin therein. In various circumstances, the actuation pin extends through a longitudinal slot provided in the lock sleeve to facilitate axial movement of the lock sleeve when it is engaged with the articulation driver. A rotary torsion spring 1420 is configured to engage the boss on the switch drum 1500 and a portion of the nozzle housing 1203 to apply a biasing force to the switch drum 1500. The switch drum 1500 can further comprise at least partially circumferential openings 1506 defined therein which can be configured to receive circumferential mounts extending from the nozzle portions 1202, 1203 and permit relative rotation, but not translation, between the switch drum 1500 and the nozzle

1201. The mounts also extend through openings 3011 in the proximal closure member segment 3010 to be seated in recesses 1219 in the spine 1210. Rotation of the switch drum 1500 about the shaft axis SA will ultimately result in the rotation of the actuation pin and the lock sleeve between its engaged and disengaged positions. In one arrangement, the rotation of the switch drum 1500 may be linked to the axial advancement of the closure tube or closure member. Thus, in essence, actuation of the closure system may operably engage and disengage the articulation drive system with the firing drive system in the various manners described in further detail in U.S. patent application Ser. No. 13/803,086, now U.S. Patent Application Publication No. 2014/0263541, entitled ARTICULATABLE SURGICAL INSTRUMENT COMPRISING AN ARTICULATION LOCK and U.S. Pat. No. 9,913,642, entitled SURGICAL INSTRUMENT COMPRISING A SENSOR SYSTEM, the entire disclosures of each being hereby incorporated by reference herein. When the closure member segment 3010 is in its proximal-most position corresponding to a "jaws open" position, the closure member segment 3010 will have positioned the switch drum 1500 so as to link the articulation system with the firing drive system. When the closure tube has been moved to its distal position corresponding to a "jaws closed" position, the closure tube has rotated the switch drum 1500 to a position wherein the articulation system is delinked from the firing drive system.

As also illustrated in FIG. 4, the shaft assembly 1200 can comprise a slip ring assembly 1600 which can be configured to conduct electrical power to and/or from the end effector 1300 and/or communicate signals to and/or from the end effector 1300, for example. The slip ring assembly 1600 can comprise a proximal connector flange 1604 that is mounted to a chassis flange 1242 that extends from the chassis 1240 and a distal connector flange that is positioned within a slot defined in the shaft housings. The proximal connector flange 1604 can comprise a first face and the distal connector flange can comprise a second face which is positioned adjacent to and movable relative to the first face. The distal connector flange can rotate relative to the proximal connector flange 1604 about the shaft axis SA. The proximal connector flange 1604 can comprise a plurality of concentric, or at least substantially concentric, conductors defined in the first face thereof. A connector can be mounted on the proximal side of the connector flange and may have a plurality of contacts wherein each contact corresponds to and is in electrical contact with one of the conductors. Such an arrangement permits relative rotation between the proximal connector flange 1604 and the distal connector flange while maintaining electrical contact therebetween. The proximal connector flange 1604 can include an electrical connector 1606 which can place the conductors in signal communication with a shaft circuit board 1610 mounted to the shaft chassis 1240, for example. In at least one instance, a wiring harness comprising a plurality of conductors can extend between the electrical connector 1606 and the shaft circuit board 1610. The electrical connector 1606 may extend proximally through a connector opening 1243 defined in the chassis flange 1242. See FIG. 4. Further details regarding slip ring assembly 1600 may be found in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552, and U.S. Pat.

No. 9,345,481, entitled STAPLE CARTRIDGE TISSUE THICKNESS SENSOR SYSTEM, for example. U.S. patent application Ser. No. 13/803,086, now U.S. Patent Application Publication No. 2014/0263541, U.S. patent application Ser. No. 13/800,067, now U.S. Patent Application Publication No. 2014/0263552, and U.S. Pat. No. 9,345,481, entitled STAPLE CARTRIDGE TISSUE THICKNESS SENSOR SYSTEM, are each hereby incorporated by reference herein in their respective entireties.

As discussed above, the shaft assembly 1200 can include a proximal portion which is fixably mounted to the handle 1014 and a distal portion which is rotatable about a longitudinal axis. The rotatable distal shaft portion can be rotated relative to the proximal portion about the slip ring assembly 1600, as discussed above. The distal connector flange of the slip ring assembly 1600 can be positioned within the rotatable distal shaft portion. Moreover, further to the above, the switch drum 1500 can also be positioned within the rotatable distal shaft portion. When the rotatable distal shaft portion is rotated, the distal connector flange and the switch drum 1500 can be rotated synchronously with one another. In addition, the switch drum 1500 can be rotated between a first position and a second position relative to the distal connector flange. When the switch drum 1500 is in its first position, the articulation drive system may be operably disengaged from the firing drive system and, thus, the operation of the firing drive system may not articulate the end effector 1300 of the shaft assembly 1200. When the switch drum 1500 is in its second position, the articulation drive system may be operably engaged with the firing drive system and, thus, the operation of the firing drive system may articulate the end effector 1300 of the shaft assembly 1200. When the switch drum 1500 is moved between its first position and its second position, the switch drum 1500 is moved relative to distal connector flange. In various instances, the shaft assembly 1200 can comprise at least one sensor configured to detect the position of the switch drum 1500.

Referring again to FIG. 4, the chassis 1240 includes at least one, and preferably two, tapered attachment portions 1244 formed thereon that are adapted to be received within corresponding dovetail slots 1702 formed within a distal attachment flange portion 1700 of the frame 1020. See FIG. 3. Each dovetail slot 1702 may be tapered or, stated another way, be somewhat V-shaped to seatingly receive the attachment portions 1244 therein. As can be further seen in FIG. 4, a shaft attachment lug 1226 is formed on the proximal end of the intermediate firing shaft portion 1222. As will be discussed in further detail below, when the interchangeable shaft assembly 1200 is coupled to the handle 1014, the shaft attachment lug 1226 is received in a firing shaft attachment cradle 1126 formed in a distal end 1125 of the longitudinal drive member 1120. See FIG. 3.

Various shaft assembly embodiments employ a latch system 1710 for removably coupling the shaft assembly 1200 to the housing 1012 and, more specifically, to the frame 1020. As can be seen in FIG. 4, the latch system 1710 includes a lock member or lock yoke 1712 that is movably coupled to the chassis 1240. In the illustrated embodiment, for example, the lock yoke 1712 has a U-shape with two spaced downwardly extending legs 1714. The legs 1714 each have a pivot lug 1715 formed thereon that are adapted to be received in corresponding holes 1245 formed in the chassis 1240. Such an arrangement facilitates the pivotal attachment of the lock yoke 1712 to the chassis 1240. The lock yoke 1712 may include two proximally-protruding lock lugs 1716 that are configured for releasable engagement with corresponding lock detents or grooves 1704 in the distal attachment flange portion 1700 of the frame 1020. See FIG. 3. In various forms, the lock yoke 1712 is biased in the proximal direction by a spring or biasing member. Actuation of the lock yoke 1712 may be accomplished by a latch button 1722 that is slideably mounted on a latch actuator assembly 1720 that is mounted to the chassis 1240. The latch button 1722 may be biased in a proximal direction relative to the lock yoke 1712. As will be discussed in further detail below, the lock yoke 1712 may be moved to an unlocked position by biasing the latch button in the distal direction which also causes the lock yoke 1712 to pivot out of retaining engagement with the distal attachment flange portion 1700 of the frame 1020. When the lock yoke 1712 is in "retaining engagement" with the distal attachment flange portion 1700 of the frame 1020, the lock lugs 1716 are retainingly seated within the corresponding lock detents or grooves 1704 in the distal attachment flange portion 1700.

When employing an interchangeable shaft assembly that includes an end effector of the type described herein that is adapted to cut and fasten tissue, as well as other types of end effectors, it may be desirable to prevent the inadvertent detachment of the interchangeable shaft assembly from the housing during the actuation of the end effector. For example, in use the clinician may actuate the closure trigger 1032 to grasp and manipulate the target tissue into a desired position. Once the target tissue is positioned within the end effector 1300 in a desired orientation, the clinician may then fully actuate the closure trigger 1032 to close the anvil 2000 and clamp the target tissue in position for cutting and stapling. In that instance, the first drive system 1030 has been fully actuated. After the target tissue has been clamped in the end effector 1300, it may be desirable to prevent the inadvertent detachment of the shaft assembly 1200 from the housing 1012. The latch system 1710 is configured to prevent such an inadvertent detachment.

As can be seen in FIG. 4, the lock yoke 1712 includes at least one and preferably two lock hooks 1718 that are adapted to contact corresponding lock lug portions 1256 that are formed on the closure shuttle 1250. When the closure shuttle 1250 is in an unactuated position (i.e., the first drive system 1030 is unactuated and the anvil 2000 is open), the lock yoke 1712 may be pivoted in a distal direction to unlock the interchangeable shaft assembly 1200 from the housing 1012. When in that position, the lock hooks 1718 do not contact the lock lug portions 1256 on the closure shuttle 1250. However, when the closure shuttle 1250 is moved to an actuated position (i.e., the first drive system 1030 is actuated and the anvil 2000 is in the closed position), the lock yoke 1712 is prevented from being pivoted to an unlocked position. Stated another way, if the clinician were to attempt to pivot the lock yoke 1712 to an unlocked position or, for example, the lock yoke 1712 was inadvertently bumped or contacted in a manner that might otherwise cause it to pivot distally, the lock hooks 1718 on the lock yoke 1712 will contact the lock lug portions 1256 on the closure shuttle 1250 and prevent movement of the lock yoke 1712 to an unlocked position.

Attachment of the interchangeable shaft assembly 1200 to the handle 1014 will now be described. To commence the coupling process, the clinician may position the chassis 1240 of the interchangeable shaft assembly 1200 above or adjacent to the distal attachment flange portion 1700 of the frame 1020 such that the tapered attachment portions 1244 formed on the chassis 1240 are aligned with the dovetail slots 1702 in the frame 1020. The clinician may then move the shaft assembly 1200 along an installation axis that is perpendicular to the shaft axis SA to seat the attachment portions 1244 in "operable engagement" with the corresponding dovetail receiving slots 1702. In doing so, the shaft attachment lug 1226 on the intermediate firing shaft portion 1222 will also be seated in the cradle 1126 in the longitudinally movable drive member 1120 and the portions of the pin 1037 on the second closure link 1038 will be seated in the corresponding hooks 1252 in the closure shuttle 1250. As used herein, the term "operable engagement" in the context of two components means that the two components are sufficiently engaged with each other so that upon application of an actuation motion thereto, the components may carry out their intended action, function, and/or procedure.

At least five systems of the interchangeable shaft assembly 1200 can be operably coupled with at least five corresponding systems of the handle 1014. A first system can comprise a frame system which couples and/or aligns the frame or spine of the shaft assembly 1200 with the frame 1020 of the handle 1014. Another system can comprise a closure drive system 1030 which can operably connect the closure trigger 1032 of the handle 1014 and the closure tube 1260 and the anvil 2000 of the shaft assembly 1200. As outlined above, the closure shuttle 1250 of the shaft assembly 1200 can be engaged with the pin 1037 on the second closure link 1038. Another system can comprise the firing drive system 1080 which can operably connect the firing trigger 1130 of the handle 1014 with the intermediate firing shaft portion 1222 of the shaft assembly 1200. As outlined above, the shaft attachment lug 1226 can be operably connected with the cradle 1126 of the longitudinal drive member 1120. Another system can comprise an electrical system which can signal to a controller in the handle 1014, such as a microcontroller, for example, that a shaft assembly, such as shaft assembly 1200, for example, has been operably engaged with the handle 1014 and/or, two, conduct power and/or communication signals between the shaft assembly 1200 and the handle 1014. For instance, the shaft assembly 1200 can include an electrical connector 1810 that is operably mounted to the shaft circuit board 1610. The electrical connector 1810 is configured for mating engagement with a corresponding electrical connector 1800 on the handle control board 1100. Further details regaining the circuitry and control systems may be found in U.S. patent application Ser. No. 13/803,086, now U.S. Patent Application Publication No. 2014/0263541, and U.S. patent application Ser. No. 14/226,142, now U.S. Pat. No. 9,913,642, the entire disclosures of which are incorporated by reference herein. The fifth system may consist of the latching system for releasably locking the shaft assembly 1200 to the handle 1014.

The anvil 2000 in the illustrated example includes an anvil body 2002 that terminates in an anvil mounting portion 2010. The anvil mounting portion 2010 is movably or pivotably supported on the elongate channel 1310 for selective pivotal travel relative thereto about a fixed anvil pivot axis PA that is transverse to the shaft axis SA. In the illustrated arrangement, a pivot member or anvil trunnion 2012 extends laterally out of each lateral side of the anvil mounting portion 2010 to be received in a corresponding trunnion cradle 1316 formed in the upstanding walls 1315 of the proximal end portion 1312 of the elongate channel 1310. The anvil trunnions 2012 are pivotally retained in their corresponding trunnion cradle 1316 by the channel cap or anvil retainer 1290. The channel cap or anvil retainer 1290 includes a pair of attachment lugs that are configured to be retainingly received within corresponding lug grooves or notches formed in the upstanding walls 1315 of the proximal end portion 1312 of the elongate channel 1310. See FIG. 5.

Still referring to FIG. 5, in at least one arrangement, the distal closure member or end effector closure tube 3050 employs two axially offset, proximal and distal positive jaw opening features 3060 and 3062. The positive jaw opening features 3060, 3062 are configured to interact with corresponding relieved areas and stepped portions formed on the anvil mounting portion 2010 as described in further detail in U.S. patent application Ser. No. 15/635,631, entitled SURGICAL INSTRUMENT WITH AXIALLY MOVABLE CLOSURE MEMBER, now U.S. Patent Application Publication No. 2019/0000464, the entire disclosure which is incorporated by reference herein. Other jaw opening arrangements may be employed.

Figure 6:
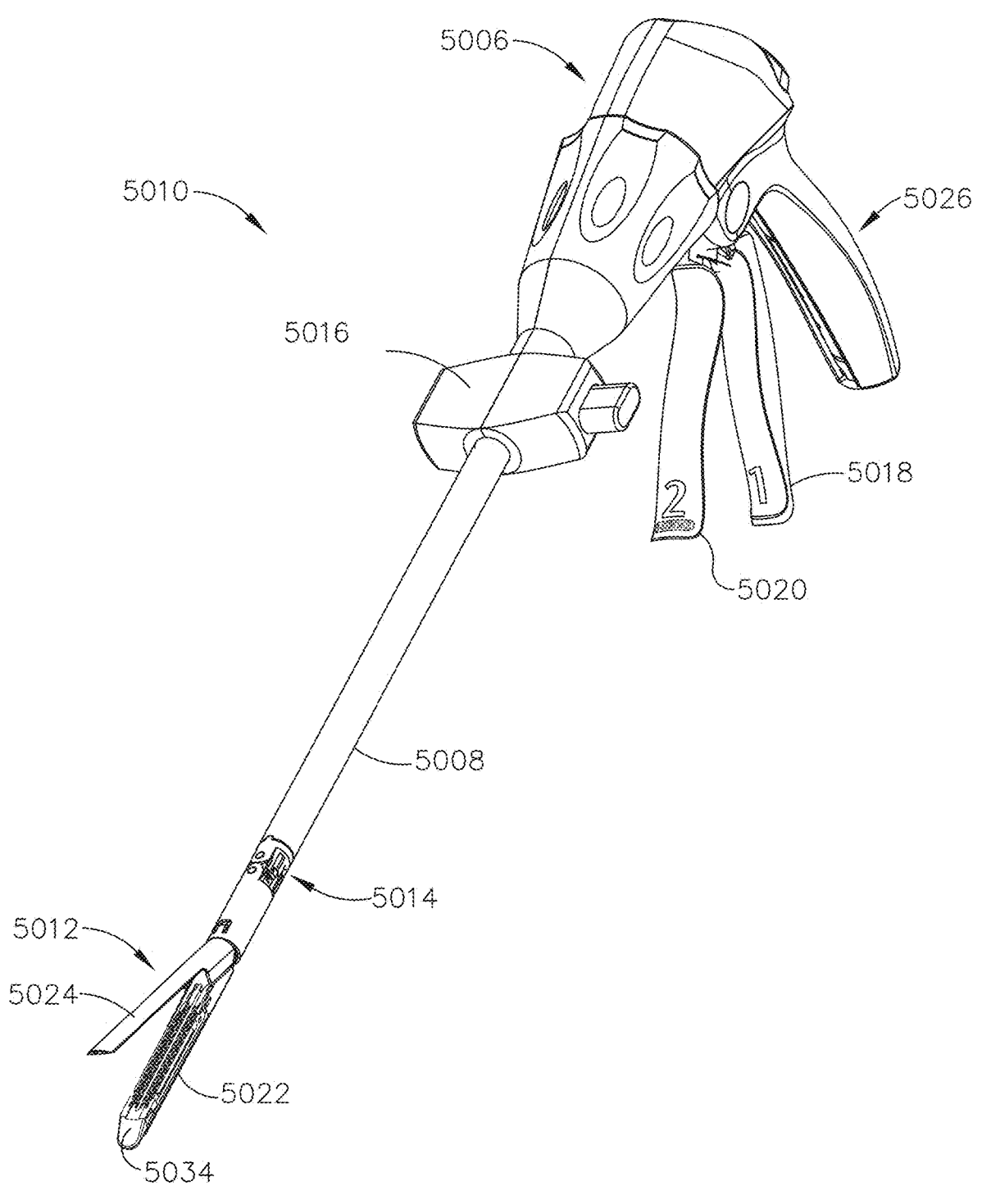
FIG. 6 is a perspective view of another powered surgical stapling system.
Figure 7:
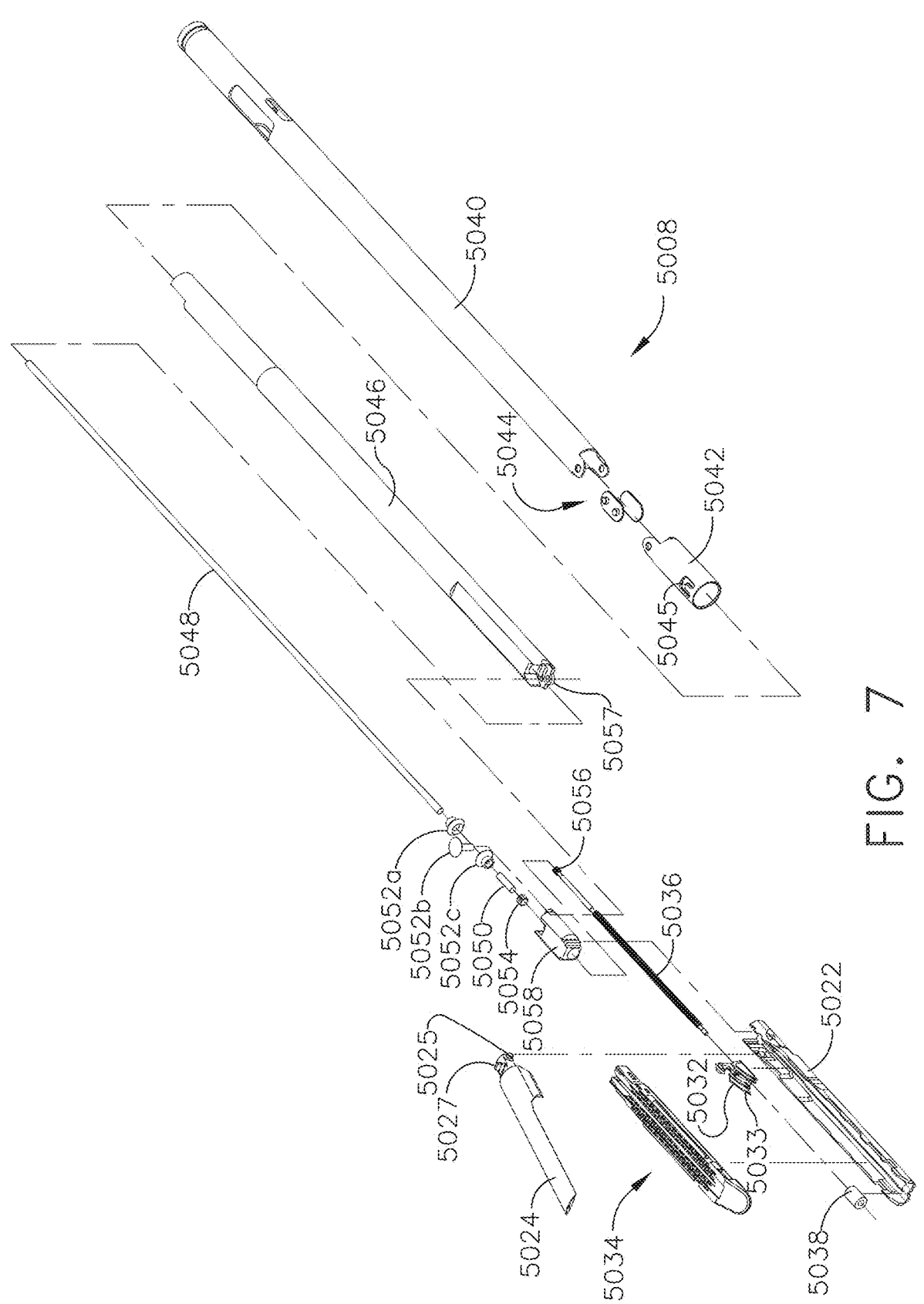
FIG. 7 is an exploded assembly view of portion of a shaft assembly of the powered surgical stapling system of FIG. 6.
Figure 8:
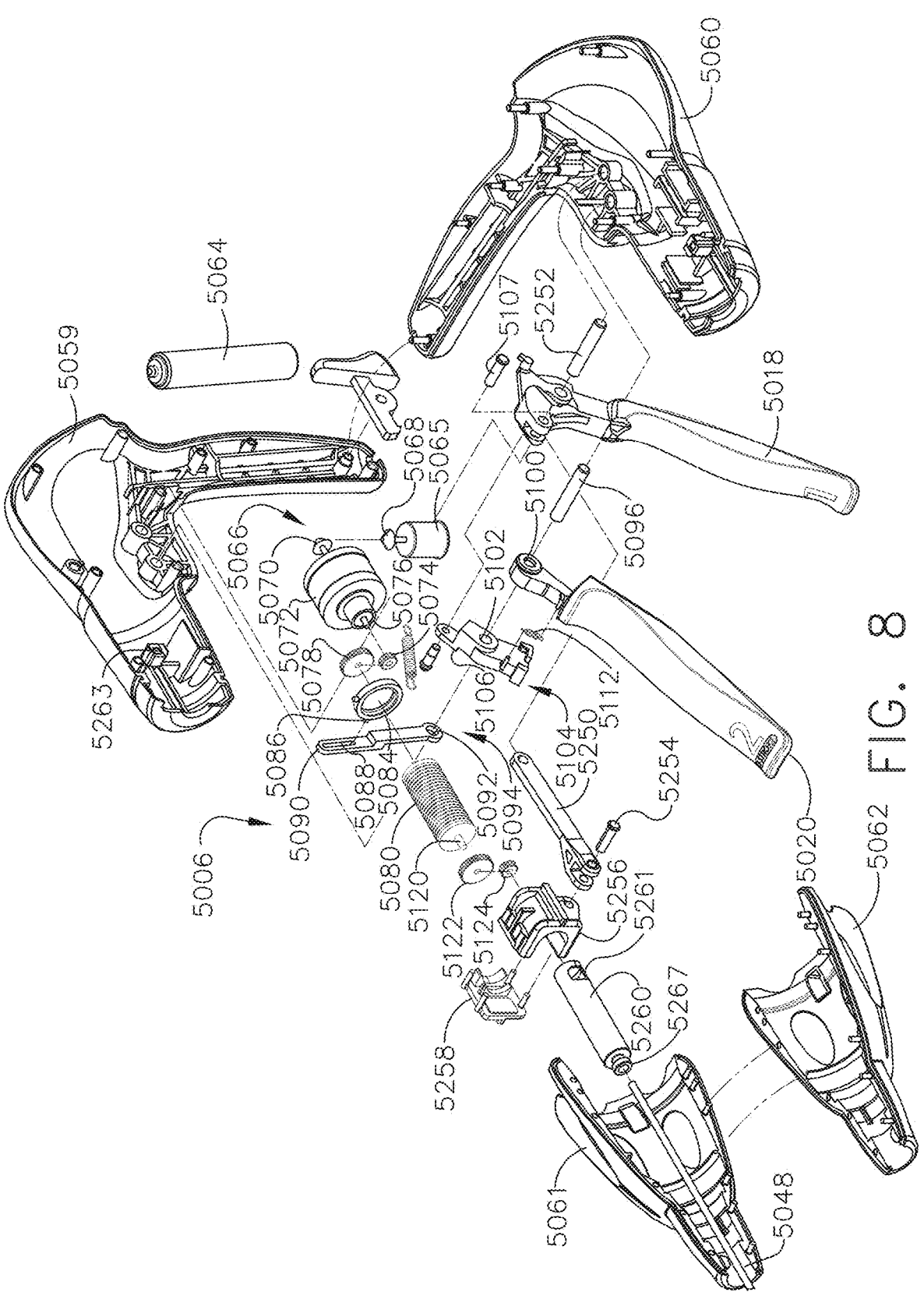
FIG. 8 is an exploded assembly view of portions of a handle assembly of the powered surgical stapling system of FIG. 6.

FIGS. 6-8 depict a surgical cutting and fastening instrument 5010 that is configured to generate rotary drive motions for operating a surgical end effector 5012. The surgical instrument 5010 comprises a handle 5006, a shaft 5008, and an articulating surgical end effector 5012 pivotally connected to the shaft 5008 at an articulation pivot 5014. An articulation control 5016 may be provided adjacent to the handle 5006 to effect rotation of the end effector 5012 about the articulation pivot 5014. Various alternative embodiments may include a non-pivoting end effector, and therefore may not have an articulation pivot 5014 or articulation control 5016.

The handle 5006 of the instrument 5010 may include a closure trigger 5018 and a firing trigger 5020 for actuating the end effector 5012. It will be appreciated that instruments having end effectors directed to different surgical tasks may have different numbers or types of triggers or other suitable controls for operating the end effector 5012. In one embodiment, a clinician or operator of the instrument 5010 may articulate the end effector 5012 relative to the shaft 5008 by utilizing the articulation control 5016, as described in more detail in U.S. Pat. No. 7,670,334, entitled SURGICAL INSTRUMENT HAVING AN ARTICULATING END EFFECTOR, the entire disclosure of which is incorporated herein by reference. The end effector 5012 includes, among other things, a staple channel 5022 and a pivotally translatable clamping member, such as an anvil 5024, which are maintained at a spacing that assures effective stapling and severing of tissue clamped in the end effector 5012. The handle 5006 includes a pistol grip 5026 toward which the closure trigger 5018 is pivotally drawn by the clinician to cause clamping or closing of the anvil 5024 toward the staple channel 5022 of the end effector 5012 to thereby clamp tissue positioned between the anvil 5024 and channel 5022.

In the arrangement depicted in FIG. 7, the end effector 5012 includes, in addition to the previously-mentioned channel 5022 and anvil 5024, a cutting instrument 5032, a sled 5033, a staple cartridge 5034 that is removably seated in the channel 5022, and a helical screw shaft 5036. The cutting instrument 5032 may be, for example, a knife. The anvil 5024 includes pivot pins 5025 that are movably supported in corresponding slots in the channel 5022. In one arrangement, the anvil 5024 includes a tab 5027 at its proximate end that is inserted into a component of the mechanical closure system (described further below) to open and close the anvil 5024.

Still referring to FIG. 7, the shaft 5008 includes a proximal closure tube 5040 and a distal closure tube 5042 pivotably linked by a pivot link 5044. The distal closure tube 5042 includes an opening 5045 into which the tab 5027 on the anvil 5024 is inserted in order to open and close the anvil 5024, as further described below. Disposed inside the closure tubes 5040, 5042 may be a proximate spine tube 5046.

Disposed inside the proximate spine tube 5046 may be a main rotational (or proximate) drive shaft 5048 that communicates with a secondary (or distal) drive shaft 5050 via a bevel gear assembly 5052a-c. The secondary drive shaft 5050 is connected to a drive gear 5054 that engages a proximate drive gear 5056 of the helical screw shaft 5036. The vertical bevel gear 5052b may sit and pivot in an opening 5057 in the distal end of the proximate spine tube 5046. A distal spine tube 5058 may be used to enclose the secondary drive shaft 5050 and the drive gears 5054, 5056. Collectively, the main drive shaft 5048, the secondary drive shaft 5050, and the articulation assembly (e.g., the bevel gear assembly 5052a-c) are sometimes referred to herein as the "main drive shaft assembly."

A bearing 5038, positioned at a distal end of the staple channel 5022, receives the helical screw shaft 5036, allowing the helical screw shaft 5036 to freely rotate with respect to the channel 5022. The helical screw shaft 5036 may interface a threaded opening (not shown) of the knife 5032 such that rotation of the helical screw shaft 5036 causes the knife 5032 to translate distally or proximately (depending on the direction of the rotation) through the staple channel 5022.

Turning next to FIG. 8, the handle 5006 includes exterior lower side pieces 5059, 5060 and nozzle pieces 5061, 5062 that fit together to form, in general, the exterior of the handle 5006. A battery 5064, such as a Li ion battery, may be provided in the pistol grip 5026 of the handle 5006. The battery 5064 powers a motor 5065 disposed in an upper portion of the pistol grip portion 5026 of the handle 5006. The motor 5065 may drive a 90° bevel gear assembly 5066 comprising a first bevel gear 5068 and a second bevel gear 5070. The bevel gear assembly 5066 may drive a planetary gear assembly 5072. The planetary gear assembly 5072 may include a pinion gear 5074 connected to a drive shaft 5076. The pinion gear 5074 may drive a mating ring gear 5078 that drives a helical gear drum 5080 via a drive shaft. A ring 5084 may be threaded on the helical gear drum 5080. Thus, when the motor 5065 rotates, the ring 5084 is caused to travel along the helical gear drum 5080 by means of the interposed bevel gear assembly 5066, planetary gear assembly 5072, and ring gear 5078.

The handle 5006 may include a middle handle piece 5104 adjacent to the upper portion of the firing trigger 5020. The handle 5006 also may comprise a bias spring 5112 connected between posts on the middle handle piece 5104 and the firing trigger 5020. The bias spring 5112 may bias the firing trigger 5020 to its fully open position. In that way, when the operator releases the firing trigger 5020, the bias spring 5112 will pull the firing trigger 5020 to its open position. The distal end of the helical gear drum 5080 includes a distal drive shaft 5120 that drives a ring gear 5122, which mates with a pinion gear 5124. The pinion gear 5124 is connected to the main drive shaft 5048 of the main drive shaft assembly. In that way, rotation of the motor 5065 causes the main drive shaft assembly to rotate, which causes actuation of the end effector 5012. The ring 5084 threaded on the helical gear drum 5080 may include a post 5086 that is disposed within a slot 5088 of a slotted arm 5090. The slotted arm 5090 has an opening 5092 in its opposite end 5094 that receives a pivot pin 5096 that is connected between the handle exterior side pieces 5059, 5060. The pivot pin 5096 is also disposed through an opening 5100 in the firing trigger 5020 and an opening 5102 in the middle handle piece 5104.

The middle handle piece 5104 includes a backside shoulder 5106 that engages the slotted arm 5090. The middle handle piece 5104 also has a forward motion stop 5107 that engages the firing trigger 5020. The movement of the slotted arm 5090 is controlled by rotation of the motor 5065. When the slotted arm 5090 rotates counter clockwise as the ring 5084 travels from the proximate end of the helical gear drum 5080 to the distal end, the middle handle piece 5104 will be free to rotate counter clockwise. Thus, as the user draws in the firing trigger 5020, the firing trigger 5020 will engage the forward motion stop 5107 of the middle handle piece 5104, causing the middle handle piece 5104 to rotate counter clockwise. Due to the backside shoulder 5106 engaging the slotted arm 5090, however, the middle handle piece 5104 will only be able to rotate counter clockwise as far as the slotted arm 5090 permits. In that way, if the motor 5065 should stop rotating for some reason, the slotted arm 5090 will stop rotating, and the user will not be able to further draw in the firing trigger 5020 because the middle handle piece 5104 will not be free to rotate counter clockwise due to the slotted arm 5090.

Components of an exemplary closure system for closing (or clamping) the anvil 5024 of the end effector 5012 by retracting the closure trigger 5018 are also shown in FIG. 8. In the illustrated embodiment, the closure system includes a yoke 5250 connected to the closure trigger 5018. A pivot pin 5252 is inserted through aligned openings in both the closure trigger 5018 and the yoke 5250 such that they both rotate about the same point. The distal end of the yoke 5250 is connected, via a pin 5254, to a first closure bracket 5256. The first closure bracket 5256 connects to a second closure bracket 5258. Collectively, the closure brackets 5256, 5258 define an opening in which the proximate end of the proximal closure tube 5040 (see FIG. 7) is seated and held such that longitudinal movement of the closure brackets 5256, 5258 causes longitudinal motion by the proximal closure tube 5040. The instrument 5010 also includes a closure drive shaft 5260 disposed inside the proximal closure tube 5040. The closure drive shaft 5260 may include a window 5261 into which a post 5263 on one of the handle exterior pieces, such as exterior lower side piece 5059 in the illustrated embodiment, is disposed to fixedly connect the closure drive shaft 5260 to the handle 5006. In that way, the proximal closure tube 5040 is capable of moving longitudinally relative to the closure drive shaft 5260. The closure drive shaft 5260 may also include a distal collar 5267 that fits into a cavity in proximate spine tube 5046 and is retained therein by a cap.

In operation, when the yoke 5250 rotates due to retraction of the closure trigger 5018, the closure brackets 5256, 5258 cause the proximal closure tube 5040 to move distally (i.e., away from the handle end of the instrument 5010), which causes the distal closure tube 5042 to move distally, which causes the anvil 5024 to rotate about the pivot pins 5025 into the clamped or closed position. When the closure trigger 5018 is unlocked from the locked position, the proximal closure tube 5040 is caused to slide proximately, which causes the distal closure tube 5042 to slide proximately, which, by virtue of the tab 5027 being inserted in the opening 5045 of the distal closure tube 5042, causes the anvil 5024 to pivot about the pivot pins 5025 into the open or unclamped position. In that way, by retracting and locking the closure trigger 5018, an operator may clamp tissue between the anvil 5024 and channel 5022, and may unclamp the tissue following the cutting/stapling operation by unlocking the closure trigger 5018 from the locked position. Further details concerning the construction and operation of the surgical instrument 5010 may be found in U.S. Pat. No. 7,845,537, entitled SURGICAL INSTRUMENT HAVING RECORDING CAPABILITIES, the entire disclosure of which is hereby incorporated by reference herein. Other rotary drive arrangements configured for use with various forms of robotic systems are disclosed in U.S. Patent Application Publication No. 2016/0287251, entitled STAPLING END EFFECTOR CONFIGURED TO COMPENSATE FOR AN UNEVEN GAP BETWEEN A FIRST JAW AND A SECOND JAW, the entire disclosure of which is incorporated by reference herein.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Figure 9:
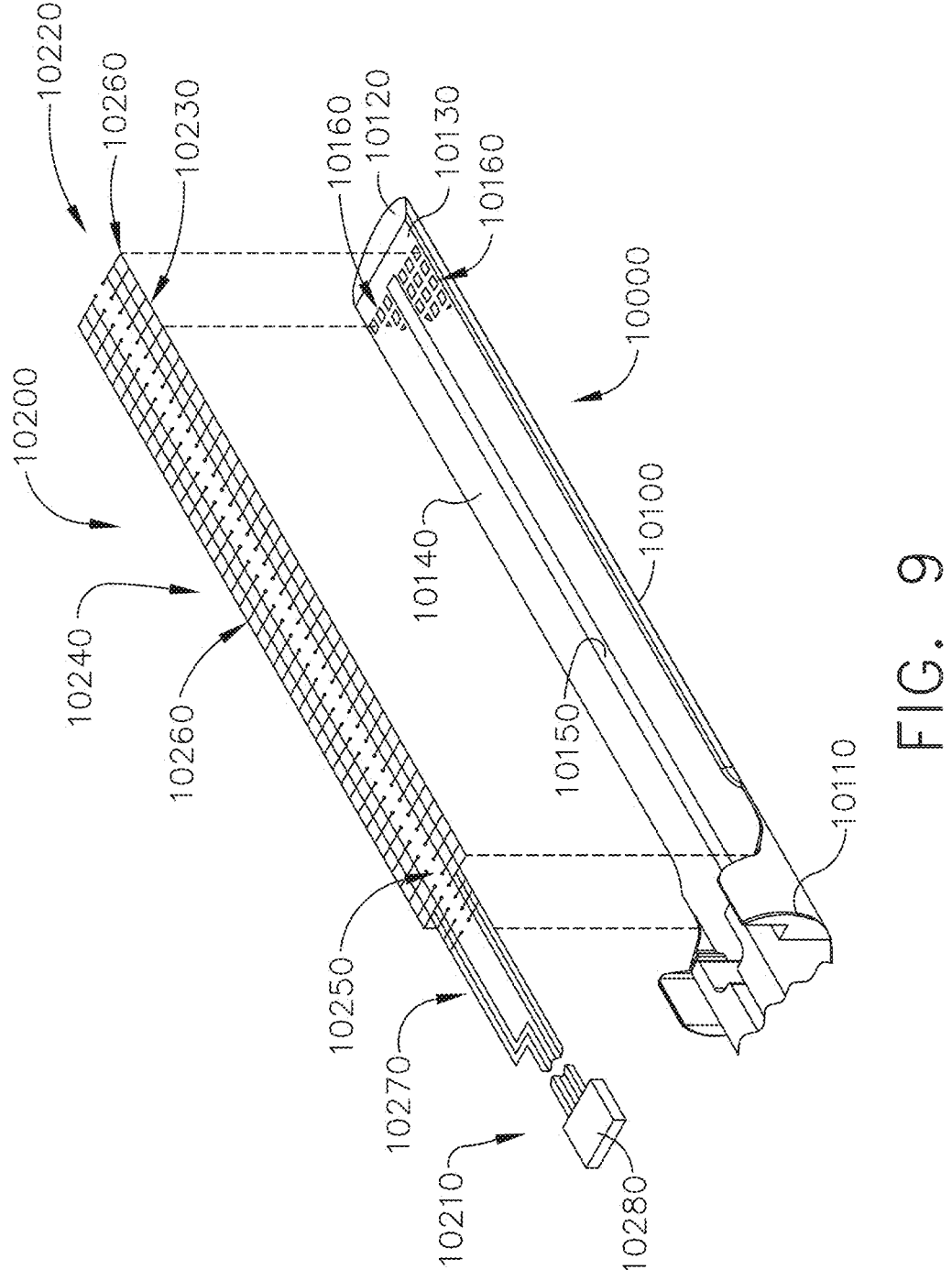
FIG. 9 is an exploded perspective view of an anvil jaw including forming pockets and a sensor system in accordance with at least one embodiment.

A jaw assembly 10000 is illustrated in FIG. 9. The jaw assembly 10000 comprises an anvil 10100 configured to deform staples ejected from a staple cartridge positioned opposite the anvil 10100. The anvil 10100 is rotatable relative to the staple cartridge between an open, or unclamped, position and a closed, or fully-clamped, position. In alternative embodiments, the staple cartridge is rotatable relative to the anvil 10100. In various other embodiments, at least one of the staple cartridge and the anvil 10100 is slideable into position relative to the other. In any event, the anvil 10100 comprises a proximal end 10110, a distal end 10120, and a longitudinal slot 10150 extending from the proximal end 10110 toward the distal end 10120. The longitudinal slot 10150 is configured to receive a staple firing member when the staple firing member is advanced distally during a staple firing stroke. In at least one instance, the staple firing member comprises a cam member configured to engage and position the anvil 10100 relative to the staple cartridge and a knife configured to cut the patient tissue positioned between the staple cartridge and the anvil 10100.

The anvil 10100 further comprises a tissue compression surface extending between the proximal end 10110 and the distal end 10120. The tissue compression surface comprises a first lateral side 10130 on a first lateral side of the longitudinal slot 10150 and a second lateral side 10140 on a second, or opposite, lateral side of the longitudinal slot 10150. The tissue compression surface is flat; however, in certain embodiments, the tissue compression surface can be cambered or contoured such that the distal end 10120 of the anvil 10100 is closer to the staple cartridge than the proximal end 10110 when the anvil 10100 is in a fully-clamped position. Moreover, the tissue compression surface can comprise longitudinal steps which extend along the length of the anvil 10100. The tissue compression surface is configured to directly contact the tissue positioned between the staple cartridge and the anvil 10100 when an implantable adjunct is not positioned on or attached to the anvil 10100. When an implantable adjunct is positioned on or attached to the anvil 10100, the tissue compression surface may not directly contact the tissue, but will still compress the tissue as the anvil 10100 is closed.

The anvil 10100 further comprises an array of staple forming pockets 10160 defined in the tissue compression surface. Each staple forming pocket 10160 is configured to deform a staple. In at least one instance, each staple forming pocket 10160 comprises a first forming cup configured to receive and deform a first leg of a substantially U-shaped, or V-shaped, staple and a second forming cup configured to receive and deform a second leg of the substantially U-shaped, or V-shaped, staple. That said, any suitable staple can be used. The entire disclosure of U.S. Patent Application Publication No. 2015/0297232, entitled FASTENER CARTRIDGE COMPRISING NON-UNIFORM FASTENERS, filed on Jun. 30, 2014 is incorporated by reference herein. The first forming cup is positioned proximally with respect to the second forming cup; however the forming cups can be arranged in any suitable manner. The staple forming pockets 10160 are arranged in three longitudinal rows in the first lateral side 10130 and three longitudinal rows in the second lateral side 10140. That said, the staple forming pockets

10160 can be arranged in any suitable manner. The entire disclosure of U.S. Patent Application Publication No. 2016/0089142, entitled METHOD FOR CREATING A FLEXIBLE STAPLE LINE, filed on Sep. 26, 2014 is incorporated by reference herein.

Figure 13A:
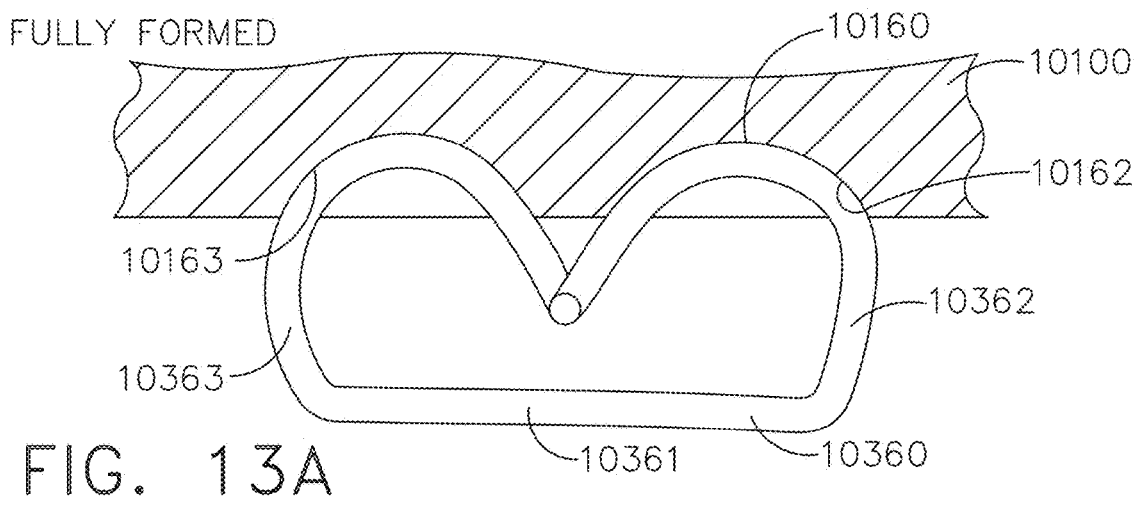
FIG. 13A depicts a formed staple in a B-shaped configuration.

Further to the above, a U-shaped staple generally comprises a base including a first end and a second end, a first leg extending upwardly from the first end of the base, and a second leg extending upwardly from the second end of the base where the first and second legs are parallel or substantially parallel to one another, i.e., they appear to be parallel under non-magnified observation. A V-shaped staple generally comprises a base including a first end and a second end, a first leg extending upwardly from the first end of the base, and a second leg extending upwardly from the second end of the base where the first and second legs extend away from each other. In various instances, the legs of a V-shaped staple are in contact with the sidewalls of the staple cavities defined in the staple cartridge such that the legs of the V-shaped staple are resiliently deflected inwardly. Such an arrangement creates a retaining force between the V-shaped staples and the cartridge body until the staples are ejected. In any event, each of the forming pockets 10160 is configured to deform the legs of a U-shaped staple-or a V-shaped staple-into a substantially B-shaped configuration, as illustrated in FIG. 13A.

Further to the above, a formed B-shaped configuration can be planar, where the base and the deformed legs lie in the same plane, or substantially planar, where the deformed legs twist slightly out of the base plane. Staples formed into a planar B-shaped configuration can compress and/or tightly clinch the tissue captured therein. The flow of blood through such staples is constricted and, as a result, bleeding through the longitudinal tissue incision made between the longitudinal staple lines is limited, if not prevented. Staples formed into a substantially planar B-shaped configuration also compress and/or tightly clinch the tissue captured therein. Out-of-plane deformed staple configurations compress and hold tissue in a third dimension which can allow the deformed staples to constrict the flow of blood there through with a lighter clinching pressure as compared to staples which are deformed into a planar configuration. The entire disclosure of U.S. Patent Application Publication No. 2018/0008260, entitled SURGICAL STAPLING INSTRUMENT, filed on Jun. 26, 2017 is incorporated by reference herein. The above being said, some out-of-plane twist can be advantageous while other out-of-plane twist can be tolerated, but, further to the below, instances can arise where it is desirable to limit and/or prevent the out-of-plane twist.

Further to the above, the forming cups of a forming pocket 10160 are configured to curl the legs of a staple inwardly toward one another to make the deformed B-shaped configuration. Referring to FIG. 13A, a staple 10360 comprises a base 10361, a first leg 10362 extending from the base 10361, and a second leg 10363 extending from the base 10361. The first leg 10362 contacts a first forming cup 10162 of the forming pocket 10160 and is curled inwardly toward the second leg 10363. Similarly, the second leg 10363 contacts a second forming cup 10163 of the forming pocket 10160 and is curled inwardly toward the first leg 10362. That said, a forming pocket, and/or any other forming surface, can be configured to bend the staple legs in any suitable manner and in any suitable direction.

Figure 13B:
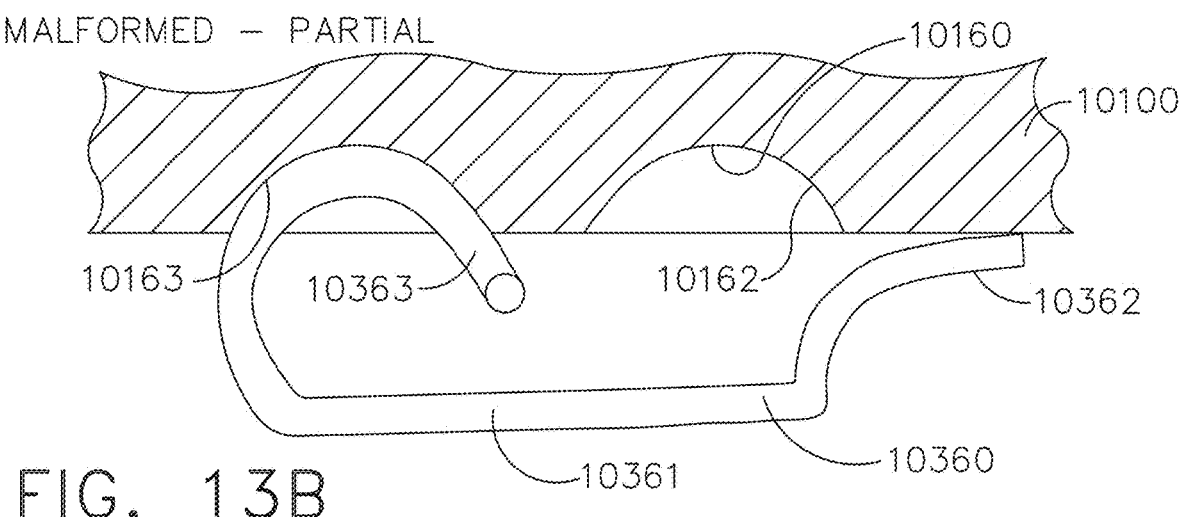
FIG. 13B depicts a staple in a partially-malformed configuration.
Figure 13C:
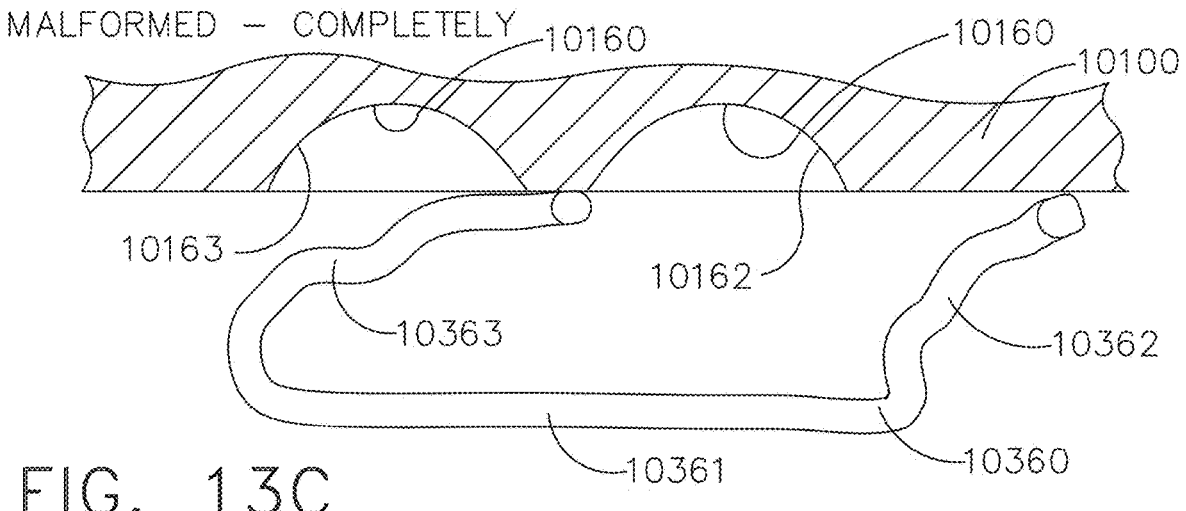
FIG. 13C depicts a staple in a completely-malformed configuration.

In various instances, referring to FIGS. 13B and 13C, one or both of the legs of a staple can miss the forming cups of a forming pocket 10160. In many such instances, the staple legs will contact the tissue compression surface, bend in the wrong direction, (FIG. 13B) and/or buckle (FIG. 13C). Such malformed staples can often perform their intended functions of sealing and securing the patient's tissue, but not always. Moreover, one malformed staple may not be problematic; however, several malformed staples located close to one another may require the clinician to take additional steps during a surgical procedure to seal and secure the tissue. For instance, the clinician may need to suture such areas of the tissue, although such a step takes additional time and clinicians typically endeavor to shorten surgical procedures—not lengthen them.

In view of the above, maintaining the alignment between the staples and the forming pockets 10160 allows the staples to be deformed in a desired manner. When a stapler comprising one or more rotatable jaws is being used, the anvil jaw and/or the staple cartridge jaw are rotated into a parallel alignment such that the staples in the staple cartridge are aligned with the forming pockets 10160 in the anvil. If one or both of the jaws is not fully closed, however, the staples and the forming pockets 10160 may be at least partially out of alignment. With this in mind, a stapling instrument can comprise a sensor system configured to detect whether the jaws have been sufficiently closed and/or in a suitable alignment relative to one another to perform a staple firing stroke. The sensor system is in signal communication with a control system of the stapling instrument which is configured to permit the motor-driven staple firing drive to be operated once the jaws have been detected as being closed, or at least suitably closed. In at least one instance, the sensor system includes a Hall Effect sensor mounted on the staple cartridge jaw, for example, which emits a magnetic field and detects changes in the magnetic field when the anvil is closed.

Once the jaws of the stapling instrument have been suitably closed, further to the above, the staple firing drive can be operated to advance a firing member, and a staple pushing sled, of the staple firing drive through a staple firing stroke to staple the patient tissue. In various instances, the stapling instrument comprises a handle including a firing trigger, or actuator, and a firing trigger sensor in signal communication with the control system that, when closed, signals the control system to operate the electric motor of the staple firing drive in a first direction. When the staple firing stroke is complete, the control system no longer powers the electric motor and, as a result, the firing member stops. When the clinician releases the firing trigger, the control system applies an opposite, or reverse, polarity to the electric motor to operate the electric motor in an opposite direction and retract the firing member. In various embodiments, the handle comprises a different actuator in communication with the control system which, when actuated, reverses the electric motor to retract the firing member.

During a staple firing stroke, further to the above, the firing member and the sled move from the proximal end of the end effector toward the distal end of the end effector. The staple firing stroke is complete when the firing member and the sled reach the distal end of the end effector; however, the staple firing stroke can be stopped at any suitable point and then retracted. During the staple firing stroke, a tissue cutting edge of the firing member contacts the tissue, applies a force to the tissue, and then incises the tissue as the firing member is advanced distally. In alternative embodiments, the sled comprises a tissue cutting edge. In either event, the tissue cutting edge may push the tissue distally, at least slightly, as the firing member moves distally even though the tissue is clamped between the anvil and the staple cartridge jaw. Stated another way, the tissue may flow distally during the staple firing stroke. In such instances, the distal tissue flow may bias, rotate, and/or shift the staples distally as they are being ejected from the staple cartridge and/or formed against the anvil. In many instances, the legs of the staples are nonetheless captured by the forming cups of the forming pockets 10160 and deformed into a suitable configuration. In some instances, however, the distal tissue flow can cause the staple legs to miss their corresponding forming cups in the anvil.

The distal tissue flow, further to the above, is more likely to occur when the tissue cutting edge of the firing member has become dull or dirty as compared to when the tissue cutting edge is sharp and clean. The tissue cutting edge can dull over the life of the stapling instrument when the stapling instrument is used to perform more than one staple firing stroke. In many instances, a stapling instrument is used at least twelve times, for example. In some instances, however, the tissue cutting edge can dull during a single staple firing stroke. Moreover, the distal tissue flow is more likely to occur when the tissue cutting edge has become damaged such as when the tissue cutting edge passes through previously-implanted staples, for example. The distal tissue flow is also more likely to occur when the tissue being cut is thick and/or dense and/or when the staple firing member is moving quickly. Whatever the cause for the distal tissue flow may be, a surgical stapling instrument can include a system to determine if the staples are being malformed and/or underformed and adapt the operation of the surgical stapling instrument to improve the deformation of the staples into a desired shape.

Referring again to FIG. 9, the jaw assembly 10000 further comprises a staple formation sensing system 10200 mounted to the anvil 10100. The staple formation sensing system 10200 comprises a first portion 10230 mounted to the first lateral side 10130 of the anvil 10100 and a second portion 10240 mounted to the second lateral side 10140 of the anvil 10100. The first portion 10230 of the staple formation system 10200 comprises a flex circuit including a flexible insulative substrate and electrical conductors 10270 extending through the substrate. The second portion 10240 of the staple formation system 10200 also comprises a flex circuit including a flexible insulative substrate and electrical conductors 10270 extending through the substrate. The flexible insulative substrates of the staple formation sensing system 10200 are attached to the anvil 10100 by one or more adhesives, for example, but could be attached to the anvil 10100 in any suitable manner. Alternatively, the electrical conductors 10270 can be mounted directly to the anvil 10100 without being embedded in a substrate. In at least one such instance, each conductor 10270 comprises an electrically conductive core surrounded by an insulative jacket, for example, where the insulative jacket is attached to the anvil 10100 by one or more adhesives, for example. In any event, the staple formation sensing system 10200 comprises a longitudinal opening 10250 defined therein which is aligned with the longitudinal slot 10150 defined in the anvil 10100 and is configured to permit a staple firing member and/or a tissue cutting edge to move relative to the staple formation sensing system 10200 without transecting it.

Figure 10:
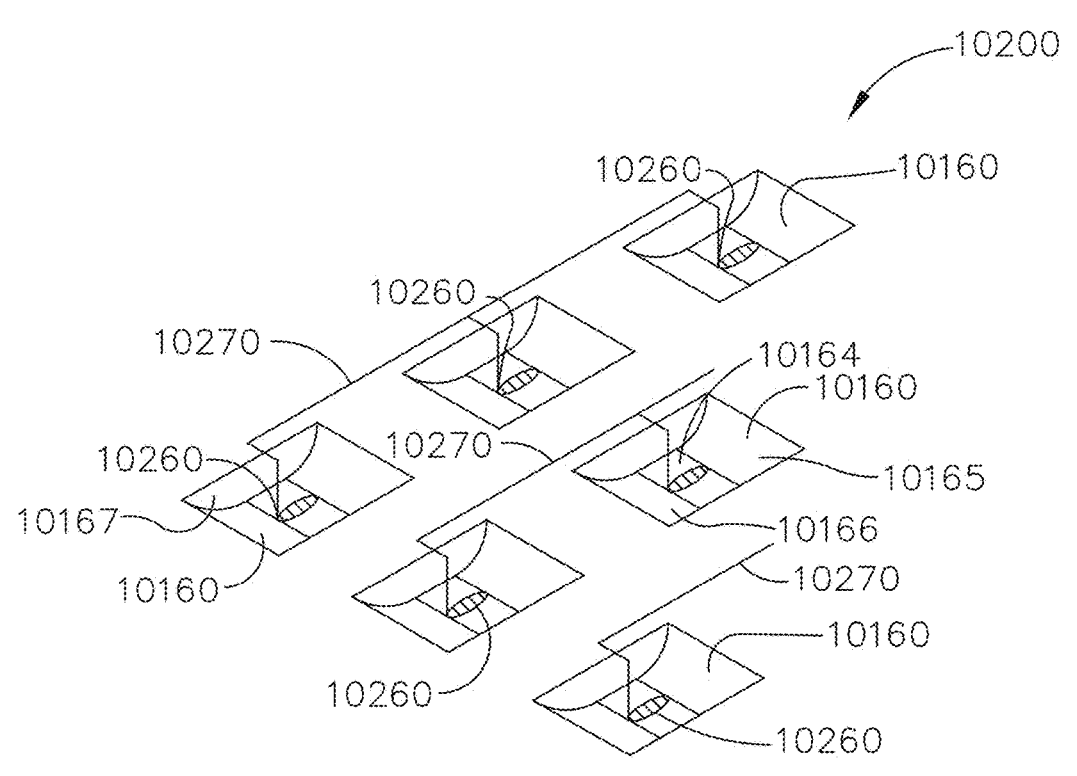
FIG. 10 is a partial detail view of the forming pockets and the sensor system of FIG. 9.

Referring to FIG. 10, the staple formation sensing system 10200 comprises contacts, or electrical traces, 10260 which are aligned with and positioned within the staple forming pockets 10160. Each forming cup of a staple forming pocket 10160 comprises a distal end wall 10165, a proximal end wall 10166, sidewalls 10167, and a bottom wall 10164 extending between the distal end wall 10165, the proximal end wall 10166, and the sidewalls 10167. The end walls

10165 and 10166 guide a staple leg into and out of the forming cup and the bottom wall 10164 turns the tip of the staple leg back toward the staple cartridge. The sidewalls 10167 co-operate to keep the staple leg in a longitudinal plane and to keep the staple leg in contact with the bottom wall 10164. An electrical trace 10260 is mounted on the bottom wall 10164 such that the staple leg being deformed by the forming cup contacts the electrical trace 10260. Each electrical trace 10260 comprises a base 10264 affixed to the bottom wall 10164 of the forming cup and an electrical contact 10266 supported by the base 10264. The base 10264 is comprised of an electrically-insulative material, such as plastic, for example, and the electrical contact 10266 is comprised of an electrically-conductive material, such as copper and/or stainless steel, for example. The base 10264 electrically separates the electrical contact 10266 from the anvil 10100, which is made from stainless steel and/or any other suitable metal.

The above being said, a forming cup can comprise any suitable configuration and can include one or more electrical traces in any suitable configuration. The entire disclosure of U.S. Pat. No. 9,220,502, entitled STAPLE FORMATION RECOGNITION FOR A SURGICAL DEVICE, which issued on Dec. 29, 2015 is incorporated by reference herein.

Further to the above, the electrical contact 10266 of each electrical trace 10260 is exposed such that the leg of a staple can make a conductive interface with the electric contact 10266 when the leg is being deformed within the forming cup. When both legs of a metal staple are in electrical communication with their respective electrical contacts 10266, the staple completes, or closes, an electrical circuit in the staple formation sensing system 10200. In various instances, the metal staple is comprised of stainless steel and/or titanium, for example. The staple formation system 10200 comprises a plurality of discrete and independent electrical sensing circuits-one for each staple forming pocket 10160—in communication with a control system, or control circuit, of the surgical stapling system. Referring to FIG. 9, the staple formation sensing system comprises an electrical connector 10280 including a housing and a plurality of electrical contacts. The electrical connector 10280 is configured to be mated to a corresponding electrical connector in the surgical instrument system to place the electrical traces 10260 in signal communication with a controller of the control system. The controller comprises a microprocessor, for example, configured to evaluate the independent electrical sensing circuits, i.e., evaluate whether the independent electrical sensing circuits have been closed by staples. In addition to or in lieu of the microprocessor in the controller, the electrical connector 10280 can comprise a microprocessor configured to communicate with the controller.

During a staple firing stroke, further to the above, the staples of a staple cartridge are progressively ejected by a firing member. Stated another way, the firing member ejects the proximal staples of the staple cartridge at the beginning of the staple firing stroke and the distal staples at the end of the staple firing stroke. The control system of the surgical stapling instrument is configured to evaluate the independent electrical sensing circuits during the staple firing stroke. In instances where all of the staples of a staple cartridge properly contact their staple forming pockets 10160 during the staple firing stroke, the staples will progressively close all of the independent electrical sensing circuits. In such instances, the control system does not modify the speed of the staple firing stroke owing to malformed staples as no staples have been malformed, or at least detected as being malformed. That said, in such instances, the control system can modify the speed of the staple firing stroke for other reasons such as when the magnitude of the current to the firing drive electric motor exceeds a threshold and/or when the firing member reaches the end of the staple firing stroke, for example. In various instances, the surgical instrument system comprises a current sensing circuit configured to detect the firing drive electric motor circuit and/or one or more sensors, such as an encoder, for example, configured to detect the position of the firing member relative to the end of the staple firing stroke.

Further to the above, the control system comprises a pulse width modulation (PWM) control circuit configured to control the speed of the firing drive electric motor. The PWM control circuit applies voltage pulses to the firing drive electric motor to perform the staple firing stroke. In various instances, the PWM control circuit increases the duration of the voltage pulses it applies to the firing drive electric motor in order to increase the speed of the firing drive electric motor and, correspondingly, the speed of the staple firing stroke. The PWM control circuit decreases the duration of the voltage pulses it applies to the firing drive electric motor in order to decrease the speed of the firing drive electric motor and, correspondingly, the speed of the staple firing stroke. The PWM control circuit applies the voltage pulses to the firing drive electric motor at regular intervals; however, the control system can comprise a frequency modulation (FM) control circuit to change the frequency of the voltage pulse intervals. In various instances, the FM control circuit decreases the interval between the voltage pulses to increase the speed of the firing drive electric motor and the staple firing stroke. Correspondingly, the FM control circuit increases the interval between the voltage pulses to decrease the speed of the firing drive electric motor and the staple firing stroke. In addition to or in lieu of the above, the control system can increase the magnitude of the voltage it applies to the firing drive electric motor to increase the speed of the firing drive electric motor and the staple firing stroke and/or decrease the magnitude of the voltage it applies to the firing drive electric motor to decrease the speed of the firing drive electric motor and the staple firing stroke.

As described above, the control system of the stapling instrument, in connection with the staple formation sensing system 10200, is configured to sense whether a staple is being properly formed in each of the staple forming pockets 10160. More specifically, as also described above, the control system determines that a staple is being properly formed in a staple forming pocket 10160 when a staple closes the sensing circuit for that staple forming pocket 10160. Correspondingly, the control system determines that a staple is not being properly formed in a staple forming pocket 10160 when a staple is not closing the sensing circuit for that staple forming pocket 10160. A staple may not close a sensing circuit when one or both of its staple legs have missed its corresponding staple forming pocket 10160. A staple will also not close its corresponding sensing circuit before the staple is fired, which happens as a matter of course in longitudinally-fired stapling instruments. In order to differentiate between these two events, the control system is configured to evaluate the sensing circuits for the staples that have been driven by and/or are currently being driven by the firing member. It is these sensing circuits that the control system uses to adapt the speed of the firing member, and not the sensing circuits for the staples that have not yet been fired. As such, the control system conducts a contemporaneous evaluation of the staples being formed to assess whether to slow down, speed up, and/or maintain the speed of the staple firing stroke. For instance, if the control system assesses that a staple is not being deformed properly, the control system slows the firing system electric motor in an attempt to create better staple formations. If the control system then assesses that subsequent staples are being deformed properly, the control system can return the staple firing stroke to its normal speed. Alternatively, the control system can maintain the staple firing stroke at its lowered speed even though subsequent staples are being deformed properly. In either event, however, if subsequent staples are not being deformed properly, the control system slows down the firing drive electric motor and the staple firing stroke even further. As described in greater detail below, the control system can pause the staple firing stroke if staples are being malformed.

As described above, the malformation of a single staple triggers the control system to slow the firing drive electric motor and the staple firing stroke. Other criteria can be used for slowing the firing drive electric motor and the staple firing stroke. In at least one instance, the malformation of two staples triggers the control system to slow the firing drive electric motor and the staple firing stroke. In certain instances, the malformation of two consecutive staples triggers the control system to slow the firing drive electric motor and the staple firing stroke. In various instances, the malformation of two staples in the same longitudinal staple row triggers the control system to slow the firing drive electric motor and the staple firing stroke. In at least one instance, the malformation of two consecutive staples in the same longitudinal row triggers the control system to slow the firing drive electric motor and the staple firing stroke. In at least one instance, the malformation of two consecutive staple legs in the same longitudinal row triggers the control system to slow the firing drive electric motor and the staple firing stroke. In various instances, a single malformed staple in the innermost longitudinal staple rows, i.e., the staple rows adjacent the longitudinal incision made by the stapling instrument, triggers the control system to slow the firing drive electric motor while a single malformed staple in the outermost longitudinal staple rows does not trigger the control system. In such instances, it would take two or more malformed staples in the outermost staple rows to trigger the control system to slow the firing drive electric motor, depending on the criteria set for the control algorithm. Other permutations of malformed staples, consecutive or non-consecutive, within the same, different, and/or adjacent longitudinal staple rows can trigger the control system to slow the firing drive of the stapling instrument. In at least one instance, a triggering event occurs when three laterally-aligned staples in a staple pattern are malformed. In such instances, a malformed staple is present in three adjacent staple rows that can permit blood to flow through the tissue incision.

Further to the above, completely malformed staples are treated differently than partially malformed staples. As discussed above, a completely malformed staple is a staple that has both legs which miss their corresponding forming cup while a partially malformed staple is a staple that has one leg which contacts its corresponding forming cup and one leg that misses its corresponding forming cup. In various instances, a partially malformed staple does not trigger the control system to slow the firing drive electric motor while a completely malformed staple triggers the control system to slow the firing drive electric motor. In other instances, a single partially malformed staple does not trigger the control system while two consecutive partially malformed staples triggers the control system to slow the firing drive electric motor. In at least one instance, the control system keeps a running count of completely malformed staples and partially malformed staples and slows the firing drive electric motor when the count reaches a predetermined threshold. In at least one such instance, the triggering count is 2.0, for example, where a completely malformed staple counts for 1.0 and a partially malformed staple counts for 0.5. In such an instance, the control system is triggered after one completely malformed staple and two partially malformed staples have been detected by the control system. Other permutations, and triggering counts, are possible.

As described above, the control system is configured to reduce the speed of the firing drive electric motor and the staple firing stroke when a triggering event has been identified by the algorithm of the control system. In various instances, the control system is configured to reduce the speed of the firing drive electric motor by half, or approximately half, for example, every time the control system is triggered. For instance, the normal speed of a firing member during a staple firing stroke can be 30 mm/second and, when the control system is triggered, the control system cuts the speed of the firing member to 15 mm/second. A subsequent triggering of the control system, in this example, reduces the speed of the firing member to 7.5 mm/second and so forth. In various instances, the control system has a minimum speed, or floor, below which the speed of the firing member does not fall unless the firing member is stopped, or paused. In various other embodiments, the control system reduces the speed of the staple firing stroke by 75%, or approximately 75%, once triggered, for example. Thereafter, in this embodiment, the firing stroke speed is not further reduced until the firing stroke is paused or stopped.

Figure 11:
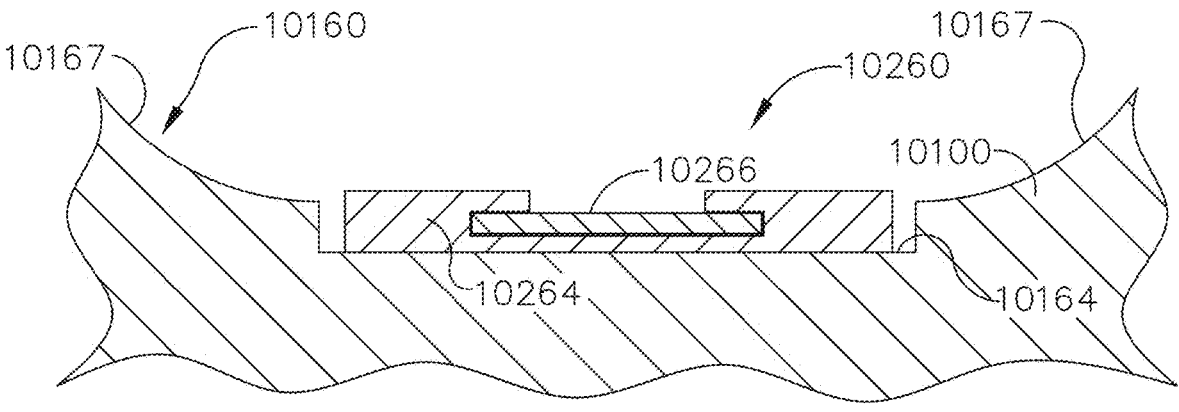
FIG. 11 is a partial cross-sectional view of the anvil jaw of FIG. 9.

As discussed above, referring again to FIGS. 10 and 11, the legs of the staples 10360 contact the traces 10260 positioned in the forming cups of the forming pockets 10160 when the staples 10360 are ejected from their staple cartridge during a staple firing stroke. As also discussed above, the traces 10260 are part of sensing circuits in communication with the control system of a surgical stapling system which is configured to assess whether or not the staple legs entered into the forming cups and, with this information, follow an algorithm for deciding whether or not to modify one or more operating parameters of the surgical stapling system. That said, properly deformed staples 10360 remain in contact with the traces 10260 throughout the staple firing stroke and, as such, the control system can be further configured to evaluate the quality of the contact between the staples 10360 and the traces 10260 to assess the shape of the staples 10360 after the staples 10360 have been deformed. When the staples 10360 have been deformed into a planar shape, or an at least substantially planar shape, large surface areas on the staples 10360 will be in contact with the traces 10260. When the staples 10360 have been deformed out-of-plane, i.e., deformed in a third dimension as discussed above, comparatively smaller surface areas on the staples 10360 will be in contact with the traces 10260. Owing to the larger contact areas, the resistance through the sensing circuits will be lower when the staples 10360 have been deformed into a substantially-planar shape as compared to when the staples 10360 have been deformed into a 3-D shape. When such 3-D staple shapes are desirable or tolerable, the control system can be programmed to remain in its normal operating mode, unless a different triggering event causes the control system to enter into a different operating mode. When such 3-D formed staple shapes are not desired, the control system can be programmed to enter into a second operating mode when 3-D formed staple shapes are detected by the control system. In the second operating mode, the control system can change one or more operating parameters of the surgical stapling system. For instance, the control system can reduce the speed of the stapling firing stroke as a slower staple firing stroke may reduce the deformation of the staples into out-of-plane 3D shapes.

In addition to or in lieu of the above, other staple formation sensing systems can be used to detect the malformation of staples during a staple firing stroke. In at least one instance, a staple formation sensing system comprises a flex circuit and an array of Hall Effect sensors mounted in the flex circuit. Each Hall Effect sensor is part of a sensing circuit in communication with the control system of the surgical stapling system. The flex circuit is mounted to the tissue-facing surface of the staple cartridge and/or to the tissue-facing surface of the anvil. In various instances, each Hall Effect sensor emits a magnetic field between a cartridge staple pocket and its corresponding anvil forming pocket. During the staple firing stroke, the magnetic fields produced by the Hall Effect sensors are disturbed by the staples being ejected from the staple cartridge. Each Hall Effect sensor is configured to evaluate the magnetic field that it produces when it is detectably disturbed by the position and/or shape of the deformed staple, for example. When a staple is properly formed by a staple forming pocket, the corresponding Hall Effect sensor detects a first magnetic field disturbance which is consistent with a properly-formed staple and, in such instances, produces a first voltage output. If a staple is malformed, however, the corresponding Hall Effect sensor detects a second magnetic field disturbance which is different than the first magnetic field disturbance and, in such instances, produces a second voltage output which is different than the first voltage output. When the control system receives a second voltage output from one of the Hall Effect sensing circuits, the control system can enter into a second operating mode in which at least one performance characteristic of the surgical stapling system is modified by the control system—assuming that all of the other control system algorithm criteria for entering into the second operating mode have been met. Notably, more than one formed deformed staple position and/or more than one deformed staple shape may be acceptable. In such instances, the voltage outputs of the Hall Effect sensors are compared to a range of acceptable outputs. If the voltage outputs fall within the acceptable range, then the control system continues to operate in its normal or default operating mode. If the voltage outputs fall outside of the acceptable range, then the control system enters a second, or different, operating mode.

In various instances, a staple formation sensing system can utilize tissue impedance spectrometry to evaluate whether or not the staples implanted into the tissue, or being implanted into the tissue, have been properly formed. Tissue impedance spectrometry can evaluate the electrical properties of the patient tissue which can change as a function of the stress, strain, and/or pressure that the tissue is enduring. Uncompressed, or unclamped, tissue has a first set of electrical properties. Clamped tissue has a second set of electrical properties which is different than the first set of electrical properties. Properly stapled tissue has a third set of electrical properties which is different than the first set and the second set, and tissue stapled by malformed staples has a set of electrical properties which is different than the first set, the second set, and the third set. In various instances, the electrical properties of the tissue are a function of the amount of water, fluid, and/or blood in the tissue. When the tissue is compressed by the anvil, a certain amount of water, fluid, and/or blood flows out of the compressed tissue into the surrounding tissue owing to the pressure being applied thereto by the end effector. In such instances, the compressed tissue has fewer ions and/or iron atoms contained therein which changes the impedance and/or capacitance of the tissue, for example. Such changes in the impedance and/or capacitance can be detected by the control system and compared to a set of criteria to assess where these electrical properties fall in their respective ranges. Similarly, a certain amount of water, fluid, and/or blood flows out of the tissue when the tissue is being properly stapled. Similar to the above, such changes in the impedance and/or capacitance can be detected by the control system and compared to the criteria to assess where these electrical properties now fall in their respective ranges. Notably, malformed staples will not cause the same amount of water, fluid, and/or blood flow out of the tissue as compared to properly-formed staples. As such, the electrical properties of the tissue will not change as much as they do when the tissue is properly stapled. These differences are detectable by the control system which is configured to enter into a different operating mode once it detects that the staples are not being properly formed.

In various embodiments, further to the above, the staple formation sensing system comprises sensing circuits where each sensing circuit includes a set of electrodes, i.e., an electrode on the anvil and an electrode on the staple cartridge which are aligned, or at least substantially aligned, with one another when the end effector is in a closed configuration. The sensing circuits are in communication with the control system and, when the control system applies a voltage potential to one of the electrodes of a sensing circuit, a signal current passes through the tissue between the set of electrodes of the sensing circuit. The control system comprises one or more ammeter circuits, for example, configured to measure the current flowing through the sensing circuits and, with this information, the control system is able to calculate the impedance of the tissue between the electrodes and assess whether the tissue has been properly stapled.

In various embodiments, further to the above, a staple formation detection system comprises one or more spectrometer circuits configured to evaluate one or more properties of the tissue to assess whether the tissue has been properly stapled. In at least one instance, the spectrometer circuits are configured to evaluate electromagnetic waves, for example, emanating from and/or reflected from the tissue. In various instances, each spectrometer circuit comprises one or more CCD and/or CMOS image sensors, for example. Properly stapled tissue can have a different color than improperly stapled tissue, for example, and such differences can be detected by the control system to assess whether to operate in a first operating mode or a second operating mode. Such color differences can arise from the amount and/or density of water, fluid, and/or blood in the tissue, for example.

In various embodiments, further to the above, a staple formation detection system can utilize magneto-impedance sensors to assess whether the tissue has been properly stapled. As discussed above, the electrical properties of the patient tissue change when exposed to stress, strain, and/or pressure. The magneto-impedance of the tissue is another detectable electrical property and the magneto-impedance sensors are configured to detect variations in the magneto-impedance of the tissue and compare those variations to the magneto-impedance of properly stapled tissue. If the control system determines that the tissue is not being properly stapled, the control system can adjust the position of the anvil jaw and/or adjust the speed of the staple firing system, for example.

Figure 15:
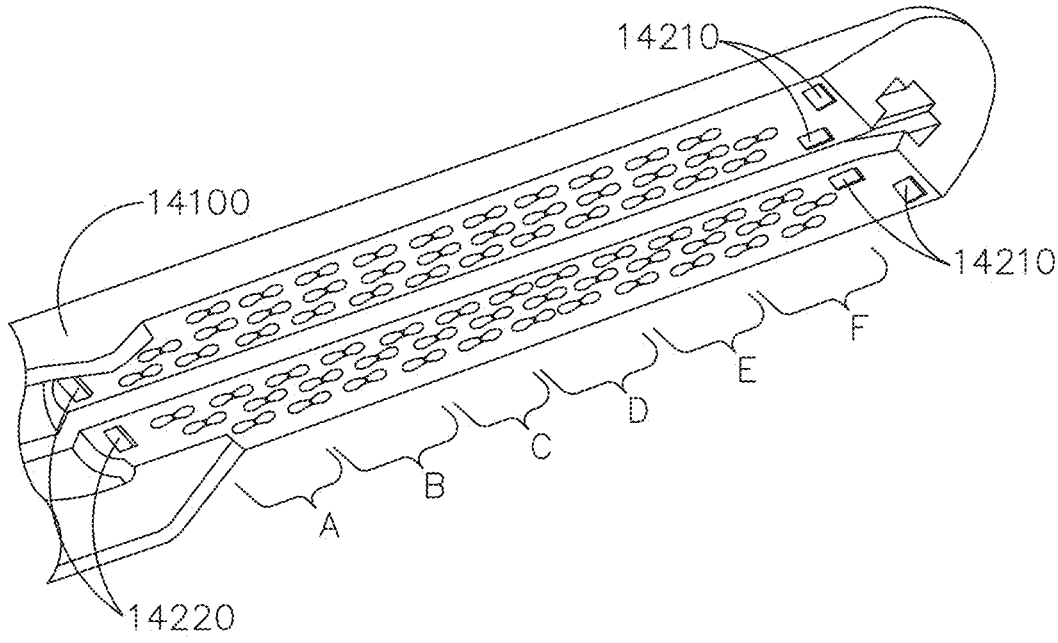
FIG. 15 is a perspective view of an anvil of the end effector of FIG. 14.

In various instances, as discussed above, a staple formation system can be configured to evaluate the formation of every staple ejected from a staple cartridge. Such an arrangement can provide very detailed information regarding the flow of the tissue and the formation of the staples. That said, embodiments are envisioned in which the formation of only some of the staples is evaluated. Referring to FIG. 15, evaluating one staple in each of zone A, zone B, zone C, zone D, zone E, and zone F is sufficient, in at least some embodiments, to properly assess the tissue flow and staple formation. In at least one embodiment, evaluating two staples in each of zone A, zone B, zone C, zone D, zone E, and zone F is sufficient to properly assess the tissue flow and staple formation. In at least one such embodiment, a staple on each side of the longitudinal tissue incision in each zone can be evaluated, for example.

In various instances, a control system is configured to evaluate the firing force experienced by the firing member during the staple firing stroke to assess whether the staples being formed by the firing member are being malformed. During a staple firing stroke in which the staples are being properly formed, the firing member will experience an average firing force, but that is not to say that the firing member will necessarily experience a constant force. Instead, a firing member experiences force peaks, and force valleys, during the staple firing stroke. Each force peak corresponds to the deformation of a staple or, more particularly, to the deformation of a staple into its fully-formed configuration. A properly-formed staple will usually cause a force peak; however, a malformed staple will usually cause an even larger force peak. With this in mind, a stapling instrument can be configured to detect the large force peaks consistent with the malformation of staples, as compared to the normal force peaks consistent with properly-formed staples, and slow the firing drive electric motor and the staple firing stroke, as described in greater detail below.

In various embodiments, further to the above, a staple firing drive of a surgical instrument includes a firing member which is translated longitudinally during a staple firing stroke. One or more stain gauges can be mounted to the firing member and placed in communication with the control system via one or more strain gauge circuits, which can extend through the drive components of the staple firing system and/or the housing of the stapling system, for example. The strain detected in the firing member is directly related to the firing force experienced by the firing member. As a result, the firing member will experience strain peaks, and strain valleys, that correspond to the force peaks, and force valleys, respectively, that are generated during the staple firing stroke. In addition to or in lieu of the above, one or more of the rotational members of the staple firing drive can include a strain gauge mounted thereto which is in communication with the control system via one or more strain gauge circuits. When the strain in the firing member, and/or any other component of the staple firing drive, exceeds a predetermined threshold, the control system will slow the firing drive electric motor and the staple firing stroke if the conditions for the triggering algorithm have been otherwise satisfied. Moreover, in addition to or in lieu of the above, the staple firing drive can include one or more load cells positioned intermediate components of the staple firing drive. The load cells are in communication with the control system and are configured to generate a voltage potential which is detected by a microprocessor of the control system. In at least one instance, each load cell comprises a piezoelectric transducer configured to convert a loading force within the firing drive system to an electric voltage potential which is proportional to the loading force. When the electric potential exceeds a predetermined threshold, the control system will slow the firing drive electric motor and the staple firing stroke if the conditions for the triggering algorithm have been otherwise satisfied.

In addition to or in lieu of the above, the force generated by the firing drive electric motor during the staple firing stroke is a function of the current drawn by the electric motor. When the firing member experiences a force peak, the electric motor current draw also peaks in a corresponding or proportional manner. When a staple is being malformed, the current peak drawn by the firing drive electric motor detectably exceeds the current peak drawn by the firing drive electric motor when a staple is being properly formed. In various instances, the control system comprises a current sensing or ammeter circuit, for example, configured to detect the current drawn by the firing drive electric motor. When the current peak exceeds a predetermined threshold, the control system will slow the firing drive electric motor and the staple firing stroke if the conditions for the triggering algorithm have been otherwise satisfied.

Figures 12, 12A:
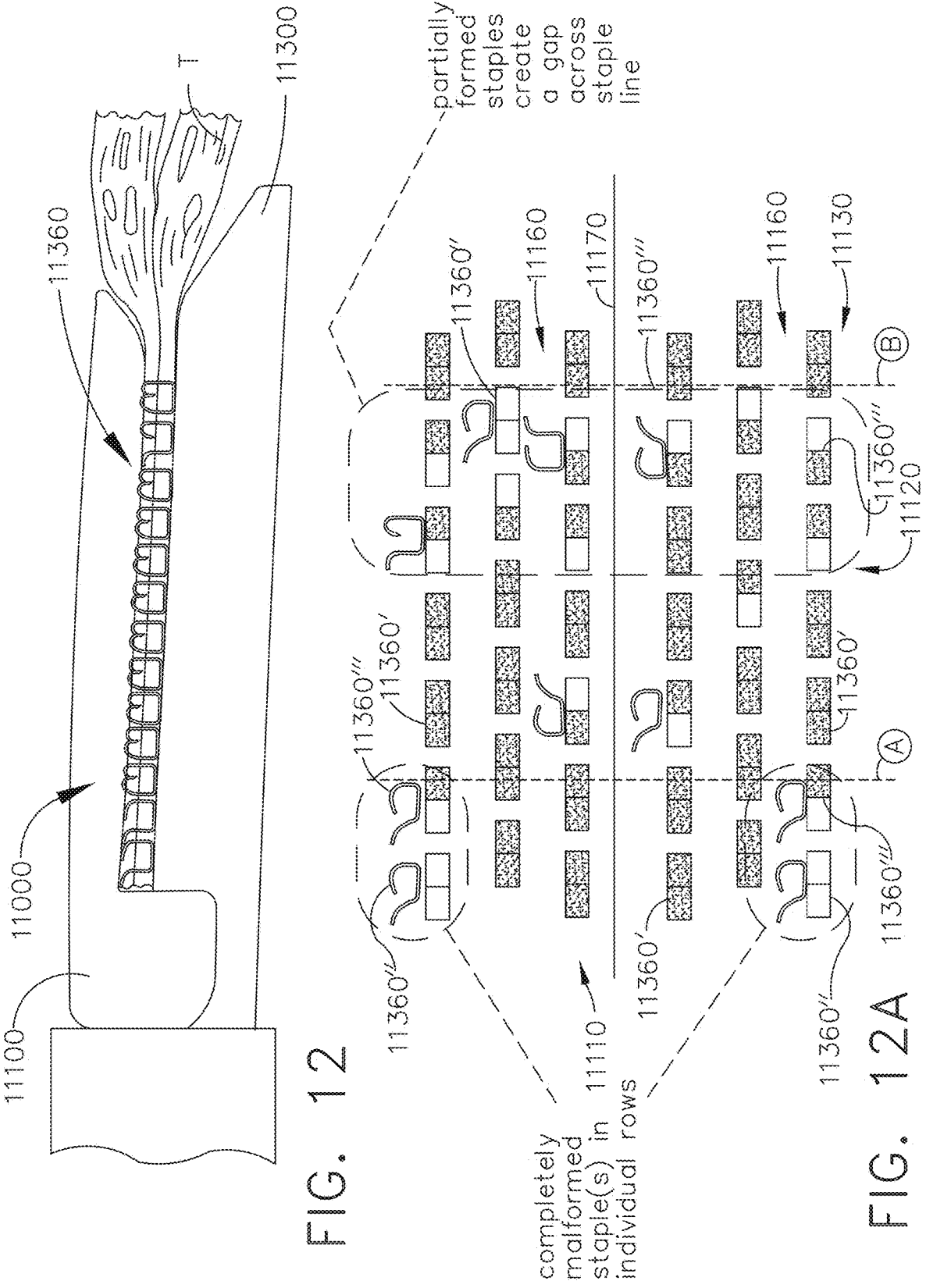
FIG. 12 is an elevational view of an end effector of a surgical stapling system in accordance with at least one embodiment.
FIG. 12A depicts the forming pockets of an anvil of the end effector of FIG. 12 and the staple pattern created by the end effector of FIG. 12.
Figure 12B:
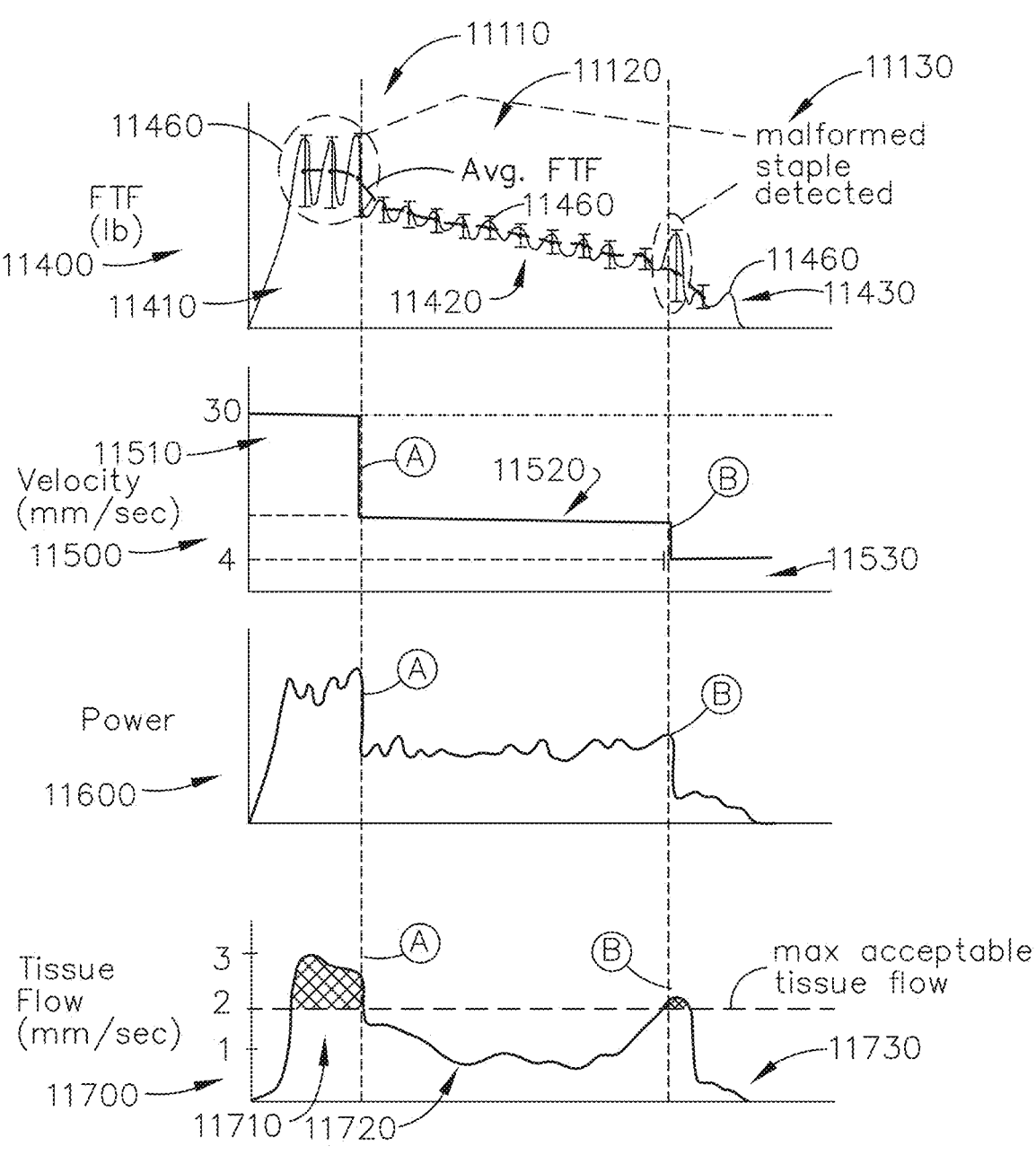
FIG. 12B comprises graphs relating to the operation of the surgical stapling system of FIG. 12.

Referring to FIGS. 12, 12A, and 12B, an end effector 11000 comprises an anvil jaw 11100 and a staple cartridge jaw 11300. The anvil jaw 11100 is rotatable relative to the staple cartridge jaw 11300 between an open, unclamped, position and a closed, clamped, position. In other embodiments, the staple cartridge jaw 11300 is rotatable relative to the anvil jaw 11100 between an open, unclamped, position and a closed, clamped, position. The staple cartridge jaw comprises a plurality of staples 11360 removably stored therein which are ejected during a staple firing stroke to secure the tissue T captured between the anvil jaw 11100 and the cartridge jaw 11300. FIG. 12 illustrates the end effector 11000 in a fully-fired configuration, i.e., after the complete staple firing stroke. FIG. 12A graphically depicts the formation of the staples 11360 by forming pockets 11160. Properly-formed staples 11360 are depicted as grey rectangles 11360' in FIG. 12A. Completely-malformed staples 11360 are depicted as white rectangles 11360" in FIG. 12A while partially-malformed staples 11360 are depicted as half-white/half-grey rectangles 11360" which indicates that one of the staple legs was properly formed while the other was not.

Referring again to FIG. 12A, the beginning of the depicted staple firing stroke is represented by the reference number 11110, the middle of the depicted staple firing stroke is represented by the reference number 11120, and the end of the depicted staple firing stroke is represented by the reference number 11130. The tissue transection line is represented by line 11170. As indicated in FIG. 12A, several staples 11360 were completely malformed and several staples 11360 were partially malformed during the beginning 11110 of the staple firing stroke. Referring to the force-to-fire graph 11400 of FIG. 12B, the complete and partial malformation of these staples 11360 created several large peaks 11460 in the firing force being transmitted through the staple firing drive. In fact, three large peaks 11460 can be seen in the beginning 11410 of the force-to-fire curve which corresponds to the beginning 11110 of the staple firing stroke of FIG. 12A. Further to the above, these large force peaks 11460 created a triggering event A in the control system of the stapling instrument and, as a result, the control system slowed the electric motor of the firing drive during the middle 11120 of the staple firing stroke. As a result of the slower speed, referring again to FIG. 12B, the average force-to-fire of the firing drive lowered and the force peaks 11460 lowered as well. The lower force-to-fire during the middle 11120 of the staple firing stroke is depicted in the middle 11420 of the force-to-fire curve. The change in speed of the staple firing drive is depicted in the speed graph 11500 of FIG. 12B. More specifically, the middle 11520 of the speed curve is lower than the beginning 11510 of the speed curve. As outlined above, the slower speed of the staple firing drive reduced the distal flow of the tissue being stapled and, as a result, the formation of the staples 11360 improved. This reduction in distal tissue flow is depicted in graph 11700 in FIG. 12B where the tissue flow 11710 at the beginning 11110 of the staple firing stroke exceeds a threshold of 2 mm/second and the tissue flow 11720 during the middle 11120 of the staple firing stroke falls below the 2 mm/second threshold. The slower speed of the staple firing drive also reduced the power needed by the firing drive electric motor to perform the staple firing stroke, as depicted by the power curve 11600 of FIG. 12B.

As indicated in FIG. 12A, several staples 11360 were malformed during the middle 11120 of the staple firing stroke so as to trigger the control system once again during a triggering event B. Further to the above, referring again to the tissue flow graph 11700 of FIG. 12B once again, these staple malformations occurred because the distal tissue flow exceeded the 2 mm/second threshold once again. Referring again to the force-to-fire graph 11400 of FIG. 12B, the complete and partial malformation of these staples 11360 created a large peak 11460 in the firing force being transmitted through the staple firing drive. In response, the control system slowed the electric motor of the firing drive during the end 11130 of the staple firing stroke. As a result of the slower speed, referring again to FIG. 12B, the average force-to-fire of the firing drive lowered and the force peaks 11460 lowered as well. The lower force-to-fire during the end 11130 of the staple firing stroke is depicted in the end 11430 of the force-to-fire curve. The change in speed of the staple firing drive is depicted in the speed graph 11500 of FIG. 12B. More specifically, the end 11530 of the speed curve is lower than the middle 11520 of the speed curve. As outlined above, the slower speed of the staple firing drive reduced the distal flow of the tissue being stapled and, as a result, the formation of the staples 11360 improved. This reduction in distal tissue flow is depicted in graph 11700 in FIG. 12B where the tissue flow 11730 at the end 11130 of the staple firing stroke is lower than the tissue flow 11720 during the middle 11120 of the staple firing stroke. The slower speed of the staple firing drive also reduced the power needed by the firing drive electric motor to perform the staple firing stroke, as depicted by the power curve 11600 of FIG. 12B.

As discussed above, the distal flow of tissue within an end effector can be reduced by slowing the staple firing stroke. The distal flow of tissue can also be reduced by increasing the clamping pressure, or force, applied to the tissue by the jaws of the end effector. In a way, the higher clamping force between the anvil jaw and the staple cartridge jaw holds the tissue in place and prevents, or at least reduces, the flow of tissue distally. As a result, the staples being driven through the tissue during the staple firing stroke are less likely to miss their corresponding forming pockets. In general, the clamping force applied to tissue captured between the anvil jaw and the staple cartridge jaw increases as the tissue gap between the anvil jaw and the staple cartridge jaw decreases. When the anvil jaw is movable relative to the staple cartridge jaw, the anvil jaw is moved closer to the staple cartridge jaw to increase the clamping force to the tissue. Correspondingly, the staple cartridge jaw is moved closer to the anvil jaw to increase the clamping force to the tissue when the staple cartridge jaw is movable relative to the anvil jaw.

In various instances, a surgical stapling system comprises a motor-driven jaw closure system configured to close the end effector of the surgical stapling system and an independently-operated motor-driven staple firing system configured to perform a staple firing stroke. During the staple firing stroke, the closure system holds the jaws in their closed configuration. After the staple firing stroke has been completed, or at least sufficiently completed, the firing member is retracted. Once the firing member has been sufficiently retracted, the closure system is operated to drive the end effector into its open configuration and/or permit the end effector to open in response to an opening force from one or more biasing members. As a result of the above, the closure drive and the staple firing drive are operated in a separate and distinct manner. As such, the clamping force applied to the tissue by the closure drive can be adjusted based on one or more operating parameters of the staple firing drive, as discussed in greater detail below.

In various instances, further to the above, a surgical stapling system is used to perform more than one staple firing stroke, or firings. In at least one such instance, a surgical stapling system can be used to perform twelve staple firings, for example, before the tissue cutting knife of the surgical stapling system has become too dull to properly cut the patient tissue. That said, the tissue cutting knife does not suddenly become dull after the twelfth staple firing; rather, the tissue cutting knife becomes progressively duller as a result of each staple firing. As the tissue cutting knife becomes duller, the force required to cut the patient tissue may increase, from one staple firing stroke to the next, which can, in turn, increase the distal flow of tissue during the staple firing stroke. Thus, the distal tissue flow during the twelfth staple firing stroke of a surgical stapling instrument can be greater, if not far greater, than the distal tissue flow during the first staple firing stroke of the surgical stapling instrument.

Figure 18:
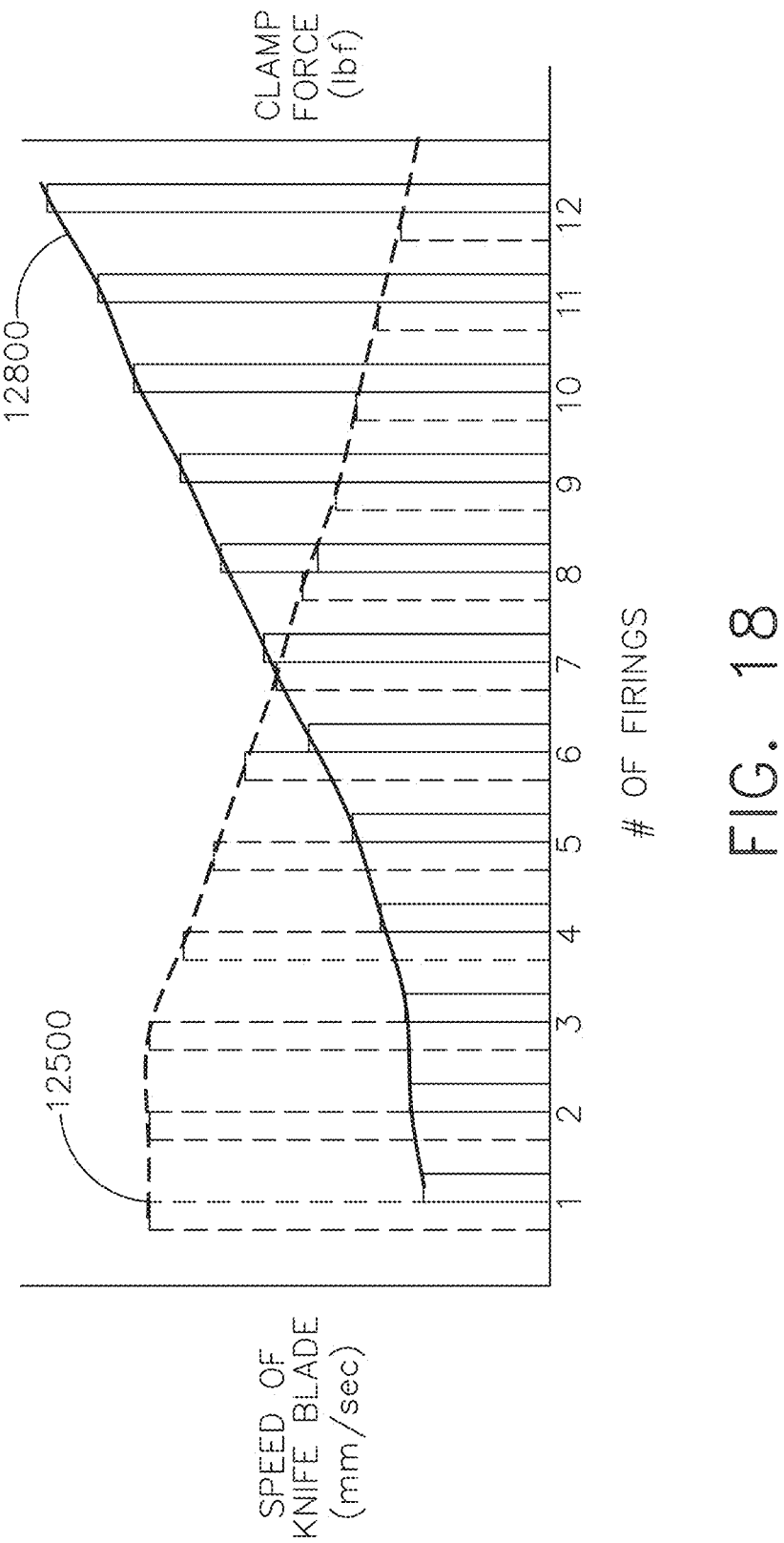
FIG. 18 comprises graphs relative to the operation of a surgical stapling system in accordance with at least one embodiment.

In view of the above, referring to FIG. 18, the control system of the surgical stapling system is configured to increase the clamping force applied to the tissue by the end effector from one staple firing stroke to the next. The clamping force applied to the tissue is depicted by curve 12800 in FIG. 18. From FIG. 18, it can be seen that the clamping force applied to the tissue during the second firing stroke is greater than the clamping force applied to the tissue during the first firing stroke. It can also be seen that the clamping force applied to the tissue during the third firing stroke is greater than the clamping force applied to the tissue during the second firing stroke, and so forth. The control system comprises a counting circuit configured to count the number of firings performed by the surgical stapling system. In at least one instance, the microprocessor of the control system comprises a digital counting circuit that is incremented every time a staple firing stroke is initiated. After each firing, the count is indexed by one and, when the next firing is performed, the control system applies a larger clamping force to the tissue. The increase in clamping force can be a percentage increase, for example. For instance, the control system can increase the clamping force by 10% of the original clamping force for each firing. Such an arrangement will result in a linear increase in clamping force across all twelve firings. To the extent that the surgical stapling system is used beyond twelve firings, the control system can continue to increase the clamping force in a linear manner from one firing to the next. In an at least one arrangement, the slope of the clamping force curve 12800 increases past the twelfth firing, and/or any other suitable firing, such that the clamping force thereafter increases at a higher rate from one firing to the next.

As described above, the closure drive of the surgical stapling system comprises an electric motor operably coupled to a longitudinally-translatable closure member. The closure member is movable proximally when the electric motor is rotated in a first direction and distally when the electric motor is rotated in a second, or opposite, direction. When the closure member is advanced distally, the closure member engages a movable end effector jaw and moves the jaw toward its closed, or clamped, position. When the closure member is retracted proximally, the closure member moves the end effector jaw into its open position. Alternatively, the proximal motion of the closure member can close the end effector and the distal motion of the closure member can open the end effector. Throughout the closing and opening strokes, the closure member remains in contact with the jaw to control the position of the jaw. The electric motor comprises a brushless electric motor and is controllable by the control system to position the jaw in its closed position. In such instances, the control system can track the position of the movable jaw. That said, the closed position of the jaw is a function of the clamping force that is to be applied to the tissue by the control system. When the control system increases the tissue clamping force, the control system positions the movable jaw closer to the other jaw to reach a closed position. Correspondingly, the control system positions the movable jaw further away from the other jaw to reach a closed position when the control system decreases the tissue clamping force. In various alternative embodiments, further to the above, the closure drive of the surgical stapling system comprises a brushed motor and is configured to drive the movable jaw into a closed position.

The surgical stapling system further comprises one or more strain gauges mounted to the movable jaw and/or the stationary jaw in communication with the control system to detect the clamping force being applied to the tissue by the closure drive. In addition to or in lieu of the above, the surgical stapling system further comprises one or more load cells in the closure drive in communication with the control system to detect the clamping force being applied to the tissue. In addition to or in lieu of the above, the control system comprises an ammeter circuit configured to measure the current drawn by the closure drive electric motor. The current drawn by the closure drive electric motor is proportional to the clamping force being applied to the tissue captured between the jaws. Regardless of the means used to detect the clamping force being applied to the tissue, the control system is configured to stop the closure drive once the clamping force has reached its intended level.

In addition to or in lieu of increasing the clamping force applied to the tissue from one firing stroke to the next to reduce the distal flow of tissue, the control system is configured to reduce the speed of the staple firing stroke from one firing stroke to the next. Reducing the speed of the staple firing stroke, as established above, can reduce the distal flow of tissue. Referring to curve 12500 in FIG. 18, the speed of the fourth firing is slower than the speed of the third firing, for example. Similarly, the speed of the fifth firing is slower than the speed of the fourth firing, and so forth. The reduction in speed between firings is linear; however, any suitable speed reduction algorithm could be used. In at least one instance, the speed of the staple firing stroke is reduced by 5% for each firing, for example. Notably, though, the speed of the staple firing stroke does not need to be lowered after each firing. For instance, referring again to the speed curve 12500 in FIG. 18, the speed of the staple firing stroke is not lowered between the first firing and the second firing and, likewise, between the second firing and the third firing, for example.

Figure 17:
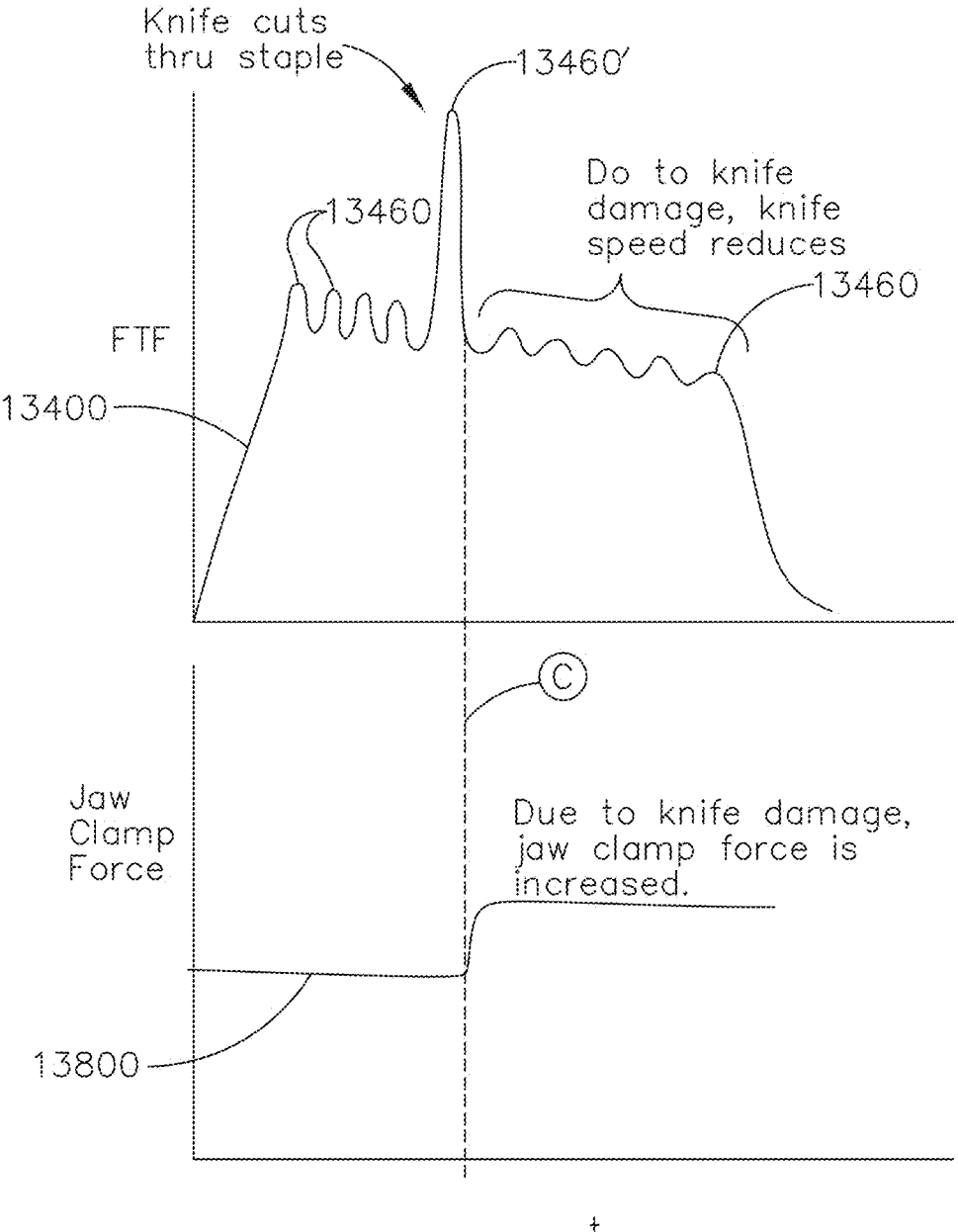
FIG. 17 comprises graphs relative to the operation of a surgical stapling system in accordance with at least one embodiment.

As discussed above, a control system of a surgical stapling system can be configured to adjust the clamping force that it applies to the patient tissue from one firing to the next. In addition to or in lieu of the above, referring to FIG. 17, a control system is configured to increase the clamping force during a staple firing stroke in response to a triggering event, such as triggering event C, for example. In at least one instance, the triggering event C occurs when the tissue cutting knife of the surgical stapling system transects a previously-implanted staple, for example, which causes a large force peak 13460' in the firing force curve 13400 in FIG. 17. Further to the above, the control system is configured to distinguish between the large force peak 13460' and the normal staple firing peaks 13460 that occur during a typical staple firing stroke such that only the large force peak 13460', and/or any other abnormal force peak, triggers the control system to adapt the operation of the surgical stapling system. The increase in jaw clamping force after the triggering event C is depicted in the jaw clamp force curve 13800 in FIG. 17. The amount in which the jaw clamping force is increased is a function of the magnitude and/or duration of the large force peak 13460'. In instances where the magnitude of the large force peak 13460' is twice as large as a normal force peak 13460, the control system increases the jaw clamping force by 10%, for example. Along these lines, the control system increases the jaw clamping force by 20%, for example, when the magnitude of the large force peak 13460' is four times as large as a normal force peak 13460. Similarly, in instances where the duration of the large force peak 13460' is twice as long as a normal force peak 13460 for a given staple firing speed, the control system increases the jaw clamping force by 10%, for example. Along these lines, the control system increases the jaw clamping force by 20%, for example, when the duration of the large force peak 13460' is four times as long as a normal force peak 13460 for a given staple firing speed. In any event, the control system of the surgical stapling system is configured to adapt the clamping force it is applying to the patient tissue during the staple firing stroke in response to one or more events that occur during the staple firing stroke.

Further to the above, the large force peak 13460' indicates that the tissue cutting blade may have been damaged or blunted in some way. As discussed above, the control system is programmed to respond to this potential damage to the tissue cutting blade by squeezing harder on the tissue to prevent, or at least reduce, the distal flow of tissue during the staple firing stroke. In addition, the control system can be programmed to respond to this potential damage to the tissue cutting blade by slowing down the staple firing stroke to prevent, or at least reduce, the distal flow of tissue during the staple firing stroke. Thus, a triggering event during a staple firing stroke can cause the control system to simultaneously clamp harder on the tissue and slow down the staple firing stroke.

As discussed above, the force-to-fire curve experienced during a staple firing stroke can be characterized by an average force-to-fire and force peaks which correspond to the deformation of individual staples. That said, the control system of a surgical stapling system can be configured to evaluate the height, or magnitude, of the force peaks relative to the average force-to-fire curve. If the magnitudes of the force peaks relative to the average force are within a predetermined range, the control system implements a first operating mode. If, however, the magnitudes of the force peaks relative to the average force are below the predetermined range, the control system implements a second operating mode as the low force peaks can indicate that the staples are not being fully formed. In the second operating mode, the control system moves the anvil jaw toward the staple cartridge jaw to decrease the staple forming gap between the two jaws. In such instances, the magnitudes of the force peaks should increase thereby indicating that the staples are being fully formed. Correspondingly, the control system is configured to move the anvil jaw away from the staple cartridge jaw to increase the staple forming gap between the two jaws when the control system senses that the force peaks relative to the average force are above the predetermined range.

Figure 14:
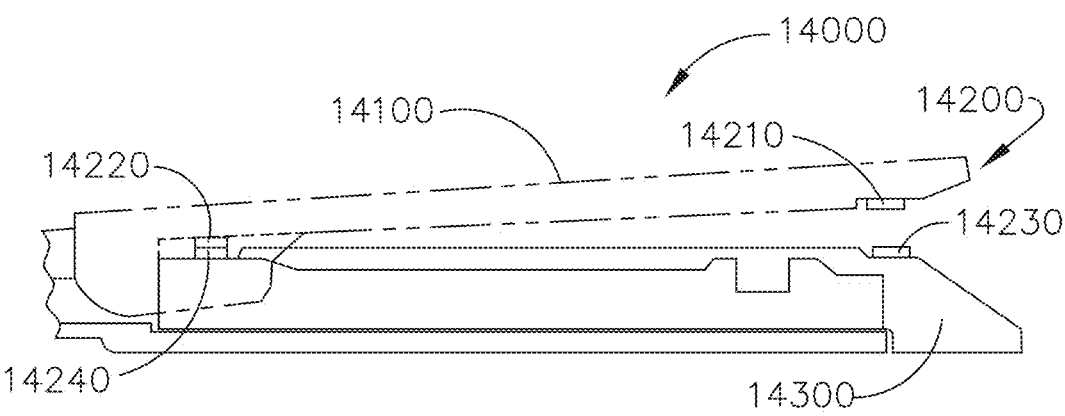
FIG. 14 is an elevational view of an end effector of a surgical stapling system in accordance with at least one embodiment.
Figure 16:
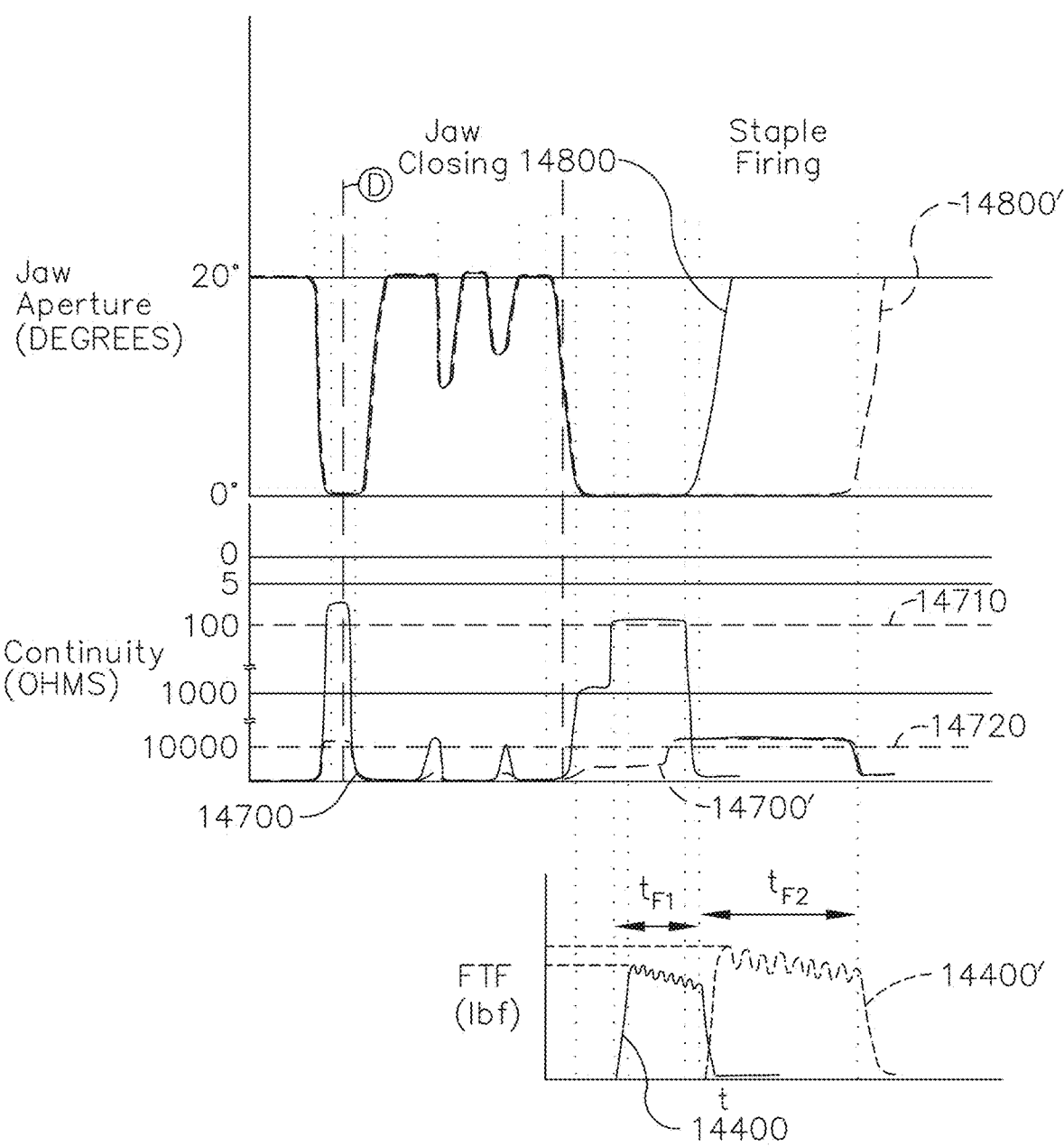
FIG. 16 comprises graphs relating to the operation of the surgical stapling system of FIG. 14.

As discussed above, various surgical stapling systems are configured to implant longitudinal rows of staples in the tissue of a patient and incise the patient tissue along a tissue incision path extending between two of the longitudinal staple rows. In various instances, an implantable adjunct is releasably attached to the staple cartridge jaw such that the staples capture the implantable adjunct against the patient tissue as the staples are being fired during the stapling firing stroke. When the jaws of the surgical stapling system are released from the patient tissue, the adjunct remains implanted against the tissue. In addition to or in lieu of an implantable adjunct on the staple cartridge, the surgical stapling system can comprise an implantable adjunct releasably attached to the anvil jaw. In such instances, the staples puncture the tissue and then capture the implantable adjunct against the tissue as the staples are being deformed against the anvil. In either event, an implanted adjunct material can provide several benefits such as mechanically bolstering the tissue and/or delivering a therapeutic agent to the tissue, such as medicament, for example. That said, the tissue cutting edge of the surgical stapling instrument may have to transect the implanted adjuncts during the staple firing stroke which, in various instances, may affect the performance of the surgical stapling system. As described in greater detail below, the control system of the surgical stapling system can be configured to sense the presence of the one or more implantable adjuncts attached to the jaws and adapt the operation of the surgical stapling system to account for the presence of the one or more implantable adjuncts. In various instances, an implantable adjunct can comprise a layer, a buttress, and/or a tissue thickness compensator, for example. The entire disclosure of U.S. Patent Application Publication No. 2009/0001122, entitled BUTTRESS AND STAPLING APPARATUS, filed on Jun. 27, 2007 is incorporated by reference herein. The entire disclosure of U.S. Patent Application Publication No. 2015/0374374, entitled STAPLE CARTRIDGE COMPRISING STAPLES POSITIONED WITHIN A COMPRESSIBLE PORTION THEREOF, filed on Jun. 29, 2015 is incorporated by reference herein. Referring to FIGS. 14 and 15, an end effector 14000 of a surgical stapling system comprises an anvil jaw 14100 and a staple cartridge jaw 14300. The anvil jaw 14100 is rotatable relative to the staple cartridge jaw 14300 between an open, unclamped, position and a closed, clamped, position; however, the staple cartridge jaw 14300 can be rotatable relative to the anvil jaw 14100 in other embodiments. The end effector 14000 further comprises sensors and sensing circuits in communication with the control system which detect whether an implantable adjunct is attached to the staple cartridge jaw 14300 and/or the anvil jaw 14100. The end effector 14000 comprises distal electrodes 14210 at the distal end of anvil jaw 14100 and proximal electrodes 14220 at the proximal end of the anvil jaw 14100. The end effector 14000 further comprises distal electrodes 14230 at the distal end of the staple cartridge jaw 14300 and proximal electrodes 14240 at the proximal end of the staple cartridge jaw 14300. In various instances, the distal anvil electrodes 14210 and the distal staple cartridge electrodes 14230 are part of a sensing circuit. When the anvil jaw 14100 is closed without tissue positioned between the anvil jaw 14100 and the staple cartridge jaw 14300, the distal anvil electrodes 14210 and the distal staple cartridge electrodes 14230 are brought into contact with one another if an implantable adjunct is not present between the anvil jaw 14100 and the staple cartridge jaw 14300. In such instances, the closure of the anvil jaw 14100 closes the sensing circuit. If, however, an implantable adjunct is positioned between the anvil jaw 14100 and the staple cartridge jaw 14300, the distal anvil electrodes 14210 do not directly contact the distal cartridge electrodes 14230 and, as a result, the resistance in the sensing circuit is higher. The control system is configured to operate in a first operating mode if it detects via the sensing circuit that an implantable adjunct is not present between the anvil jaw 14100 and the staple cartridge jaw 14300 and a second, or different, operating mode if it detects via the sensing circuit than an implantable adjunct is present between the anvil jaw 14100 and the staple cartridge jaw 14300. In one sense, the control system is configured to operate in a first operating mode if the sensing circuit impedance is below a threshold and a second operating mode if the sensing circuit impedance is above the threshold. A continuity curve 14700 is depicted in FIG. 16. The control system is in its first operating mode when the impedance in the sensing circuit is below a threshold 14710. The control system is in its second operating mode when the impedance in the sensing circuit is below a second threshold 14720 but not below the threshold 14710. When the impedance in the sensing circuit is above the second threshold 14720, the control system interprets such an event as the anvil jaw being in an open position. In various instances, the impedance in the sensing circuit may be different if more than one implantable adjunct is used as compared to when only one adjunct is used. In instances where the impedance in the sensing circuit exceeds a second threshold because of an additional implantable adjunct, the control system can operate in a third operating mode which is different that the first operating mode and the second operating mode.

Further to the above, referring again to FIGS. 14 and 15, the proximal anvil electrodes 14220 and the proximal cartridge electrodes 14240 are part of a second sensing circuit. The second sensing circuit works in the same way as the sensing circuit described above; however, the proximal anvil electrodes 14220 and the proximal cartridge electrodes 14240 do not come into direct contact with one another, regardless of whether an implantable adjunct is present in the end effector 14000. That said, the relative impedance between the proximal anvil electrodes 14220 and the proximal cartridge electrodes 14240 will change when one or more implantable adjuncts are attached to the end effector 14000 and the control system can detect this relative change via the second sensing circuit. Although the end effector 14000 comprises two sensing circuits, an end effector may comprise only one sensing circuit or more than two sensing circuits.

The above being said, any suitable sensing circuit can be used to detect the presence of an implantable adjunct attached to the anvil jaw and/or the staple cartridge jaw. In various instances, a sensing circuit can comprise one or more magnetic sensors configured to detect the presence of an implantable adjunct attached to the anvil jaw and/or the staple cartridge jaw. In at least one such instance, a magnetic sensor is positioned in the staple cartridge jaw and a magnetic element, such as a permanent magnet, for example, is positioned in the anvil jaw. When the anvil jaw is closed and an implantable adjunct is not positioned between the anvil jaw and the staple cartridge jaw, the magnetic element interferes with the magnetic field produced by the magnetic sensor and the distortion of this magnetic field is detected by the control system. When an implantable adjunct is positioned intermediate the anvil jaw and the staple cartridge jaw and the anvil jaw is closed, the implantable adjunct and the magnetic element distort the magnetic field of the magnetic sensor in a manner which is different than the magnetic element alone. As a result, the magnetic sensor produces a different voltage output when an implantable adjunct is present, as compared to when an implantable adjunct is not present, and the control system enters into the second operating mode upon detecting the different voltage output from the magnetic sensor. In addition to or in lieu of the above, a sensing circuit can comprise one or more optical sensors configured to detect the presence of an implantable adjunct attached to the anvil jaw and/or the staple cartridge jaw. In at least one such instance, an optical sensor is positioned in the staple cartridge jaw and the implantable adjunct comprises a discernably-different color than the anvil. Alternatively, the optical sensor is positioned in the anvil jaw and the implantable adjunct is a discernably different color than the staple cartridge. In either event, the optical sensor is in communication with the control system and is configured to produce a first signal when an implantable adjunct is not positioned in the end effector and a second, or different, signal when an implantable adjunct is positioned in the end effector. In at least one instance, the optical sensor comprises a RGB (red-green-blue) sensor with an IR (infra-red) filter, for example.

The sensors described above are capable of detecting an implantable adjunct on the anvil jaw and/or staple cartridge jaw before the end effector is positioned into the patient. In various instances, the end effector is opened and closed one or more times before the end effector is finally clamped onto the patient tissue. In such instances, the tissue does not block or impede the sensors from sensing whether an implantable adjunct is attached to the anvil jaw and/or the staple cartridge jaw. Graph 14800 in FIG. 16 depicts the jaw aperture between the anvil jaw and the staple cartridge jaw or, more specifically, the angle between the anvil jaw and the staple cartridge jaw when the end effector is being positioned in the patient and when the staple firing stroke is being performed. As seen in FIG. 16, the anvil jaw is moved between a fully-open position in which there is an approximately 20 degree angle between the anvil jaw and the staple cartridge jaw and a fully-closed position in which the anvil jaw and the staple cartridge jaw are parallel, or at least substantially parallel. Notably, the anvil jaw may be partially closed and/or partially opened several times to properly position the end effector in the patient. Also, notably, the end effector is completely closed during the staple firing stroke and then opened after the staple firing stroke has been performed to release the tissue.

The above being said, the patient tissue may block the above-discussed sensors from detecting one of the implantable adjuncts when the patient tissue is positioned between the anvil jaw and the staple cartridge jaw. For instance, the patient tissue can block a sensor on the anvil jaw from detecting an implantable adjunct on the staple cartridge jaw. Likewise, the patient tissue can block a sensor on the cartridge jaw from detecting an implantable adjunct on the anvil jaw. Some sensors, however, can detect the presence of an implantable adjunct on the other side of the tissue. In such instances, the control system is configured to discount the effect that the patient tissue has on the signals or voltage potentials generated by the sensors. In at least one such instance, the patient tissue between an anvil electrode and a staple cartridge electrode affects the impedance and/or continuity between the electrodes and the control system is nonetheless configured to assess the presence of one or more implantable adjuncts positioned between the electrodes.

In various instances, the anvil jaw includes a first IR sensor and the staple cartridge jaw includes a second IR sensor and which are configured to detect the heat of the patient tissue. The anvil IR sensor is configured to generate a first range of voltage potentials if an implantable adjunct is not attached to the anvil jaw and a second, or different, range of voltage potentials if an implantable adjunct is attached to the anvil jaw. Stated differently, the implantable adjunct will at least partially block the heat from the patient tissue that is measured by the anvil IR sensor which affects the signal generated by the anvil IR sensor. The anvil IR sensor is in signal communication with the control system via a conductor and/or a wireless signal transmitter/receiver arrangement and, when the voltage potential is in the second range of voltage potentials, the control system determines that an implantable adjunct on the anvil is present. The cartridge IR sensor is configured to generate a first range of voltage potentials if an implantable adjunct is not attached to the staple cartridge jaw and a second, or different, range of voltage potentials if an implantable adjunct is attached to the staple cartridge jaw. Stated differently, the implantable adjunct will at least partially block the heat from the patient tissue that is measured by the cartridge IR sensor which affects the signal generated by the cartridge IR sensor. The cartridge IR sensor is in signal communication with the control system via a conductor and/or a wireless signal transmitter/receiver arrangement and, when the voltage potential is in the second range of voltage potentials, the control system determines that an implantable adjunct on the staple cartridge is present.

Regardless of the manner in which the control system determines that an implantable adjunct is present in the end effector, the control system, in various instances, is configured to modify the operation of the surgical stapling system when it detects that an implantable adjunct is present in the end effector. For instance, the control system can slow the speed in which the anvil jaw is closed when an implantable adjunct is present on the anvil jaw and/or the staple cartridge jaw as compared to when an implantable adjunct is not present in the end effector. In at least one such instance, the control system operates the closure drive motor at a first slower speed when the control system detects one implantable adjunct in the end effector and at a second slower speed-slower than the first slower speed-when the control system detects two implantable adjuncts in the end effector. In addition to or in lieu of the above, referring to FIG. 16, the control system is configured to slow the staple firing stroke when the control system detects one or more implantable adjuncts in the end effector as compared to when the control system does not detect an implantable adjunct in the end effector. The slower speed of the staple firing stroke can be seen when comparing the jaw opening/closing curve 14800 (no implantable adjunct detected) to the alternative jaw opening/closing curve 14800' (implantable adjunct detected) as the jaw remains closed for a longer period of time in the curve 14800'. In at least one such instance, the control system operates the firing drive motor at a first slower speed when the control system detects one implantable adjunct in the end effector and at a second slower speed-slower than the first slower speed-when the control system detects two implantable adjuncts in the end effector. In addition to or in lieu of the above, referring again to FIG. 16, the control system is configured to increase the current to the firing drive motor to increase the force applied to the firing member during the staple firing stroke. The higher force of the staple firing stroke can be seen when comparing the force curve 14400 (no implantable adjunct detected) to the alternative force curve 14400' (implantable adjunct detected). Notably, the duration in which the force is applied has also increased in the force curve 14400' owing to a slower staple firing stroke. In addition to or in lieu of the above, the control system is configured to increase the clamping force applied to the patient tissue when an implantable adjunct is present in the end effector as compared to when an implantable adjunct is not present in the end effector. In such instances, the control system can position the anvil jaw closer to the staple cartridge jaw when an adjunct is present in the end effector. In various instances, an implantable adjunct may be slippery or have a low coefficient of friction on its surface which can tend to permit larger tissue flows during a staple firing stroke and, thus, clamping harder on the tissue in such instances can reduce the tissue flow.

As discussed above, the end effector of a surgical stapling system is clamped onto the tissue of a patient and the staple firing drive is then operated to staple and incise the tissue. When the end effector is initially clamped onto the tissue, depending on the thickness of the tissue being clamped, the jaws of the end effector may flex and/or otherwise be loaded in a manner which prevents the jaws from being in a perfect, or parallel, alignment to one another. That said, once the tissue is clamped, fluid within the clamped tissue may begin to flow laterally and/or longitudinally into the surrounding connected tissue that is unclamped. In such instances, the tissue captured between the end effector jaws becomes thinner, or at least slightly thinner, over the 10-15 seconds following the initial clamping which allows the jaws to move into alignment, or at least closer to alignment, with one another. With this in mind, the control system of a surgical stapling system comprises a timer circuit configured to count the time after the end effector has been clamped onto the tissue. The control system is in communication with a display and/or indicator of the surgical stapling system and, when the timer circuit has counted a predetermined amount of time, such as 10 seconds, for example, the control system activates the display and/or indicator to indicate to the clinician that the surgical stapling system is ready to perform a staple firing stroke. That said, the staple firing drive is actuatable by a clinician prior to the display and/or indicator being actuated. Such an arrangement does not prevent the clinician from performing an action urgently, if needed. That said, the staple firing stroke can be prevented if there is something wrong with the surgical stapling system. For instance, the staple firing stroke can be prevented if the staple cartridge positioned in the end effector has already been at least partially spent and/or if the anvil jaw has not sufficiently closed to perform the staple firing stroke, for example. The entire disclosures of U.S. Pat. No. 7,143,923, entitled SURGICAL STAPLING INSTRUMENT HAVING A FIRING LOCKOUT FOR AN UNCLOSED ANVIL, which issued on Dec. 5, 2006; U.S. Pat. No. 7,044,352, SURGICAL STAPLING INSTRUMENT HAVING A SINGLE LOCKOUT MECHANISM FOR PREVENTION OF FIRING, which issued on May 16, 2006; U.S. Pat. No. 7,000,818, SURGICAL STAPLING INSTRUMENT HAVING SEPARATE DISTINCT CLOSING AND FIRING SYSTEMS, which issued on Feb. 21, 2006; U.S. Pat. No. 6,988,649, SURGICAL STAPLING INSTRUMENT HAVING A SPENT CARTRIDGE LOCKOUT, which issued on Jan. 24, 2006; and U.S. Pat. No. 6,978,921, SURGICAL STAPLING INSTRUMENT INCORPORATING AN E-BEAM FIRING MECHANISM, which issued on Dec. 27, 2005, are incorporated by reference herein.

In many instances, further to the above, actuating the staple firing drive early, i.e., prior to the ready-to-fire indicator being actuated, produces satisfactory staple forms; however, malformed staples may occur in such instances because the end effector jaws may not have reached their final position prior to the staple firing stroke being initiated. As discussed above, the control systems disclosed herein are capable of evaluating whether the staples are being properly formed or malformed. If the control system detects that the staple firing stroke was started early and then detects that one or more staples have been malformed, the control system can slow the staple firing stroke until the predetermined time has elapsed and then return the stapling firing stroke to its normal speed. In other embodiments, the control system is configured to return the staple firing stroke back to its normal speed after the predetermined time has elapsed and the staples are no longer being malformed. That said, any suitable algorithm can be used to adjust the operation of the surgical stapling system during a staple firing stroke to produce satisfactory staple forms if the staple firing stroke is started early.

In various instances, further to the above, the control system is configured to pause the staple firing stroke if the control system detects that staples are being malformed. In such instances, the fluid in the clamped tissue will be given more time to flow into the adjacent tissue and, as a result, the jaws may become better aligned for the remainder of the staple firing stroke and the occurrence of malformed staples can be reduced. After the pause time has elapsed, the control system restarts the staple firing stroke and continues to monitor for malformed staples. The control system comprises a timer circuit configured to count time until the predetermined pause time has been reached, which is approximately 2 seconds, for example. In other instances, the predetermined pause time can be 1 second, 3 seconds, or 5 seconds, for example. In the event that the control system detects that more staples are being malformed after the staple firing stroke recommences, the control system is configured to pause the staple firing stroke once again. Similar to the above, the control system restarts the staple firing stroke after the predetermined pause time has elapsed. In at least one alternative embodiment, the second pause time is longer than the first pause time. In any event, the control system is configured to pause the staple firing stroke any suitable number of times. That said, alternative embodiments are envisioned in which the clinician is required to re-start the staple firing stroke after the staple firing stroke has been paused. Such embodiments may be preferable to clinicians who prefer that their surgical instruments do not perform automatic actions. The entire disclosure of U.S. Pat. No. 8,499,992, entitled DEVICE AND METHOD FOR CONTROLLING COMPRESSION OF TISSUE, issued on Aug. 6, 2013, is incorporated by reference herein.

In addition to or in lieu of the above, the control system is configured to adjust the predetermined wait time from one firing stroke to another. In at least one instance, the control system is configured to evaluate if one or more malformed staples were created in the beginning part of a first staple firing stroke even though the staple firing stroke was initiated after the predetermined wait time had elapsed. If the number of malformed staples at the beginning of the first staple firing stroke exceeds a predetermined amount, such as one malformed staple or two malformed staples, for example, the control system increases the predetermined wait time for the second staple firing stroke. In at least one such instance, the control system increases the predetermined wait time from 10 seconds to 12 seconds, for example. If the number of malformed staples at the beginning of the second staple firing stroke, or any subsequent staple firing stroke, exceeds the predetermined amount, the control system increases the predetermined wait time for the next staple firing stroke. In at least one such instance, the control system increases the predetermined wait time from 12 seconds to 15 seconds, for example.

Many of the examples provided herein were discussed in connection with a surgical stapling system; however, the teachings provided herein can be adapted to any suitable surgical system such as, for example, an ultrasonic surgical instrument configured to seal and/or cut patient tissue using a standing vibrational wave and/or an RF surgical instrument configured to seal and/or cut patient tissue using electrical energy.

Examples of ultrasonic surgical instruments include the HARMONIC ACER Ultrasonic Shears, the HARMONIC WAVER Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled CLAMP COAGULATOR/CUTTING SYSTEM FOR ULTRASONIC SURGICAL INSTRUMENTS, issued on Jun. 21, 1994, the disclosure of which is incorporated by reference herein; U.S. Pat. No. 5,873,873, entitled ULTRASONIC CLAMP COAGULATOR APPARATUS HAVING IMPROVED CLAMP MECHANISM, issued on Feb. 23, 1999, the disclosure of which is incorporated by reference herein; U.S. Pat. No. 5,980,510, entitled ULTRASONIC CLAMP COAGULATOR APPARATUS HAVING IMPROVED CLAMP ARM PIVOT MOUNT, issued on Nov. 9, 1999, the disclosure of which is incorporated by reference herein; U.S. Pat. No. 6,325,811, entitled BLADES WITH FUNCTIONAL BALANCE ASYMMETRIES FOR USE WITH ULTRASONIC SURGICAL INSTRUMENTS, issued on Dec. 4, 2001, the disclosure of which is incorporated by reference herein; U.S. Pat. No. 6,773,444, entitled BLADES WITH FUNCTIONAL BALANCE ASYMMETRIES FOR USE WITH ULTRASONIC SURGICAL INSTRUMENTS, issued on Aug. 10, 2004, the disclosure of which is incorporated by reference herein; and U.S. Pat. No. 6,783,524, entitled ROBOTIC SURGICAL TOOL WITH ULTRASOUND CAUTERIZING AND CUTTING INSTRUMENT, issued on Aug. 31, 2004, the disclosure of which is incorporated by reference herein.

Still further examples of ultrasonic surgical instruments are disclosed in U.S. Patent Application Publication No. 2006/0079874, entitled TISSUE PAD FOR USE WITH AN ULTRASONIC SURGICAL INSTRUMENT, published on Apr. 13, 2006, the disclosure of which is incorporated by reference herein; U.S. Patent Application Publication No. 2007/0191713, entitled ULTRASONIC DEVICE FOR CUTTING AND COAGULATING, published on Aug. 16, 2007, the disclosure of which is incorporated by reference herein; U.S. Patent Application Publication No. 2007/0282333, entitled ULTRASONIC WAVEGUIDE AND BLADE, published on Dec. 6, 2007, the disclosure of which is incorporated by reference herein; U.S. Patent Application Publication No. 2008/0200940, entitled ULTRASONIC DEVICE FOR CUTTING AND COAGULATING, published on Aug. 21, 2008, the disclosure of which is incorporated by reference herein; U.S. Patent Application Publication No. 2009/0105750, entitled ERGONOMIC SURGICAL INSTRUMENTS, published on Apr. 23, 2009, issued as U.S. Pat. No. 8,623,027 on Jan. 7, 2014, the disclosure of which is incorporated by reference herein; U.S. Patent Application Publication No. 2010/0069940, entitled ULTRASONIC DEVICE FOR FINGERTIP CONTROL, published on Mar. 18, 2010, issued as U.S. Pat. No. 9,023,071 on May 5, 2015, the disclosure of which is incorporated by reference herein; and U.S. Patent Application Publication No. 2011/0015660, entitled ROTATING TRANSDUCER MOUNT FOR ULTRASONIC SURGICAL INSTRUMENTS, published on Jan. 20, 2011, issued as U.S. Pat. No. 8,461,744 on Jun. 11, 2013, the disclosure of which is incorporated by reference herein; and U.S. Patent Application Publication No. 2012/0029546, entitled ULTRASONIC SURGICAL INSTRUMENT BLADES, published on Feb. 2, 2012, the disclosure of which is incorporated by reference herein.

Some of ultrasonic surgical instruments may include a cordless transducer such as that disclosed in U.S. Patent Application Publication No. 2012/0112687, entitled RECHARGE SYSTEM FOR MEDICAL DEVICES, published on May 10, 2012, issued as U.S. Pat. No. 9,381,058 on Jul. 5, 2016, the disclosure of which is incorporated by reference herein; U.S. Patent Application Publication No. 2012/0116265, entitled SURGICAL INSTRUMENT WITH CHARGING DEVICES, published on May 10, 2012, the disclosure of which is incorporated by reference herein; and/or U.S. Patent Application Ser. No. 61/410,603, filed on Nov. 5, 2010, entitled ENERGY-BASED SURGICAL INSTRUMENTS, the disclosure of which is incorporated by reference herein.

Additionally, some ultrasonic surgical instruments may include an articulating shaft section. Examples of such ultrasonic surgical instruments are disclosed in U.S. patent application Ser. No. 13/538,588, filed on Jun. 29, 2012, entitled SURGICAL INSTRUMENTS WITH ARTICU-LATING SHAFTS, issued as U.S. Pat. No. 9,393,037 on Jul. 19, 2016, the disclosure of which is incorporated by reference herein; and U.S. patent application Ser. No. 13/657,553, filed on Oct. 22, 2012, entitled FLEXIBLE HARMONIC WAVEGUIDES/BLADES FOR SURGICAL INSTRUMENTS, issued as U.S. Pat. No. 9,095,367 on Aug. 4, 2015, the disclosure of which is incorporated by reference herein.

In various circumstances, a surgical instrument can be configured to apply energy to tissue in order to treat and/or destroy the tissue. In certain circumstances, a surgical instrument can comprise one or more electrodes which can be positioned against and/or positioned relative to the tissue such that electrical current can flow from one electrode, through the tissue, and to the other electrode. The surgical instrument can comprise an electrical input, a supply conductor electrically coupled with the electrodes, and/or a return conductor which can be configured to allow current to flow from the electrical input, through the supply conductor, through the electrodes and the tissue, and then through the return conductor to an electrical output, for example. Alternatively, the surgical instrument can comprise an electrical input, a supply conductor electrically coupled with the electrodes, and/or a return conductor which can be configured to allow current to flow from the electrical input, through the supply conductor, through the active electrode and the tissue, and to the return electrode through the return conductor to an electrical output. In various circumstances, heat can be generated by the current flowing through the tissue, wherein the heat can cause one or more haemostatic seals to form within the tissue and/or between tissues. Such embodiments may be particularly useful for sealing blood vessels, for example. The surgical instrument can also comprise a cutting member that can be moved relative to the tissue and the electrodes in order to transect the tissue.

By way of example, energy applied by a surgical instrument may be in the form of radio frequency ("RF") energy. RF energy is a form of electrical energy that may be in the frequency range of 300 kilohertz (kHz) to 1 megahertz (MHz). In application, RF surgical instruments transmit low frequency radio waves through electrodes, which cause ionic agitation, or friction, in effect resistive heating, increasing the temperature of the tissue. Since a sharp boundary is created between the affected tissue and that surrounding it, surgeons can operate with a high level of precision and control, without much sacrifice to the adjacent normal tissue. The low operating temperatures of RF energy enables surgeons to remove, shrink or sculpt soft tissue while simultaneously sealing blood vessels. RF energy works particularly well on connective tissue, which is primarily comprised of collagen and shrinks when contacted by heat.

Further, in various open and laparoscopic surgeries, it is necessary to coagulate, seal or fuse tissues. One preferred means of tissue-sealing relies upon the application of electrical energy to captured tissue to cause thermal effects therein for sealing purposes. Various mono-polar and bi-polar RF jaw structures have been developed for such purposes. In general, the delivery of RF energy to a captured tissue volume elevates the tissue temperature and thereby at least partially denatures proteins in the tissue. Such proteins, including collagen, are denatured into a pertinacious amalgam that intermixes and fuses together as the proteins denature or form new cross links. As the treated region heals over time, this biological "weld" is reabsorbed by the body's wound healing process.

In a basic bi-polar RF jaw arrangement, each face of opposing first and second jaws comprises an electrode and RF current flows across the captured tissue between the opposing polarity electrodes. Such prior art RF jaws that engage opposing sides of tissue typically cannot cause uniform thermal effects in the tissue-whether the captured tissue is thin or substantially thick. As RF energy density in tissue increases, the tissue surface becomes desiccated and resistant to additional ohmic heating. Localized tissue desiccation and charring can occur almost instantly as tissue impedance rises, which then can result in a non-uniform seal in the tissue. The typical prior art RF jaws can cause further undesirable effects by propagating RF density laterally from the engaged tissue thus causing unwanted collateral thermal damage.

The commercially available RF sealing instruments typically use one of two approaches to "control" RF energy delivery in tissue. In a first "power adjustment" approach, the RF system controller can rapidly adjust the level of total power delivered to the jaws' engagement surfaces in response to feedback circuitry coupled to the active electrodes that measures tissue impedance or electrode temperature. In a second "current-path directing" approach, the instrument jaws carry an electrode arrangement in which opposing polarity electrodes are spaced apart by an insulator material—which may cause current to flow within an extended path through captured tissue rather than simply between surfaces of the first and second jaws. Electrosurgical grasping instruments having jaws with electrically-isolated electrode arrangements in cooperating jaws faces were proposed by Yates et al. in U.S. Pat. Nos. 5,403,312; 5,735,848 and 5,833,690. The entire disclosure of U.S. Pat. Nos. 5,403,312; 5,735,848 and 5,833,690 are incorporated by reference herein.

In various embodiments, further to the above, a tissue cutting knife comprises a sharp cutting edge. In certain instances, the tissue cutting knife can be energized with electrical energy to improve the tissue cutting mechanics and/or improve the tissue sealing. In at least one instance, a voltage potential from a power source is applied to the tissue cutting knife, or at least the metal cutting edge of the tissue cutting knife, such that electrical current flows through the tissue cutting knife, through the tissue captured between the end effector jaws, and then into one or both of the end effector jaws as part of a return path in the electrical circuit. Such an instrument can be referred to as a bipolar instrument. That said, monopolar instruments are also envisioned. In such embodiments, a return path for the electrical current is provided through a grounding pad, for example, that the patient is in contact with on the operating table. In any event, an energized tissue cutting knife can be used in a surgical stapling system and/or an RF surgical system, for example, among others.

Further to the above, a control system of a surgical stapling system can be configured to modify or change the voltage potential and/or power supplied to the tissue cutting knife as a result of one or more parameters sensed by the control system during a previous staple firing stroke and/or during a current staple firing stroke. For instance, the control system is configured to increase the magnitude of the voltage being applied to the tissue cutting knife when one or more implantable adjuncts are present in the end effector. In at least one such instance, the voltage potential is applied to the tissue cutting knife as a voltage waveform and the peaks of the voltage waveform are increased when an implantable adjunct is being transected during the staple firing stroke. As such, the control system comprises a first operating mode for when an implantable adjunct is not detected in the end effector and a second operating mode for when an implantable adjunct is detected in the end effector. In various instances, the second operating mode is used when only one implantable adjunct is detected and a third operating mode is used when more than one implantable adjunct is detected. The peaks of the voltage waveform in the third operating mode are higher than the peaks of the waveforms in the first operating mode and the second operating mode.

Further to the above, the control system can be configured to change the magnitude of the voltage waveform during the staple firing stroke in response to a triggering event. For instance, the control system can increase the magnitude of the voltage waveform when the control system detects that a staple has been malformed. In at least one such instance, the control system increases the magnitude of the waveform after a predetermined number of staples have been malformed during the staple firing stroke. The predetermined number can be one staple or more than one staple.

Figure 19:
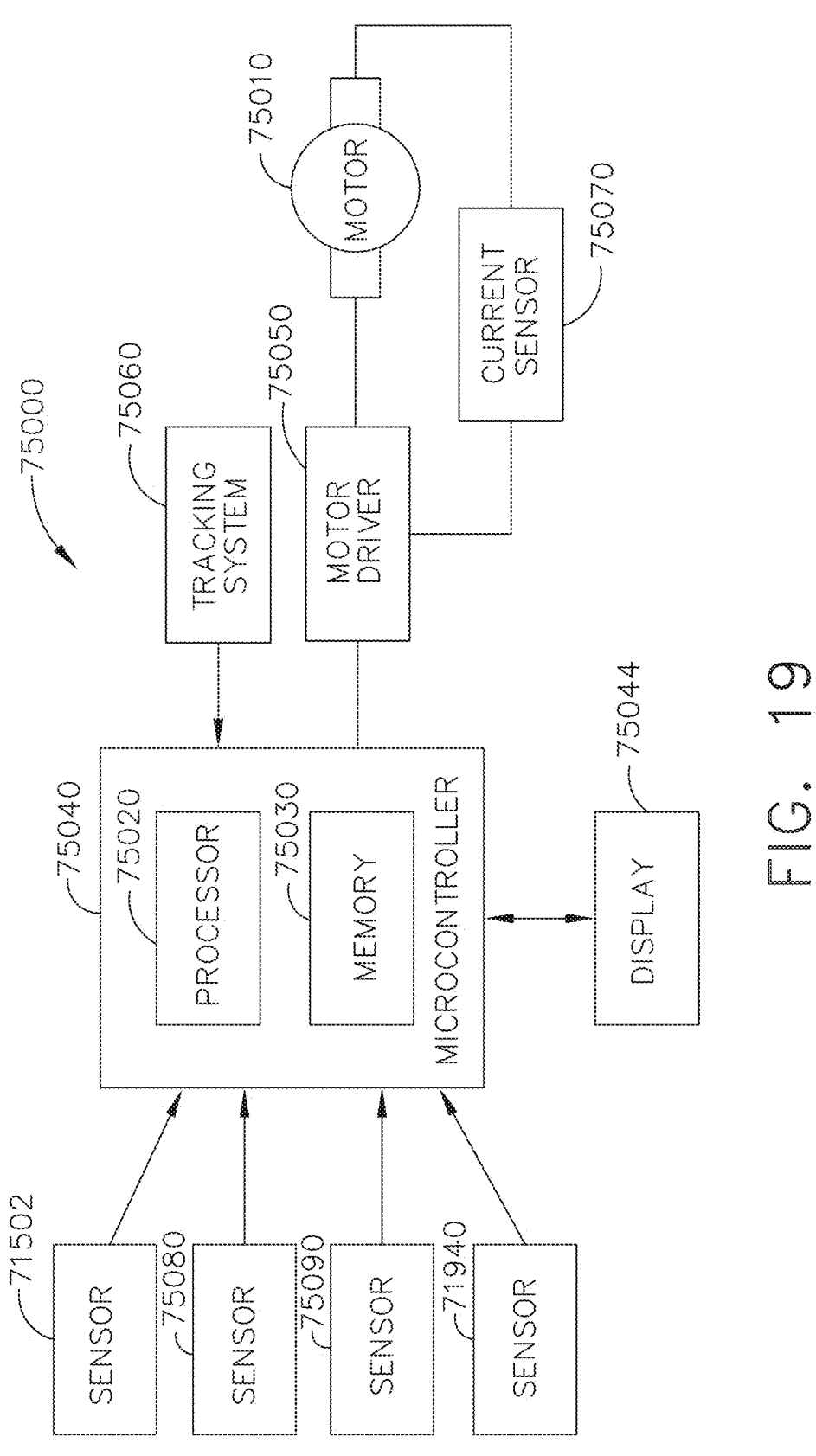
FIG. 19 is a schematic of a control system for use with any of the surgical instruments disclosed herein.

FIG. 19 is a logic diagram of a control system 75000 for use with any of the various surgical instruments described herein. The control system 75000 comprises a control circuit. The control circuit includes a microcontroller 75040 comprising a processor 75020 and a memory 75030. One or more sensors, such as sensor 75080, sensor 75090, sensor 71502, and sensor array 71940, for example, provide real time feedback to the processor 75020. The control system 75000 further comprises a motor driver 75050 configured to control an electric motor 75010 and a tracking system 75060 configured to determine the position of one or more longitudinally movable components in the surgical instrument. The tracking system 75060 is also configured to determine the position of one or more rotational components in the surgical instrument. The tracking system 75060 provides position information to the processor 75020, which can be programmed or configured to determine the position of one or more components. The motor driver 75050 may be an A3941 available from Allegro Microsystems, Inc., for example; however, other motor drivers may be readily substituted for use in the tracking system 75060. A detailed description of an absolute positioning system is described in U.S. Patent Application Publication No. 2017/0296213, entitled SYSTEMS AND METHODS FOR CONTROLLING A SURGICAL STAPLING AND CUTTING INSTRUMENT, the entire disclosure of which is incorporated herein by reference.

The microcontroller 75040 may be any single core or multicore processor such as those known under the trade name ARM Cortex by Texas Instruments, for example. In at least one instance, the microcontroller 75040 is a LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EE-PROM), one or more pulse width modulation (PWM) modules and/or frequency modulation (FM) modules, one or more quadrature encoder inputs (QEI) analog, one or more 12-bit Analog-to-Digital Converters (ADC) with 12 analog input channels, for example, details of which are available from the product datasheet.

In various instances, the microcontroller 75040 comprises a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 75040 is programmed to perform various functions such as precisely controlling the speed and/or position of the staple firing member or closure tube, for example. The microcontroller 75040 is also programmed to precisely control the rotational speed and position of the end effector of surgical instrument and the articulation speed and position of the end effector in various embodiments. In various instances, the microcontroller 75040 computes a response in the software of the microcontroller 75040. The computed response is compared to a measured response of the actual system to obtain an "observed" response, which is used for actual feedback decisions. The observed response is a favorable, tuned, value that balances the smooth, continuous nature of the simulated response with the measured response, which can detect outside influences on the system.

The motor 75010 is controlled by the motor driver 75050. In various forms, the motor 75010 is a DC brushed driving motor having a maximum rotational speed of approximately 25,000 RPM, for example. In other arrangements, the motor 75010 includes a brushless motor, a cordless motor, a synchronous motor, a stepper motor, or any other suitable electric motor. The motor driver 75050 may comprise an H-bridge driver comprising field-effect transistors (FETs), for example. The motor driver 75050 may be an A3941 available from Allegro Microsystems, Inc., for example. The A3941 motor driver 75050 is a full-bridge controller for use with external N-channel power metal oxide semiconductor field effect transistors (MOSFETs) specifically designed for inductive loads, such as brush DC motors. In various instances, the motor driver 75050 comprises a unique charge pump regulator provides full (>10 V) gate drive for battery voltages down to 7 V and allows the A3941 motor driver 75050 to operate with a reduced gate drive, down to 5.5 V. A bootstrap capacitor may be employed to provide the above-battery supply voltage required for N-channel MOS-FETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor adjustable dead time. Integrated diagnostics provide indication of undervoltage, overtemperature, and power bridge faults, and can be configured to protect the power MOSFETs under most short circuit conditions. Other motor drivers may be readily substituted.

The tracking system 75060 comprises a controlled motor drive circuit arrangement comprising one or more position sensors, such as the sensor 75080, sensor 75090, sensor 71502, and sensor array 71940, for example. The position sensors for an absolute positioning system provide a unique position signal corresponding to the location of a displacement member. As used herein, the term displacement member is used generically to refer to any movable member of any of the surgical instruments disclosed herein. In various instances, the displacement member may be coupled to any position sensor suitable for measuring linear displacement or rotational displacement. Linear displacement sensors may include contact or non-contact displacement sensors. The displacement sensors may comprise linear variable differential transformers (LVDT), differential variable reluctance transducers (DVRT), a slide potentiometer, a magnetic sensing system comprising a movable magnet and a series of linearly arranged Hall Effect sensors, a magnetic sensing system comprising a fixed magnet and a series of movable linearly arranged Hall Effect sensors, an optical sensing system comprising a movable light source and a series of linearly arranged photo diodes or photo detectors, or an optical sensing system comprising a fixed light source and a series of movable linearly arranged photo diodes or photo detectors, or any combination thereof.

The position sensors 75080, 75090, 71502, and 71940 for example, may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-Effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

In various instances, one or more of the position sensors of the tracking system 75060 comprise a magnetic rotary absolute positioning system. Such position sensors may be implemented as an AS5055EQFT single-chip magnetic rotary position sensor available from Austria Microsystems, AG and can be interfaced with the controller 75040 to provide an absolute positioning system. In certain instances, a position sensor comprises a low-voltage and low-power component and includes four Hall-Effect elements in an area of the position sensor that is located adjacent a magnet. A high resolution ADC and a smart power management controller are also provided on the chip. A CORDIC processor (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface such as an SPI interface to the controller 75040. The position sensors can provide 12 or 14 bits of resolution, for example. The position sensors can be an AS5055 chip provided in a small QFN 16-pin 4×4×0.85 mm package, for example.

The tracking system 75060 may comprise and/or be programmed to implement a feedback controller, such as a PID, state feedback, and adaptive controller. A power source converts the signal from the feedback controller into a physical input to the system, in this case voltage. Other examples include pulse width modulation (PWM) and/or frequency modulation (FM) of the voltage, current, and force. Other sensor(s) may be provided to measure physical parameters of the physical system in addition to position. In various instances, the other sensor(s) can include sensor arrangements such as those described in U.S. Pat. No. 9,345,481, entitled STAPLE CARTRIDGE TISSUE THICKNESS SENSOR SYSTEM, which is hereby incorporated herein by reference in its entirety; U.S. Patent Application Publication No. 2014/0263552, entitled STAPLE CARTRIDGE TISSUE THICKNESS SENSOR SYSTEM, which is hereby incorporated herein by reference in its entirety; and U.S. Patent Application Ser. No. 15/628, 175, entitled TECHNIQUES FOR ADAPTIVE CONTROL OF MOTOR VELOCITY OF A SURGICAL STAPLING AND CUTTING INSTRUMENT, which is hereby incorporated herein by reference in its entirety. In a digital signal processing system, the absolute positioning system is coupled to a digital data acquisition system where the output of the absolute positioning system will have finite resolution and sampling frequency. The absolute positioning system may comprise a compare and combine circuit to combine a computed response with a measured response using algorithms such as weighted average and theoretical control loop that drives the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power up of the instrument without retracting or advancing the displacement member to a reset (zero or home) position as may be required with conventional rotary encoders that merely count the number of steps forwards or backwards that the motor 75010 has taken to infer the position of a device actuator, a firing member, a feeder drive, a crimping drive, a closure tube, and the like.

A sensor 75080 comprising a strain gauge or a micro-strain gauge, for example, is configured to measure one or more parameters of the end effector of the surgical instrument, such as, for example, the strain experienced by the jaws and/or staple firing member during a staple firing stroke. The measured strain is converted to a digital signal and provided to the processor 75020. In addition to or in lieu of the sensor 75080, a sensor 75090 comprising a load sensor, for example, can measure the closure force applied by the closure drive system to the jaws of the surgical instrument. In various instances, a current sensor 75070 can be employed to measure the current drawn by the motor 75010. The force required to clamp the first and second jaws and/or fire the staple cartridge can correspond to the current drawn by the motor 75010, for example. The measured force is converted to a digital signal and provided to the processor 75020. A magnetic field sensor can be employed to measure the thickness of the captured tissue. The measurement of the magnetic field sensor can also be converted to a digital signal and provided to the processor 75020.

The measurements of the tissue compression, the tissue thickness, and/or the force required to close the end effector and/or perform the staple firing stroke as measured by the sensors can be used by the controller 75040 to characterize the position and/or speed of the movable member being tracked. In at least one instance, the memory 75030 may store a technique, an equation, and/or a look-up table which can be employed by the controller 75040 in the assessment. In various instances, the controller 75040 can provide the user of the surgical instrument with a choice as to the manner in which the surgical instrument should be operated. To this end, a display 75044 can display a variety of operating conditions of the surgical instrument and can include touch screen functionality for data input. Moreover, information displayed on the display 75044 may be overlaid with images acquired via the imaging modules of one or more endoscopes and/or one or more additional surgical instruments used during the surgical procedure.

As discussed above, the surgical instruments disclosed herein may comprise control systems. Each of the control systems can comprise a circuit board having one or more processors and/or memory devices. Among other things, the control systems are configured to store sensor data, for example. They are also configured to store data which identifies the type of staple cartridge attached to a stapling instrument, for example. More specifically, the type of staple cartridge can be identified when attached to the stapling instrument by the sensors and the sensor data can be stored in the control system. This information can be obtained by the control system to assess whether or not the staple cartridge is suitable for use.

The surgical instrument systems described herein are motivated by an electric motor; however, the surgical instrument systems described herein can be motivated in any suitable manner. In certain instances, the motors disclosed herein may comprise a portion or portions of a robotically controlled system. U.S. patent application Ser. No. 13/118, 241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail, the entire disclosure of which is incorporated by reference herein. The disclosures of International Patent Publication No. WO 2017/083125, entitled STAPLER WITH COMPOSITE CARDAN AND SCREW DRIVE, published May 18, 2017, International Patent Publication No. WO 2017/083126, entitled STAPLE PUSHER WITH LOST MOTION BETWEEN RAMPS, published May 18, 2017, International Patent Publication No. WO 2015/153642, entitled SURGICAL INSTRU-MENT WITH SHIFTABLE TRANSMISSION, published Oct. 8, 2015, U.S. Patent Application Publication No. 2017/0265954, filed Mar. 17, 2017, entitled STAPLER WITH CABLE-DRIVEN ADVANCEABLE CLAMPING ELE-MENT AND DUAL DISTAL PULLEYS, U.S. Patent Appli-cation Publication No. 2017/0265865, filed Feb. 15, 2017, entitled STAPLER WITH CABLE-DRIVEN ADVANCE-ABLE CLAMPING ELEMENT AND DISTAL PULLEY, and U.S. Patent Application Publication No. 2017/0290586, entitled STAPLING CARTRIDGE, filed on Mar. 29, 2017, are incorporated herein by reference in their entireties.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise elec-trodes configured to heat and seal the tissue. Also, for instance, an end effector in accordance with certain embodi-ments can apply vibrational energy to seal the tissue.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRU-MENT WITH TACTILE POSITION FEEDBACK, which issued on Sep. 9, 2008;

U.S. Pat. No. 7,464,849, entitled ELECTRO-MECHANI-CAL SURGICAL INSTRUMENT WITH CLOSURE SYSTEM AND ANVIL ALIGNMENT COMPO-NENTS, which issued on Dec. 16, 2008;

U.S. Pat. No. 7,670,334, entitled SURGICAL INSTRU-MENT HAVING AN ARTICULATING END EFFEC-TOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORI-ENTABLE IMPLANTABLE FASTENER CAR-TRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRU-MENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRU-MENT, now U.S. Pat. No. 8,210,411;

U.S. patent application Ser. No. 12/235,972, entitled MOTORIZED SURGICAL INSTRUMENT, now U.S. Pat. No. 9,050,083;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRU-MENT WITH ELECTRIC ACTUATOR DIREC-TIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGE-MENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SEN-SOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SEN-SOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCK-ING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Par-ticular features, structures, or characteristics may be com-bined in any suitable manner in one or more embodiments. Thus, the particular features, structures, or characteristics illustrated or described in connection with one embodiment may be combined in whole or in part, with the features, structures or characteristics of one ore more other embodi-ments without limitation. Also, where materials are dis-closed for certain components, other materials may be used. Furthermore, according to various embodiments, a single component may be replaced by multiple components, and multiple components may be replaced by a single compo-nent, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

What is claimed is:

1. A surgical instrument, comprising:
a first jaw;
a second jaw, wherein said first jaw is movable toward said second jaw from an unclamped position to a clamped position during a jaw closure stroke;
a closure system, comprising:
a closure motor; and
a closure member drivable by said closure motor, wherein said closure member is movable through said jaw closure stroke by said closure motor to move said first jaw into said clamped position and apply clamping pressure to tissue captured between said first jaw and said second jaw;
a tissue cutting system, comprising:
a drive motor; and
a cutting member drivable by said drive motor, wherein said cutting member is movable through a tissue cutting stroke by said drive motor to cut the tissue captured between said first jaw and said second jaw after said first jaw has been moved into said clamped position;
a sensor circuit comprising a first electrode positioned on said first jaw and a second electrode positioned on said second jaw, wherein said first electrode and said second electrode are configured to contact each other when said first jaw is in said clamped position and an implantable adjunct is not positioned intermediate said first jaw and said second jaw, and wherein said first electrode and said second electrode are separated from each other when said first jaw is in said clamped position and an implantable adjunct is positioned intermediate said first jaw and said second jaw; and a motor control system in communication with said closure motor, said drive motor, and said sensor circuit, wherein said motor control system is configured to control the operation of said closure motor and said drive motor, and wherein said motor control system is configured to increase the clamping pressure applied by said first jaw during said tissue cutting stroke when said sensor circuit detects the presence of an implantable adjunct intermediate said first jaw and said second jaw.

2. The surgical instrument of claim 1, further comprising a staple cartridge positioned in said first jaw, wherein said staple cartridge comprises:
a cartridge body;
staples removably stored in said cartridge body; and
an implantable adjunct removably attached to said cartridge body.

3. The surgical instrument of claim 1, further comprising a staple cartridge positioned in said second jaw, wherein said staple cartridge comprises:
a cartridge body;
staples removably stored in said cartridge body; and
an implantable adjunct removably attached to said cartridge body.

4. The surgical instrument of claim 1, further comprising an implantable adjunct releasably attached to said first jaw.

5. The surgical instrument of claim 1, further comprising an implantable adjunct releasably attached to said second jaw.

6. The surgical instrument of claim 1, wherein said motor control system is configured to decrease a speed of said drive motor when said jaw closure stroke is increased.

7. The surgical instrument of claim 6, wherein said motor control system comprises a pulse width modulation circuit configured to control the speed of said drive motor.

8. The surgical instrument of claim 1, wherein said sensor circuit comprises an electrode configured to contact the implantable adjunct.

9. The surgical instrument of claim 8, wherein said electrode is positioned on said first jaw.

10. The surgical instrument of claim 1, wherein said sensor circuit comprises an electrode configured to be positioned near the implantable adjunct.

11. The surgical instrument of claim 10, wherein said first jaw comprises an anvil including staple forming pockets, and wherein said electrode is positioned in a said staple forming pocket.

12. A surgical instrument, comprising: a first jaw;
a second jaw, wherein said first jaw is movable toward said second jaw from an unclamped position to a clamped position during a jaw closure stroke;
a closure system, comprising:
a closure motor; and
a closure member drivable by said closure motor, wherein said closure member is movable through said jaw closure stroke by said closure motor to move said first jaw into said clamped position and apply clamping pressure to tissue captured between said first jaw and said second jaw;
a tissue cutting system, comprising:
a drive motor; and
a cutting member drivable by said drive motor, wherein said cutting member is movable through a tissue cutting stroke by said drive motor to cut the tissue captured between said first jaw and said second jaw after said first jaw has been moved into said clamped position;

a sensor circuit comprising a first electrode positioned on said first jaw and a second electrode positioned on said second jaw, wherein said first electrode and said second electrode are configured to contact each other when said first jaw is in said clamped position and an implantable adjunct is not positioned intermediate said first jaw and said second jaw, and wherein said first electrode and said second electrode are separated from each other when said first jaw is in said clamped position and an implantable adjunct is positioned intermediate said first jaw and said second jaw; and a motor control system in communication with said closure motor, said drive motor, and said sensor circuit, wherein said motor control system is configured to control the operation of said closure motor and said drive motor, and wherein said motor control system is configured to decrease a speed of said drive motor and said tissue cutting stroke when said sensor circuit detects the presence of an implantable adjunct intermediate said first jaw and said second jaw.

13. The surgical instrument of claim 12, further comprising a staple cartridge positioned in said first jaw, wherein said staple cartridge comprises:

a cartridge body;

staples removably stored in said cartridge body; and an implantable adjunct removably attached to said cartridge body.

14. The surgical instrument of claim 12, further comprising a staple cartridge positioned in said second jaw, wherein said staple cartridge comprises:

a cartridge body;

staples removably stored in said cartridge body; and an implantable adjunct removably attached to said cartridge body.

15. The surgical instrument of claim 12, further comprising an implantable adjunct releasably attached to said first jaw.

16. The surgical instrument of claim 12, further comprising an implantable adjunct releasably attached to said second jaw.

17. The surgical instrument of claim 12, wherein said motor control system comprises a pulse width modulation circuit configured to control the speed of said drive motor.

18. The surgical instrument of claim 12, wherein said motor control system comprises a frequency modulation circuit configured to control the speed of said drive motor.

19. The surgical instrument of claim 12, wherein said sensor circuit comprises an electrode configured to at least one of (i) contact the implantable adjunct or (ii) be positioned near the implantable adjunct.

20. The surgical instrument of claim 19, wherein said electrode is positioned on said first jaw.

* * * * *